(12) United States Patent
Agnew et al.

(10) Patent No.: US 8,114,636 B2
(45) Date of Patent: Feb. 14, 2012

(54) LABELING AND DETECTION OF NUCLEIC ACIDS

(75) Inventors: Brian Agnew, Eugene, OR (US); Maura J. Ford, Eugene, OR (US); Kyle R. Gee, Springfield, OR (US); Kapil Kumar, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 493 days.

(21) Appl. No.: 11/674,623

(22) Filed: Feb. 13, 2007

(65) Prior Publication Data

US 2008/0050731 A1 Feb. 28, 2008

Related U.S. Application Data

(63) Continuation-in-part of application No. 11/674,140, filed on Feb. 12, 2007.

(60) Provisional application No. 60/804,640, filed on Jun. 13, 2006, provisional application No. 60/772,221, filed on Feb. 10, 2006.

(51) Int. Cl.
*C12P 19/34* (2006.01)
*C12Q 1/68* (2006.01)
*C07H 21/02* (2006.01)
*C07H 21/04* (2006.01)

(52) U.S. Cl. ......... 435/91.1; 435/6; 536/23.1; 536/24.3; 536/26.6; 422/61

(58) Field of Classification Search ............. 435/6, 91.1; 536/23.1, 24.3, 26.6; 422/61
See application file for complete search history.

(56) References Cited

U.S. PATENT DOCUMENTS

| | | | |
|---|---|---|---|
| 5,279,954 | A | 1/1994 | Wagner et al. |
| 5,874,532 | A | 2/1999 | Pieken et al. |
| 6,255,475 | B1 | 7/2001 | Kwiatkowski |
| 6,570,040 | B2 | 5/2003 | Saxon et al. |
| 6,737,236 | B1 | 5/2004 | Pieken et al. |
| 7,122,703 | B2 | 10/2006 | Saxon et al. |
| 7,375,234 | B2 | 5/2008 | Sharpless et al. |
| 7,427,678 | B2 | 9/2008 | Pieken et al. |
| 7,763,736 | B2 | 7/2010 | Sharpless et al. |
| 2005/0032081 | A1 | 2/2005 | Ju et al. |
| 2005/0222427 | A1 | 10/2005 | Sharpless |
| 2006/0147963 | A1* | 7/2006 | Barone et al. ............... 435/6 |
| 2006/0276658 | A1 | 12/2006 | Saxon |
| 2009/0215635 | A1 | 8/2009 | Carell et al. |
| 2009/0240030 | A1 | 9/2009 | Ju et al. |
| 2010/0261181 | A1 | 10/2010 | Agnew et al. |

FOREIGN PATENT DOCUMENTS

| | | |
|---|---|---|
| WO | WO-96/09316 | 3/1996 |
| WO | WO-96/20289 | 7/1996 |
| WO | WO-96/34984 | 11/1996 |
| WO | WO-98/30575 | 7/1998 |
| WO | WO-01/68565 | 9/2001 |

(Continued)

OTHER PUBLICATIONS

08729780.0, "Extended European Search Report mailed Mar. 15, 2010".

(Continued)

*Primary Examiner* — Jezia Riley

(57) ABSTRACT

Provided in certain embodiments are new methods for forming azido modified nucleic acid conjugates of reporter molecules, carrier molecules or solid support. In other embodiments are provided methods for enzymatically labeling nucleic acids with an azide group.

9 Claims, 10 Drawing Sheets

FOREIGN PATENT DOCUMENTS

| WO | WO-02/29003 | 4/2002 |
| WO | WO-03/101972 A1 | 12/2003 |
| WO | WO-2004/018497 | 3/2004 |
| WO | WO-2006/038184 | 4/2006 |
| WO | WO-2006/117161 | 11/2006 |

OTHER PUBLICATIONS

Hassane, Fatouma S. et al., "Targeted liposomes: convenient coupling of ligands to preformed vesicles using click chemistry", Bioconjugate Chemistry, vol. 17, No. 3, May-Jun. 2006, pp. 849-854.

Kolb, H. C. et al., "Click Chemistry: Diverse Chemical Function from a Few Good Reactions", Anciewandte Chemie International Edition in English, vol. 40, 2001, pp. 2004-2021.

Langenhan, J. M. et al., "Recent carbohydrate-based chemoselective ligation applications", Current Organic Synthesis, vol. 2, No. 1, Jan. 2005, pp. 59-81.

Lewis, W. G. et al., "Click chemistry in Situ: Acetylcholinesterase as a Reaction Vessel for the Selectivity Assembly of a Femtomolar Inhibitor from an Array of building Blocks", Angewandte Chemie International Edition in English, vol. 41, No. 6, 2002, pp. 1053-1057.

PCT/US08/053870, "International Preliminary Report on Patentability mailed Jul. 31, 2008".

PCT/US08/053870, "Written Opinion mailed Jul. 31, 2008".

PCT/US08/053870, "Search Report mailed on Jul. 31, 2008".

Rostovtsev, et al., "A step-wise Huisgen cycloaddition process copper (I)—catalyzed regioselective ligation of azides and terminal alkynes", Angewandte Chemie. International Edition, vol. 41, No. 14, 2002, pp. 2596-2599.

Saxon, Eliana et al., "Cell Surface Engineering by a Modified Staudinger Reaction.", Science, vol. 287, No. 5460, Mar. 17, 2000, pp. 2007-2010.

Tornøe, et al., "Peptidotriazoles on Solid Phase: [1,2,3]-Triazoles by Regiospecific Copper(I)—Catalyzed 1,3-Dipolar Cycloadditions of Terminal Alkynes to Azides", J. Org. Chem., vol. 67, 2002, pp. 3057-3064.

Wang, Qian et al., "Bioconjugation by Copper(I)—Catalyzed Azide-Alkyne [3+2] Cycloaddition", Journal of the American Chemical Society, vol. 125, No. 11, 2003, pp. 3192-3193.

Antos, J. M. et al., "Transition metal catalyzed methods for site-selective protein modification", Current Opinion in Chemical Biology; vol. 10(3) Jun. 1, 2006, 253-262.

10153793.4, "Extended European Search Report mailed Jul. 12, 2010".

Anonymous, "Telomerase PCR ELISA. For fast and sensitive detection of telomerase activity." Biochemica, [Online] vol. 1996, No. 4, p. 7-8.

Anonymous, TRAPeze telomerase detection kit. S770 XP7913582 2005.

Rodionov, V. et al., "Mechanism of the Ligand-Free Cu-Catalyzed Azide-Alkyne Cycloaddition Reaction", Angew. Chem. Int. Ed. vol. 44, 2005, 2210-2215.

Speers, Anna E. et al., "Profiling Enzyme Activities In Vivo Using Click Chemistry Methods", Chemistry & Biology vol. 11, 2004, 535-546.

Response, filed Jan. 17, 2011, to European Office action (dated Jul. 7, 2010) in European Application No. 08729780.0.

Office Action in U.S. Appl. No. 11/674,140 mailed Oct. 19, 2010.

Lee., B., et al. "Interaction of Psoralen-Derivatized Oligodeoxyribonucleoside Methylphosphonates with single-Stranded DNA", Biochemistry, 1988, vol. 27, pp. 3197-3203.

Pei, Y., et al. "Post-Modification of Peptoid Side Chains: [3+2] Cycloaddition of Nitrole Oxides with Alkenes and Alkynes on the Solid-Phase", Tetrahedron Letters, 1994, vol. 35, No. 32, pp. 5825-5828.

Wang, Q., et al. "Bioconjugation by Copper (I)—Catalyzed Azide-Alkyne [3+2] Cycloaddition", J. Am. Chem. Soc. 2003, vol. 125, pp. 3192-3193.

Fukui, T., "Addition of potato recovered from potato starch factory waste effluents for bread", Internet Citation, 25(1):1978, p. 43-46.

Murakami, N. et al., "Studies on Cardiac Ingrediets of Plants. VII: Chemical Transformation of Proscillaridin by Means of the Diels-Alder Reaction and Biological Activities of its Derivatives", Chem. Pharm. Bull. 39 (8):1991, p. 1962-1966.

* cited by examiner

DOSE-DEPENDENCE OF N$_3$-dATP-LABELED TRAP DNA BY PAGE

DOSE-DEPENDENCE OF E-dUTP-LABELED TRAP DNA BY PAGE

INCORPORATION OF E-dUTP IN AN ISOTHERMAL EXTENSION ASSAY
USING DIFFERENT POLYMERASES

BCS ELIMINATES "CLICK-LABELED BAND" AND
PRESERVES TRAP LADDERING

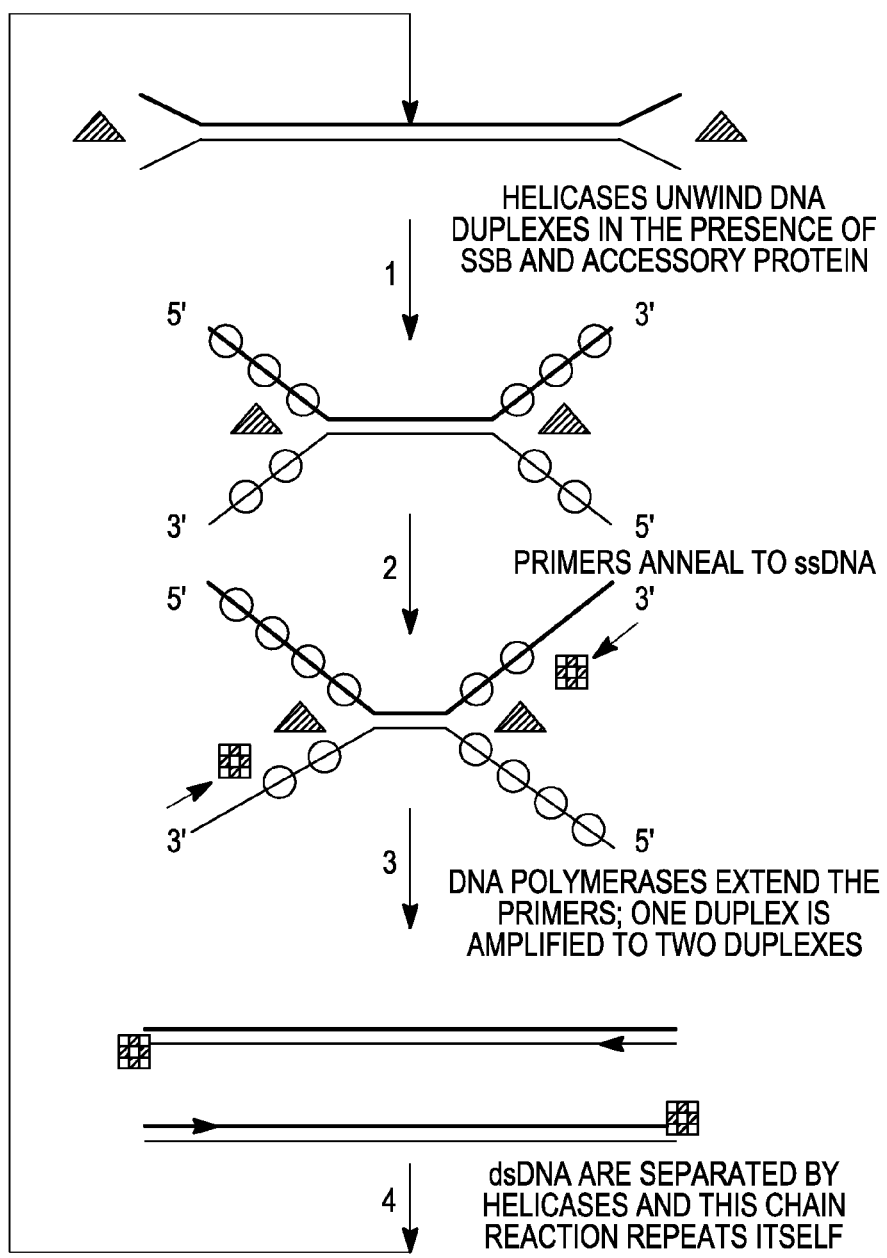

SCHEMATIC DIAGRAM OF HDA. TWO COMPLEMENTARY DNA STRANDS ARE SHOWN AS TWO LINES; THE THICK ONE IS THE TOP STRAND AND THE THIN ONE IS THE BOTTOM STRAND.
1: A HELICASE (BLACK TRIANGLE) SEPARATES THE TWO COMPLEMENTARY DNA STRANDS, WHICH ARE BOUND BY SSB (GREY CIRCLES).
2: PRIMERS (LINES WITH ARROW HEADS) HYBRIDIZE TO THE TARGET REGION ON THE ssDNA TEMPLATE.
3: A DNA POLYMERASE (SQUARES WITH MOSAIC PATTERNS) EXTENDS THE PRIMERS HYBRIDIZED ON THE TEMPLATE DNA.
4: AMPLIFIED PRODUCTS ENTER THE NEXT ROUND OF AMPLIFICATION.

*FIG. 8*

SEQUENCE LISTING

<160> NUMBER OF SEQ ID NOS: 3

<210> SEQ ID NO 1
<211> LENGTH: 70
<212> TYPE: DNA
<213> ORGANISM: Artificial
<220> FEATURE:
<223> OTHER INFORMATION: Oligo 3

<400> SEQUENCE: 1
ttagggttag ggttagggtt tgggtttggg tttgggtttg ggtttgggtt tgggctggcc    60
gtcgttttac                                                          70

<210> SEQ ID NO 2
<211> LENGTH: 70
<212> TYPE: DNA
<213> ORGANISM: Artificial
<220> FEATURE:
<223> OTHER INFORMATION: Oligo 3

<400> SEQUENCE: 2
tttgggtttg ggtttgggtt tgggtttggg tttgggttag ggtttgggtt tgggctggcc    60
gtcgttttac                                                          70

<210> SEQ ID NO 3
<211> LENGTH: 16
<212> TYPE: DNA
<213> ORGANISM: Artificial

```
<220> FEATURE:
<223> OTHER INFORMATION: Oligo 3

<400> SEQUENCE: 3
gtaaaacgac ggccag                                                  16
```

LABELING AND DETECTION OF NUCLEIC ACIDS

CROSS REFERENCE TO RELATED APPLICATION(S)

This application is a Continuation-in-Part of U.S. Ser. No. 11/674,140, filed Feb. 12, 2007, which claims priority to U.S. Provisional Application No. 60/772,221, filed Feb. 10, 2006 and U.S. Provisional Application No. 60/804,640, filed Jun. 13, 2006, the contents of which are incorporated by reference as if set forth fully herein.

SEQUENCE LISTING

The instant application contains a Sequence Listing which is incorporated herein by reference in its entirety.

FIELD OF THE INVENTION

The invention generally relates to methods of labeling nucleic acid polymers and their use.

BACKGROUND INFORMATION

Conventional methods for labeling nucleotides are straightforward, but have significant drawbacks. With direct fluorophore labeling, the bulky dye molecule on the nucleotide makes it difficult for the enzyme to incorporate nucleotides into DNA or RNA strands. Additionally, protocols optimized for one fluorophore may not be optimal for another, chemically different fluorophore.

Various methods have been used to generate labeled probes for hybridization to Southern blots and microarrays, for example, 5' and 3' end labeling with $^{32}P$. Additionally, nick translation uses DNAse I to generate single stranded nicks in the nucleic acid starting material and DNA polymerase to fill in the nicks. A labeled deoxynucleotide (for example dUTP-digoxigenin or dUTP fluorescein) is included in the reaction mixture, along with the other unlabeled deoxynucleotides. While these methods generate labeled probes, they do not provide a method of amplifying the starting material.

Polymerase chain reaction (PCR) in the presence of a mixture of nucleotides (for example dATP, dCTP, dGTP, dTTP, and modified dUTP-digoxigenin or fluorescein) can be used to synthesize copies of a template strand. These amplicons can be used as probes for hybridization assays. The mixture must contain unmodified dTTP in addition to modified dUTP in order for the reaction to take place.

PCR uses a double stranded DNA template as starting material. This template can be made from RNA by reverse transcription and subsequently labeled by PCR incorporation of labeled nucleotides. While this method does result in an amplification of the starting material, the substitution of the deoxynucleotide fluorescent analogue is less than 100% and the specific activity may be variable, depending on the label.

Accordingly, one object of the present invention is to provide an improved method for nucleotide labeling that circumvents problems associated with conventional methods. Preferably, the methods will be amenable to a variety of uses including generating FISH probes, generating probes for Southern blots, generating probes for Northern blots, calorimetric in situ hybridization probes (CISH), in situ PCR, isothermal amplification in situ, DNA fingerprinting, and SNP detection.

SUMMARY OF THE INVENTION

One aspect of the invention provides a method of forming a nucleic acid conjugate, wherein the method comprises:

incorporating an azide modified nucleotide into the nucleic acid polymer by contacting the azide modified nucleotide with at least one other nucleotide in the presence of a DNA amplification enzyme to form an azide modified nucleic acid polymer; and contacting the azide modified nucleic acid polymer with a reporter molecule, carrier molecule or solid support that comprises an activated or terminal alkyne or phosphine moiety to form a nucleic acid polymer-reporter molecule, carrier molecule, solid support conjugate.

Another aspect of the invention provides method of forming a nucleic acid conjugate, wherein the method comprises:

incorporating a terminal alkyne modified nucleotide into the nucleic acid polymer by contacting the terminal alkyne modified nucleotide with at least one other nucleotide in the presence of a DNA amplification enzyme to form a terminal alkyne modified nucleic acid polymer; and contacting the terminal alkyne modified nucleic acid polymer with a reporter molecule, carrier molecule or solid support that comprises an azido moiety to form a nucleic acid polymer-reporter molecule, carrier molecule, solid support conjugate.

Another aspect of the invention provides a method of forming a nucleic acid conjugate, wherein the method comprises:

incorporating a phosphine modified nucleotide into the nucleic acid polymer by contacting the phosphine modified nucleotide with at least one other nucleotide in the presence of a DNA amplification enzyme to form a phosphine modified nucleic acid polymer; and contacting the phosphine modified nucleic acid polymer with a reporter molecule, carrier molecule or solid support that comprises an azido moiety to form a nucleic acid polymer-reporter molecule, carrier molecule, solid support conjugate.

Another aspect of the invention provides a method for making an azido, alkyne or phosphine modified nucleic acid polymer, wherein the method comprises:

incubating at least one azido, alkyne or phosphine modified nucleotide in the presence of a nucleic acid amplification enzyme to form an azido, alkyne or phosphine modified nucleic acid polymer.

In another embodiment, the nucleic acid enzyme is a DNA polymerase.

In another embodiment, the nucleic acid enzyme is a RNA polymerase.

In another embodiment, the melting temperature of the azido, alkyne or phosphine modified nucleic acid polymer is increased.

In another embodiment, the reporter molecule is a xanthene, cyanine, coumarin, borapolyazaindacene or pyrene dye. In another embodiment, the reporter molecule is an enzyme substrate or hapten.

In another embodiment, the carrier molecule is an amino acid, a peptide, a protein, a polysaccharide, a nucleotide, a nucleoside, an oligonucleotide, a nucleic acid, a hapten, a psoralen, a drug, a hormone, a lipid, a lipid assembly, a synthetic polymer, a polymeric microparticle, a biological cell or a virus. In another embodiment, the carrier molecule comprises an antibody or fragment thereof, an avidin or streptavidin, a biotin, a blood component protein, a dextran, an enzyme, an enzyme inhibitor, a hormone, an IgG binding protein, a fluorescent protein, a growth factor, a lectin, a lipopolysaccharide, a microorganism, a metal binding protein, a metal chelating moiety, a non-biological microparticle, a peptide toxin, a phosphotidylserine-binding protein, a structural protein, a small-molecule drug, or a tyramide.

In another embodiment, the solid support is a microfluidic chip, a silicon chip, a microscope slide, a microplate well, silica gels, polymeric membranes, particles, derivatized plastic films, glass beads, cotton, plastic beads, alumina gels, polysaccharides, polyvinylchloride, polypropylene, polyethylene, nylon, latex bead, magnetic bead, paramagnetic bead, or superparamagnetic bead.

In another embodiment, the solid support is Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose or starch.

Another aspect of the invention provides a method of detecting an azido modified nucleic acid polymer, comprising:
   forming an azide-alkyne cycloaddition reaction mixture comprising:
   a reporter molecule that comprises a terminal alkyne moiety:
   an azido modified nucleic acid polymer;
   incubating the azide-alkyne cycloaddition reaction mixture for a sufficient amount of time to form a nucleic acid polymer-reporter molecule conjugate;
   separating the nucleic acid polymer-reporter conjugate by size and/or weight of the nucleic acid polymer-reporter-reporter molecule conjugate to form a separated nucleic acid polymer-reporter-reporter molecule conjugate;
   illuminating the separated nucleic acid polymer-reporter-reporter molecule conjugate with an appropriate wavelength to form an illuminated nucleic acid polymer-reporter-reporter molecule conjugate;
   observing the illuminated nucleic acid polymer-reporter-reporter molecule conjugate wherein the nucleic acid polymer is detected.

In a more particular embodiment the forming step further comprises
   a. copper ions;
   b. at least one reducing agent; and
   c. a copper chelator.

In another embodiment, the reporter molecule is xanthene, cyanine, coumarin, borapolyazaindacene or pyrene dye. In another embodiment, the reporter molecule is an enzyme substrate, fluorescent protein or hapten.

In another embodiment, the copper chelator is a copper (I)chelator. In another embodiment, the copper chelator is N,N,N',N'-tetrakis(2-pyridylmethyl)ethylenediamine (TPEN), EDTA, neocuproine, N-(2-acetamido)iminodiacetic acid (ADA), pyridine-2,6-dicarboxylic acid (PDA), S-carboxymethyl-L-cysteine (SCMC), 1,10 phenanthroline, or a derivative thereof, trientine, glutathione, histidine, polyhistadine or tetra-ethylenepolyamine (TEPA). In another embodiment, the copper chelator is 1,10 phenanthroline, bathophenanthroline disulfonic acid (4,7odiphenyl-1,10-phenanthroline disulfonic acid) or bathocuproine disulfonic acid (2,9-dimethyl-4,7-diphenyl-1,10-phenanthroline disulfonate).

In another embodiment, the reducing agent is acorbate, Tris(2-Carboxyethyl) Phosphine (TCEP), TCP (2,4,6-trichlorophenol), NADH, NADPH, thiosulfate, 2-mercaptoethanol, dithiothreotol, glutathione, cysteine, metallic copper, quinone, hydroquinone, vitamin $K_1$, $Fe^{2+}$, $Co^{2+}$, or an applied electric potential. In another embodiment, the reducing agent is ascorbate.

In another embodiment, the separating step comprises chromatography or electrophoresis. In another embodiment, the chromatography comprises one or more of FPLC, HPLC, liquid chromatograpy (LC), size exclusion chromatography, ion exchange chromatography, or affinity chromatography.

In another embodiment, electrophoresis comprises gel electrophoresis, 1 dimensional (1D) gel electrophoresis, 2 dimensional (2D) gel electrophoresis, native gel electrophoresis, denaturing gel electrophoresis, isoelectric focusing, or capillary electrophoresis.

Another aspect of the invention provides an azide-alkyne cycloaddition reaction mixture comprising:
   a reporter molecule that comprises a terminal alkyne moiety:
   an azido modified nucleic acid;
   copper ions;
   at least one reducing agent; and
   a copper chelator.

Another aspect of the invention provides a method for detecting immobilized azido modified nucleic acids, wherein the method comprises:
   immobilizing the azido modified nucleic acids on a solid or semi-solid matrix to form an immobilized azido modified nucleic acid;
   contacting the immobilized azido modified nucleic acid with a reporter molecule that contains an azide reactive group to form a contacted azido modified nucleic acid;
   incubating the contacted azido modified nucleic acid for a sufficient amount of time to form a reporter molecule-nucleic acid conjugate;
   illuminating the reporter molecule-nucleic acid conjugate with an appropriate wavelength to form an illuminated reporter molecule-nucleic acid conjugate;
   observing the illuminated reporter molecule-nucleic acid conjugate whereby the immobilized azido modified nucleic acid is detected.

Another aspect of the invention provides a method for detecting immobilized alkyne modified nucleic acids, wherein the method comprises:
   immobilizing the alkyne modified nucleic acids on a solid or semi-solid matrix to form an immobilized alkyne modified nucleic acid;
   contacting the immobilized alkyne modified nucleic acid with a reporter molecule that contains an azido group to form a contacted alkyne modified nucleic acid;
   incubating the contacted alkyne modified nucleic acid for a sufficient amount of time to form a reporter molecule-nucleic acid conjugate;
   illuminating the reporter molecule-nucleic acid conjugate with an appropriate wavelength to form an illuminated reporter molecule-nucleic acid conjugate;
   observing the illuminated reporter molecule-nucleic acid conjugate whereby the immobilized alkyne modified nucleic acid is detected.

In another embodiment, the solid or semi-solid support is a slide, an array, an agarose gel, a polyacrylamide gel, a hydrogel, a polymeric particle or glass.

Another aspect of the invention provides a kit comprising:
   Azide-dATP;
   a telomerase enzyme;
   an azide reactive reporter molecule, carrier molecule or solid support.

Another aspect of the invention provides a kit for labeling a nucleic acid polymer comprising:
   at least one nucleotide analogue that comprises an azide, alkyne or phosphine moiety; and
   a reporter molecule, carrier molecule or solid support comprising an azide, alkyne or phosphine moiety.

A more particular embodiment thereof further comprises a nucleic acid amplification enzyme.

Another aspect of the invention provides a method of measuring Telomerase Enzyme Activity, comprising steps of:
a) contacting a cell with an effective amount of a dNTP nucleotide that comprises an azide group and a Telomerase enzyme such that the dNTP nucleotide is incorporated into at least one nucleic acid polymer;
b) contacting the nucleic acid polymer with a reporter molecule comprising an alkyne or phosphine moiety to form a azido modified nucleic acid polymer reporter molecule conjugate;
c) separating the azido modified nucleic acid polymer reporter molecule conjugate from nucleic acid polymers that do not comprise a reporter molecule, and
d) illuminating the azido modified nucleic acid polymer reporter molecule conjugate to determine Telomerase activity.

Another aspect of the invention provides a method of measuring Telomerase Enzyme Activity, comprising steps of:
a) contacting a cell with an effective amount of a dNTP nucleotide that comprises an alkyne or phosphine group and a Telomerase enzyme such that the dNTP nucleotide is incorporated into at least one nucleic acid polymer;
b) contacting the nucleic acid polymer with a reporter molecule comprising an azido moiety to form an alkyne or phosphine modified nucleic acid polymer reporter molecule conjugate;
c) separating the alkyne or phosphine modified nucleic acid polymer reporter molecule conjugate from nucleic acid polymers that do not comprise a reporter molecule, and
d) illuminating the alkyne or phosphine modified nucleic acid polymer reporter molecule conjugate to determine Telomerase activity.

BRIEF DESCRIPTION OF THE DRAWINGS

FIG. (1): Shows in gel detection Telomerase incorporation of $N_3$-dATP.

FIG. (2): Shows in gel detection and dose-dependence of Telomerase incorporation of $N_3$-dATP and not $N_3$-dAUP.

Figure 1:
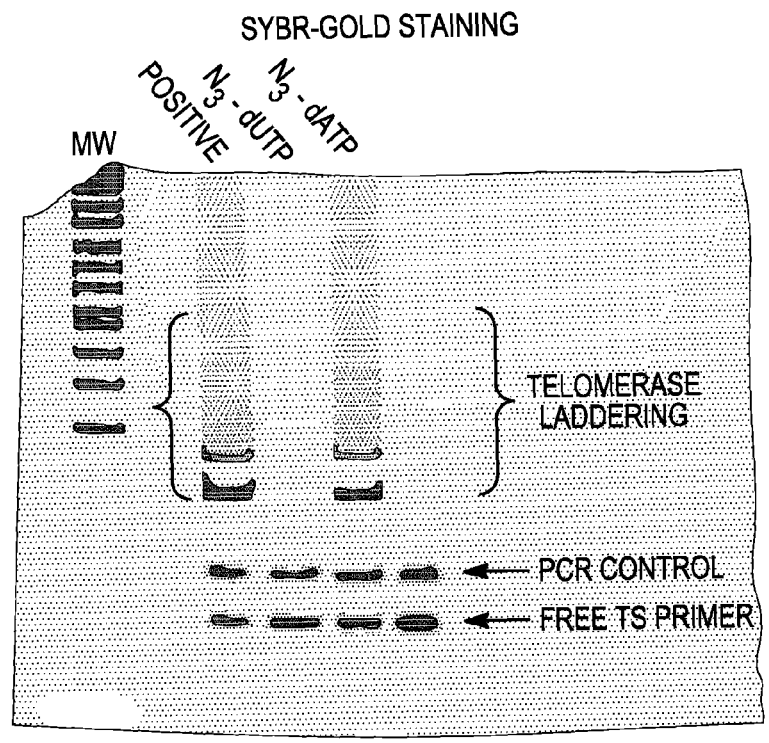

FIG. (3): Shows in gel detection and dose-dependence of Telomerase incorporation of $N_3$-dATP and labeled with alkyne-TAMRA using "click" chemistry.

FIG. (4): Shows in gel detection of Telomerase incorporation of ethynyl-dAUP and labeled with azide-TAMRA using "click" chemistry.

FIG. (5): Shows in gel detection of Telomerase incorporation of ethynyl-dAUP and labeled with azide-TAMRA using "click" chemistry.

FIG. (6): Shows in gel detection of incorporation of ethynyl-dAUP using linear amplification and various polymerases. The ethynyl-dAUP was labeled with azide-TAMRA using "click" chemistry.

FIG. (7): Shows that the presence of a copper chelator (BCS) maintains Telomerase laddering.

FIG. (8): Is a schematic diagram showing amplification using helicase enzyme.

FIG. (9): Is a schematic diagram showing Strand Displacement Amplification (SDA)

FIG. (10): Illustration of the position of the primers used in Example 13, giving a predicted amplicon size of 293 bp.

FIG. (11): Is a linear amplification plot showing that the onset of exponential amplification or threshold cycle (CT) for the click modified dUTP mix is very similar to that shown for the unmodified dUTP mix. The average CT for click dUTP is 9.78 vs 10.97 for unmodified dUTP.

FIG. (12): Shows dissociation curves for the reactions in Example 13, showing the change in fluorescence as a function of temperature. Click modified dUTP mix melts at 93 C, vs unmodified dUTP mix at 88 C.

FIG. (13): Gel analysis of real-time PCR products scanned for TAMRA (left) or scanned after labeling with SYBR GOLD (right).

FIG. (14): shows images of reaction tubes for TAMRA.

FIG. (15): shows a dot blot of reaction products scanned for TAMRA.

FIG. (16): shows the experimental setup for Example 15.

DETAILED DESCRIPTION OF THE INVENTION

Definitions and Abbreviations

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a ligand" includes a plurality of ligands and reference to "a nucleic acid" includes a plurality of nucleic acids and the like.

Unless defined otherwise, all technical and scientific terms used herein have the same meaning as commonly understood by one of ordinary skill in the art to which this invention is related. The following terms and abbreviations (Table 1) are defined for purposes of the invention as described herein.

TABLE 1

| List of Abbreviations | |
|---|---|
| Abbreviation | Term. |
| E-dNTP | ethynyl deoxynucleoside triphosphate |
| E-ATP | ethynyl deoxyadenosine triphosphate |
| E-GTP | ethynyl deoxyguanosine triphosphate |
| E-CTP | ethynyl deoxycytidine triphosphate |
| E-TTP | ethynyl deoxythymidine triphosphate |

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds described herein may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S ENCYCLOPEDIA OF PRACTICAL ORGANIC CHEMISTRY $5^{TH}$ ED., Longman Scientific and Technical Ltd., Essex, 1991, pp. 809-816; and Heller, *Acc. Chem. Res.* 23: 128 (1990).

The compounds disclosed herein may also contain unnatural proportions of atomic isotopes at one or more of the atoms that constitute such compounds. For example, the compounds may be radiolabeled with radioactive isotopes, such as for example tritium (3H), iodine-125 ($^{125}$I) or carbon-14 ($^{14}$C). All isotopic variations of the compounds of the present invention, whether radioactive or not, are intended to be encompassed within the scope of the present invention.

Where a disclosed compound includes a conjugated ring system, resonance stabilization may permit a formal electronic charge to be distributed over the entire molecule. While a particular charge may be depicted as localized on a particular ring system, or a particular heteroatom, it is commonly understood that a comparable resonance structure can be drawn in which the charge may be formally localized on an alternative portion of the compound.

Selected compounds having a formal electronic charge may be shown without an appropriate biologically compatible counterion. Such a counterion serves to balance the positive or negative charge present on the compound. As used herein, a substance that is biologically compatible is not toxic as used, and does not have a substantially deleterious effect on biomolecules. Examples of negatively charged counterions include, among others, chloride, bromide, iodide, sulfate, alkanesulfonate, arylsulfonate, phosphate, perchlorate, tetrafluoroborate, tetraarylboride, nitrate and anions of aromatic or aliphatic carboxylic acids. Preferred counterions may include chloride, iodide, perchlorate and various sulfonates. Examples of positively charged counterions include, among others, alkali metal, or alkaline earth metal ions, ammonium, or alkylammonium ions.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "acyl" or "alkanoyl" by itself or in combination with another term, means, unless otherwise stated, a stable straight or branched chain, or cyclic hydrocarbon radical, or combinations thereof, consisting of the stated number of carbon atoms and an acyl radical on at least one terminus of the alkane radical. The "acyl radical" is the group derived from a carboxylic acid by removing the —OH moiety therefrom.

The term "alkyl," by itself or as part of another substituent means, unless otherwise stated, a straight or branched chain, or cyclic hydrocarbon radical, or combination thereof, which may be fully saturated, mono- or polyunsaturated and can include divalent ("alkylene") and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

Exemplary alkyl groups of use in the present invention contain between about one and about twenty five carbon atoms (e.g. methyl, ethyl and the like). Straight, branched or cyclic hydrocarbon chains having eight or fewer carbon atoms will also be referred to herein as "lower alkyl". In addition, the term "alkyl" as used herein further includes one or more substitutions at one or more carbon atoms of the hydrocarbon chain fragment.

The term "amino" or "amine group" refers to the group —NR'R" (or NRR'R") where R, R' and R" are independently selected from the group consisting of hydrogen, alkyl, substituted alkyl, aryl, substituted aryl, aryl alkyl, substituted aryl alkyl, heteroaryl, and substituted heteroaryl. A substituted amine being an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —NRR'R" and its biologically compatible anionic counterions.

The term "aryl" as used herein refers to cyclic aromatic carbon chain having twenty or fewer carbon atoms, e.g., phenyl, naphthyl, biphenyl, and anthracenyl. One or more carbon atoms of the aryl group may also be substituted with, e.g., alkyl; aryl; heteroaryl; a halogen; nitro; cyano; hydroxyl, alkoxyl or aryloxyl; thio or mercapto, alkyl-, or arylthio; amino, alkylamino, arylamino, dialkyl-, diaryl-, or arylalkylamino; aminocarbonyl, alkylaminocarbonyl, arylaminocarbonyl, dialkylaminocarbonyl, diarylaminocarbonyl, or arylalkylaminocarbonyl; carboxyl, or alkyl- or aryloxycarbonyl; aldehyde; aryl- or alkylcarbonyl; iminyl, or aryl- or alkyliminyl; sulfo; alkyl- or alkylcarbonyl; iminyl, or aryl- or alkyliminyl; sulfo; alkyl- or arylsulfonyl; hydroximinyl, or aryl- or alkoximinyl. In addition, two or more alkyl or heteroalkyl substituents of an aryl group may be combined to form fused aryl-alkyl or aryl-heteroalkyl ring systems (e.g., tetrahydronaphthyl). Substituents including heterocyclic groups (e.g., heteroaryloxy, and heteroaralkylthio) are defined by analogy to the above-described terms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a straight or branched chain, or cyclic carbon-containing radical, or combinations thereof, consisting of the stated number of carbon atoms and at least one heteroatom selected from the group consisting of O, N, Si, P, S, and Se and wherein the nitrogen, phosphorous, sulfur, and selenium atoms are optionally oxidized, and the nitrogen heteroatom is optionally be quaternized. The heteroatom(s) O, N, P, S, Si, and Se may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$,—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, aromatic moiety that can be a single ring or multiple rings (preferably from 1 to 3 rings), which are fused together or linked covalently. The term "heteroaryl" refers to aryl groups (or rings) that contain from one to four heteroatoms selected from N, O, S, and Se, wherein the nitrogen, sulfur, and selenium atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound includes more than one R group, for example, each of the R groups is independently selected as are each R', R", R'" and R"" groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—.

The substituents R, R', R" and R'" are preferably independently selected from hydrogen or substituted or unsubstituted $(C_1-C_6)$alkyl.

As used herein, the term "heteroatom" includes oxygen (O), nitrogen (N), sulfur (S), phosphorus (P), silicon (Si), and selenium (Se).

The term "amino" or "amine group" refers to the group —NR'R" (or N$^+$RR'R") where R, R' and R" are independently selected from the group consisting of hydrogen, alkyl, substituted alkyl, aryl, substituted aryl, aryl alkyl, substituted aryl alkyl, heteroaryl, and substituted heteroaryl. A substituted amine being an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —N$^+$RR'R" and its biologically compatible anionic counterions.

The term "aqueous solution" as used herein refers to a solution that is predominantly water and retains the solution characteristics of water. Where the aqueous solution contains solvents in addition to water, water is typically the predominant solvent.

The term "Carboxyalkyl" as used herein refers to a group having the general formula —(CH$_2$)$_n$COOH wherein n is 1-18.

The term "activated alkyne," as used herein, refers to a chemical moiety that selectively reacts with an alkyne reactive group, such as an azido moiety or an phosphine moiety, on another molecule to form a covalent chemical bond between the activated alkyne group and the alkyne reactive group. Examples of alkyne-reactive groups include azides. "Alkyne-reactive" can also refer to a molecule that contains a chemical moiety that selectively reacts with an alkyne group. As used herein activated alkyne encompasses any terminal alkynes or cyclooctynes (dipolarophiles) that will react with 1,3-dipoles such as azides in a facile fashion.

The term "aqueous solution," as used herein, refers to a solution that is predominantly water and retains the solution characteristics of water. Where the aqueous solution contains solvents in addition to water, water is typically the predominant solvent.

The term "azide reactive," as used herein, refers to a chemical moiety that selectively reacts with an azido modified group on another molecule to form a covalent chemical bond between the azido modified group and the azide reactive group. Examples of azide-reactive groups include alkynes and phosphines (e.g. triaryl phosphine). "Azide-reactive" can also refer to a molecule that contains a chemical moiety that selectively reacts with an azido group.

The term "buffer," as used herein, refers to a system that acts to minimize the change in acidity or basicity of the solution against addition or depletion of chemical substances.

The term "carrier molecule," as used herein, refers to a biological or a non-biological component that is covalently bonded to compound of the present invention. Such components include, but are not limited to, an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof.

The term, "chemical handle" as used herein refers to a specific functional group, such as an azide, alkyne, activated alkyne, phosphite, phosphine, and the like. The chemical handle is distinct from the reactive group, defined below, in that the chemical handle are moieties that are rarely found in naturally-occurring biomolecules and are chemically inert towards biomolecules (e.g., native cellular components), but when reacted with an azide- or alkyne-reactive group the reaction can take place efficiently under biologically relevant conditions (e.g., cell culture conditions, such as in the absence of excess heat or harse reactants).

The term "click chemistry," as used herein, refers to the Huisgen cycloaddition or the 2,3-dipolar cycloaddition between an azide and a terminal alkyne to form a 1,2,4-triazole. Such chemical reactions can use, but are not limited to, simple heteroatomic organic reactants and are reliable, selective, stereospecific, and exothermic.

The term "cycloaddition" as used herein refers to a chemical reaction in which two or more $\pi$-electron systems (e.g., unsaturated molecules or unsaturated parts of the same molecule) combine to form a cyclic product in which there is a net reduction of the bond multiplicity. In a cycloaddition, the $\pi$ electrons are used to form new sigma bonds. The product of a cycloaddition is called an "adduct" or "cycloadduct". Different types of cycloadditions are known in the art including, but not limited to, [3+2] cycloadditions and Diels-Alder reactions. [3+2] cycloadditions, which are also called 2,3-dipolar cycloadditions, occur between a 1,3-dipole and a dipolarophile and are typically used for the construction of five-membered heterocyclic rings. The terms "[3+2] cycloaddition" also encompasses "copperless" [3+2] cycloadditions between azides and cyclooctynes and difluorocyclooctynes described by Bertozzi et al. J. Am. Chem. Soc., 2004, 126: 15046-15047.

The term "detectable response" as used herein refers to an occurrence of, or a change in, a signal that is directly or indirectly detectable either by observation or by instrumentation. Typically, the detectable response is an occurrence of a signal wherein the fluorophore is inherently fluorescent and does not produce a change in signal upon binding to a metal ion or biological compound. Alternatively, the detectable response is an optical response resulting in a change in the wavelength distribution patterns or intensity of absorbance or fluorescence or a change in light scatter, fluorescence lifetime, fluorescence polarization, or a combination of the above parameters. Other detectable responses include, for example, chemiluminescence, phosphorescence, radiation from radioisotopes, magnetic attraction, and electron density.

The term "detectably distinct" as used herein refers to a signal that is distinguishable or separable by a physical property either by observation or by instrumentation. For example, a fluorophore is readily distinguishable either by spectral characteristics or by fluorescence intensity, lifetime, polarization or photo-bleaching rate from another fluorophore in the sample, as well as from additional materials that are optionally present.

The term "directly detectable" as used herein refers to the presence of a material or the signal generated from the material is immediately detectable by observation, instrumentation, or film without requiring chemical modifications or additional substances.

The term "fluorophore" as used herein refers to a composition that is inherently fluorescent or demonstrates a change in fluorescence upon binding to a biological compound or metal ion, i.e., fluorogenic. Fluorophores may contain substitutents that alter the solubility, spectral properties or physical properties of the fluorophore. Numerous fluorophores are known to those skilled in the art and include, but are not limited to coumarin, cyanine, benzofuran, a quinoline, a quinazolinone, an indole, a benzazole, a borapolyazaindacene and xanthenes including fluoroscein, rhodamine and rhodol as well as other fluorophores described in RICHARD P. HAUGLAND, MOLECULAR PROBES HANDBOOK OF FLUORESCENT PROBES AND RESEARCH CHEMICALS (10$^{th}$ edition, CD-ROM, September 2005), which is herein incorporated by reference in its entirety.

The term "isolated", when used herein in reference to a nucleic acid polymer, means a nucleic acid polymer, which by virtue of its origin or manipulation is separated from at least some of the components with which it is naturally associated or with which it is associated when initially obtained. By "isolated", it is alternatively or additionally meant that the nucleic acid polymer of interest is produced or synthesized by the hand of man.

The term "kit," as used herein, refers to a packaged set of related components, typically one or more compounds or compositions.

The term "label," as used herein, refers to a chemical moiety or protein that is directly or indirectly detectable (e.g. due to its spectral properties, conformation or activity) when attached to a target or compound and used in the present methods, including reporter molecules and carrier molecules. The label can be directly detectable (fluorophore) or indirectly detectable (hapten or enzyme). Such labels include, but are not limited to, radiolabels that can be measured with radiation-counting devices; pigments, dyes or other chromogens that can be visually observed or measured with a spectrophotometer; spin labels that can be measured with a spin label analyzer; and fluorescent labels (fluorophores), where the output signal is generated by the excitation of a suitable molecular adduct and that can be visualized by excitation with light that is absorbed by the dye or can be measured with standard fluorometers or imaging systems, for example. The label can be a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The term label can also refer to a "tag" or hapten that can bind selectively to a conjugated molecule such that the conjugated molecule, when added subsequently along with a substrate, is used to generate a detectable signal. For example, one can use biotin as a tag and then use an avidin or streptavidin conjugate of horseradish peroxidase (HRP) to bind to the tag, and then use a calorimetric substrate (e.g., tetramethylbenzidine (TMB)) or a fluorogenic substrate such as Amplex Red reagent (Molecular Probes, Inc.) to detect the presence of HRP. Numerous labels are know by those of skill in the art and include, but are not limited to, particles, fluorophores, haptens, enzymes and their calorimetric, fluorogenic and chemiluminescent substrates and other labels that are described in RICHARD P. HAUGLAND, MOLECULAR PROBES HANDBOOK OF FLUORESCENT PROBES AND RESEARCH PRODUCTS (10$^{th}$ edition, CD-ROM, September 2005), supra.

The term "linker" or "L", as used herein, refers to a single covalent bond or a series of stable covalent bonds incorporating 1-30 nonhydrogen atoms selected from the group consisting of C, N, O, S and P. In addition, the linker covalently attaches a carrier molecule or solid support to the present azido or activated alkyne modified nucleotides or nucleic acid polymers. Exemplary linking members include a moiety that includes —C(O)NH—, —C(O)O—, —NH—, —S—, —O—, and the like. A "cleavable linker" is a linker that has one or more cleavable groups that may be broken by the result of a reaction or condition. The term "cleavable group" refers to a moiety that allows for release of a portion, e.g., a reporter molecule, carrier molecule or solid support, of a conjugate from the remainder of the conjugate by cleaving a bond linking the released moiety to the remainder of the conjugate. Such cleavage is either chemical in nature, or enzymatically mediated. Exemplary enzymatically cleavable groups include natural amino acids or peptide sequences that end with a natural amino acid. In addition to enzymatically cleavable groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleaveable groups are known in the art. See, for example, Jung et al., Biochem. Biophys. Acta, 761: 152-162 (1983); Joshi et al., J. Biol. Chem., 265: 14518-14525 (1990); Zarling et al., J. Immunol., 124: 913-920 (1980); Bouizar et al, Eur. J. Biochem., 155: 141-147 (1986); Park et al., J. Biol. Chem., 261: 205-210 (1986); Browning et al., J. Immunol., 143: 1859-1867 (1989). Moreover a broad range of cleavable, bifunctional (both homo- and heterobifunctional) spacer arms are commercially available. An exemplary cleavable group, an ester, is cleavable group that may be cleaved by a reagent, e.g. sodium hydroxide, resulting in a carboxylate-containing fragment and a hydroxyl-containing product.

The term "nucleic acid polymer" as used herein refers to a deoxyribonucleotide or ribonucleotide polymer in either single- or double-stranded form, including DNA and RNA, and unless otherwise stated encompasses nucleic acid-like structures with synthetic backbones, as well as amplification products. In the context of the present invention, a nucleic acid polymer may be an isolated molecule, present in an amplification reaction or present in a hybridization reaction.

As used herein, the term "nucleotide analogue" refers to a molecule that is structurally similar to a natural nucleotide and that can function in a similar manner as the naturally occurring nucleotide (e.g., exhibits similar ability to base pair with one of the naturally occurring bases). The term "nucleoside analogue", as used herein, refers to a molecule that is structurally similar to a natural nucleoside and that can function in a similar manner as the naturally occurring nucleoside (e.g., exhibits similar ability to be incorporated into DNA by DNA replication). The term "nucleotide" refers to a monomeric unit of DNA or RNA containing a sugar moiety (pentose), a phosphate or polyphosphate and a nitrogenous heterocyclic base. The base is linked to the sugar moiety via the glycosidic carbon (i.e., the 1'-carbon of the pentose) and that combination of base and sugar is called a "nucleoside". The base characterizes the nucleotide (or nucleoside) with the four bases of DNA being adenine (or A), guanine (G), cytosine (C) and thymine (T), and the four bases of RNA being adenine, guanine, cytosine, and uracil (U). In certain embodiments of the present invention a nucleotide analogue (or nucleoside analogue) comprises a chemical handle and as used herein also referred to as "modified nucleotides" or "modified nucleic acid polymers".

The term "reactive group" as used herein refers to a group that is capable of reacting with another chemical group to form a covalent bond, i.e. is covalently reactive under suitable reaction conditions, and generally represents a point of attachment for another substance. As used herein, reactive groups refer to chemical moieties generally found in biological systems and that react under normal biological conditions, these are herein distinguished from the chemical handle, defined above, the azido and activated alkyne moieties of the present invention. As referred to herein the reactive group is a moiety, such as carboxylic acid or succinimidyl ester, that is capable of chemically reacting with a functional group on a different compound to form a covalent linkage. Reactive groups generally include nucleophiles, electrophiles and photoactivatable groups.

The term "reporter molecule" refers to any moiety capable of being attached to a carrier molecule or solid support, such as a modified nucleotide or nucleic acid polymer, and detected either directly or indirectly. Reporter molecules include, without limitation, a chromophore, a fluorophore, a fluorescent protein, a phosphorescent dye, a tandem dye, a particle, a hapten, an enzyme and a radioisotope. Preferred reporter molecules include fluorophores, fluorescent proteins, haptens, and enzymes.

The term "sample" as used herein refers to any material that may contain an analyte for detection or quantification or a modified nucleotide or nucleic acid polymer. The analyte may include a reactive group, e.g., a group through which a compound of the invention can be conjugated to the analyte. The sample may also include diluents, buffers, detergents, and contaminating species, debris and the like that are found mixed with the target. Illustrative examples include urine, sera, blood plasma, total blood, saliva, tear fluid, cerebrospinal fluid, secretory fluids from nipples and the like. Also included are solid, gel or sol substances such as mucus, body tissues, cells and the like suspended or dissolved in liquid materials such as buffers, extractants, solvents and the like. Typically, the sample is a live cell, a biological fluid that comprises endogenous host cell proteins, nucleic acid polymers, nucleotides, oligonucleotides, peptides and buffer solutions. The sample may be in an aqueous solution, a viable cell culture or immobilized on a solid or semi solid surface such as a polyacrylamide gel, membrane blot or on a microarray.

The term "solid support," as used herein, refers to a material that is substantially insoluble in a selected solvent system, or which can be readily separated (e.g., by precipitation) from a selected solvent system in which it is soluble. Solid supports useful in practicing the present invention can include groups that are activated or capable of activation to allow selected one or more compounds described herein to be bound to the solid support.

The term "Staudinger ligation" as used herein refers to a chemical reaction developed by Saxon and Bertozzi (E. Saxon and C. Bertozzi, Science, 2000, 287: 2007-2010) that is a modification of the classical Staudinger reaction. The classical Staudinger reaction is a chemical reaction in which the combination of an azide with a phosphine or phosphite produces an aza-ylide intermediate, which upon hydrolysis yields a phosphine oxide and an amine. A Staudinger reaction is a mild method of reducing an azide to an amine; and triphenylphosphine is commonly used as the reducing agent. In a Staudinger ligation, an electrophilic trap (usually a methyl ester) is appropriately placed on a triarylphosphine aryl group (usually ortho to the phosphorus atom) and reacted with the azide, to yield an aza-ylide intermediate, which rearranges in aqueous media to produce a compound with amide group and a phosphine oxide function. The Staudinger ligation is so named because it ligates (attaches/covalently links) the two starting molecules together, whereas in the classical Staudinger reaction, the two products are not covalently linked after hydrolysis.

The terms "structural integrity of the [nucleic acid] is not reduced" or "preservation of the structural integrity of the [nucleic acid]", as used herein, means that either: 1) when analyzed by gel electrophoresis and detection (such as staining), a band or spot arising from the labeled nucleic acid is not reduced in intensity by more than 20%, and preferably not reduced by more than 10%, with respect to the corresponding band or spot arising from the same amount of the electrophoresed unlabeled nucleic acid, arising from the labeled nucleic acid analyzed; or 2) when analyzed by gel electrophoresis, a band or spot arising from the labeled nucleic acid is not observed to be significantly less sharp than the corresponding band or spot arising from the same amount of the electrophoresed unlabeled nucleic acid, where "significantly less sharp" (synonymous with "significantly more diffuse") means the detectable band or spot takes up at least 5% more, preferably 10% more, more preferably 20% more area on the gel than the corresponding unlabeled nucleic acid. Other reproducible tests for structural integrity of labeled nucleic acids include, without limitation detection of released amino acids or peptides, or mass spectrometry.

In general, for ease of understanding the present invention, the metabolic and enzymatic labeling of nucleic acids with azide moieties, alkyne moieties or phosphine, and the chemical labeling of such moieties with azide reactive moieties, alkyne reactive moieties or phosphine reactive moieties will first be described in detail. This will be followed by some embodiments in which such labeled nucleic acids can be detected, isolated and/or analyzed. Exemplified methods are then disclosed.

Labeling of Nucleic Acid Polymer Using [3+2] Cycloaddition

The nucleic acid polymers produced according to methods described herein, or utilized in methods described herein, are single- or double-stranded deoxyribonucleotide or ribonucleotide polymers. As will be appreciated by one of ordinary skill in the art, the nucleic acid polymers can be polynucleotides of any of a wide range of sizes including short oligonucleotides comprising at least about 8 nucleotides as well as full genomic DNA molecules.

Some of the labeling methods described herein generally include a [3+2] cycloaddition between a first reactive unsaturated group on a nucleotide incorporated into a nucleic acid polymer and a second reactive unsaturated group attached to a reporter molecule, a carrier molecule and/or a solid support. Thus, in one aspect the modified nucleic acid polymer comprises an azido group with reacts with an activated alkyne on a reporter molecule, a carrier molecule and/or a solid support to form a covalent bond. In another aspect the modified nucleic acid polymer comprises an activated alkynes that reacts with an azido moiety on reporter molecule, a carrier molecule and/or a solid support to form a covalent bond.

As described herein the tagging/labeling of nucleic acid polymers, also referred to herein as nucleic acids, utilize the incorporation of a bioorthoganol moieties into a nucleic acid polymer followed by chemical attachment of a label. The bioorthoganol moieties can be incorporated into a nucleic acid using in vitro extension and/or amplification techniques including but not limited to, polymerase chain reaction (PCR), ligation-based thermocycling approaches, reverse transcription-PCR, real-time PCR, linear amplification techniques and isothermal DNA amplification techniques such as, by way of example only, real-time strand displacement amplification (SDA), rolling-circle amplification (RCA), multiple-displacement amplification (MDA), Q-beta replicase amplification, automated Q-beta replicase amplification assay and other RNA polymerase mediated techniques such as, for example, nucleic acid sequence based amplification or NASBA and transcription mediated amplification (TMA). In certain embodiments, such bioorthoganol moieties are incorporated using telomerase based incorporation. These bioorthoganol moieties are non-native, non-perturbing chemical handles possessing unique chemical functionality that can be modified through highly selective reactions. Examples of such moieties includes, but is not limited to hyrazide and aminooxy derivatives, azides that can be selectively modified with phosphines (Staudinger ligation), azides that can be selectively modified with activated alkynes, and azides that can be selectively modified with terminal alkynes ("click" chemistry). The nucleic acids in which such bioorthoganol moieties can be incorporated into include, but are not limited to, DNA, RNA and oligonucleotides.

In certain embodiments the isothermal DNA amplification technology using Helicase Dependent amplification is used to incorporate bioorthoganol moieties into a nucleic acid. Examples of such Helicase Dependent amplification include
(a) mHDA technology which amplifies DNA at a single temperature (37° C.) by utilizing the unwinding activity of a DNA Helicase and a DNA synthesis activity of a DNA polymerase;
(b) tHDA technology which amplifies DNA at a single temperature (65° C.) by utilizing the unwinding activity of a thermo tolerant DNA Helicase and a DNA synthesis activity of Bst DNA polymerase (from *Bacillus stearoethermophillus*);
(c) circular HDA in which DNA amplification uses T7 Helicase and T7DNA polymerase and is similar to rolling circle DNA amplification. Other accessory proteins in this platform include T7 single strand DNA binding protein. This platform can be used for in vitro amplification of plasmid or covalent closed circular DNA. This technology has significant use in clinical diagnostics and molecular biology e.g., in DNA sequencing and mutagenesis, and
d) rt-HDA takes advantage of the reverse transcriptase activity of reverse transcriptase under constant temperature conditions combined with polymerase activity of Bst polymerase.

In certain embodiments the isothermal DNA amplification technology Strand Displacement Amplification (SDA) is used to incorporate bioorthoganol moieties into a nucleic acid. In SDA a primer contains a restriction site is annealed to template. Amplification primers are then annealed to 5' adjacent sequences (form a nick) and start amplification at a fixed temperature. Newly synthesized DNA are nicked by a restriction enzyme, polymerase starts amplification again, displacing the newly synthesized strands. $10^9$ copies of DNA can be made in one reaction.

In certain embodiments the isothermal DNA amplification technology Loop mediated Isothermal DNA amplification is used to incorporate bioorthoganol moieties into a nucleic acid. Loop-mediated Isothermal Amplification (LAMP) uses 4 primers, which recognize 6 distinct regions on the target gene and a DNA polymerase with strand displacement activity to carry out reaction under isothermal condition. Amplification and detection of gene can be completed in a single step, by incubating the mixture of samples, primers, DNA polymerase with strand displacement activity and substrate at a constant temperature between 60-65° C. It provides high amplification efficiency, with DNA being amplified 109-1010 times in 15-60 minutes. Because of its high specificity, the presence of amplified product can indicate the presence of target gene. LAMP also uses Bst DNA polymerase.

Incertain embodiments, rolling circle DNA amplification/Phi29 based DNA whole genome (or partial genome) amplification is used to incorporate bioorthoganol moieties into a nucleic acid. This method uses phi 29 DNA polymerase and can amplify DNA (Linear or circular) with high fidelity and efficiency. Such amplification methods can be use for the preparation of DNA probes from in situ hybridizations.

Nucleic acid polymers containing at least one nucleotide analogue may be alternatively be prepared by any of a variety of methods well known in the art including synthetic and enzymatic methods (J. Sambrook et al., "*Molecular Cloning: A Laboratory Manual*", 1989, $2^{nd}$ Ed., Cold Spring Harbour Laboratory Press: New York, N.Y.; "*PCR Protocols: A Guide to Methods and Applications*", 1990, M. A. Innis (Ed.), Academic Press: New York, N.Y.; P. Tijssen "*Hybridization with Nucleic Acid Probes—Laboratory Techniques in Biochemistry and Molecular Biology (Parts I and II)*", 1993, Elsevier Science; "*PCR Strategies*", 1995, M. A. Innis (Ed.), Academic Press: New York, N.Y.; and "*Short Protocols in Molecular Biology*", 2002, F. M. Ausubel (Ed.), 5 th Ed., John Wiley & Sons: Secaucus, N.J.).

Nucleic acids used in the methods described herein may be prepared using automated, solid-phase procedure based on the phosphoramidite approach. In such a method, each nucleotide (including nucleotide analogues) is individually added to the 5'-end of the growing polynucleotide chain, which is attached at the 3'-end to a solid support. The added nucleotides are in the form of trivalent 3'-phosphoramidites that are protected from polymerization by a dimethoxytriyl (or DMT) group at the 5'-position. After base-induced phosphoramidite coupling, mild oxidation to give a pentavalent phosphotriester intermediate, DMT removal provides a new site for polynucleotide elongation. The nucleic acid polymers are then cleaved off the solid support, and the phosphodiester and exocyclic amino groups are deprotected with ammonium hydroxide. These syntheses may be performed on oligo synthesizers such as those commercially available from Perkin Elmer/Applied Biosystems, Inc (Foster City, Calif.), DuPont (Wilmington, Del.) or Milligen (Bedford, Mass.).

As will be appreciated by one of ordinary skill in the art, nucleic acid polymers of the described herein may be prepared either by a pre-synthetic modification method (i.e., incorporation of nucleotides analogues into the nucleic acid molecule) or a post-synthetic modification method (i.e., modification of naturally occurring nucleotides to nucleotide analogues in the nucleic acid molecule). Alternatively, nucleotide analogues can be incorporated into the DNA of cells or living systems by DNA replication, or into RNA by reaction, as described below.

Thus, in certain embodiments are provided methods for making modified nucleic acid polymers and the polymers themselves.

In one aspect is a method for making an azido, alkyne or phosphine modified nucleic acid polymer, wherein the method comprises:
incubating at least one azido, alkyne or phosphine modified nucleotide in the presence of a nucleic acid amplification enzyme to form an azido, alkyne or phosphine modified nucleic acid polymer.

In one aspect, the nucleic acid enzyme is a DNA polymerase and in another aspect the nucleic acid enzyme is a RNA polymerase. We have unexpectedly found that incorporation of azido modified nucleotides into a nucleic acid polymer increases the melting temperature of the polymer under hybridization conditions. Thus, any application wherein a probes could be utilized that has an increased melting temperature is envisioned in the present methods of using the modified nucleic acid polymers.

Isolation or purification of the nucleic acid polymers of the present invention, where necessary, may be carried out by any of a variety of methods well-known in the art. Purification of nucleic acid polymers is typically performed either by native acrylamide gel electrophoresis, agarose electrophoresis or by size exclusion or by anion-exchange HPLC as described, for example by J. D. Pearson and F. E. Regnier (J. Chrom., 1983, 255: 137-149) or by reverse phase HPLC (G. D. McFarland and P. N. Borer, Nucleic Acids Res., 1979, 7: 1067-1080).

If desired, the sequence of synthetic nucleic acid polymers can be verified using any suitable sequencing method including, but not limited to, chemical degradation (A. M. Maxam and W. Gilbert, Methods of Enzymology, 1980, 65: 499-560), matrix-assisted laser desorption ionization time-of-flight (MALDI-TOF) mass spectrometry (U. Pieles et al., Nucleic Acids Res., 1993, 21: 3191-3196), mass spectrometry following alkaline phosphatase and exonuclease digestions (H. Wu and H. Aboleneen, Anal. Biochem., 2001, 290: 347-352), and the like.

Provided herein are methods and compositions for detection, isolation and/or analysis of labeled nucleic acids facilitated by the incorporation of nucleotides comprising azide moieties, alkyne moieties, or phosphine moieties. In particular, presented are a novel methods for A) amplification methods for incorporating a nucleotide comprising an azide moiety into a nucleic acid, B) labeling such azido modified nucleic acids in solution followed by separation using methods known in the art for separating nucleic acids, C) labeling immobilized modified nucleic acids and D) novel methods for telomerase based assays using such modified nucleic acids. In addition, these azide, activated alkyne or phosphine modified nucleic acids can form conjugates with reporter molecules, carrier molecules and/or solid supports using methods provided herein. The reporter molecules can include, but are not limited to labels, while the solid supports can include, but are not limited to, solid support resins, microtiter plates and microarray slides. The carrier molecules can include, but are not limited to, affinity tags, nucleotides, oligonucleotides and polymers. In certain embodiments, the nucleic acids are modified with alkyne containing nucleotides, and in other embodiments, the nucleic acids are modified with phosphine containing nucleotides.

Nucleoside and Nucleotide Analogues

Nucleoside analogues (or nucleotide analogues) suitable for use in the methods described herein include any nucleoside analogue (or nucleotide analogue), as defined herein, that contains a reactive bioorthoganol moiety that can undergo a [3+2] cycloaddition or Staudinger ligation. In some embodiments, the reactive bioorthoganol moiety is carried by the base of the nucleoside (or nucleotide). The base carrying the reactive bioorthoganol moiety can be a purine (e.g., adenine or guanine) or a pyrimidine (e.g., cytosine, uracil or thymine). In certain embodiments, the base is uracil; in some such embodiments, uracil carries the reactive bioorthoganol moiety on the 5-position. In certain embodiments, the base is adenine; in some such embodiments, adenine carries the reactive bioorthoganol moiety. In certain embodiments, the bioorthoganol moiety is indirectly attached to the base, while in other embodiments the bioorthoganol moiety is directly covalently attached to the base. Non-limiting examples of the nucleoside analogues that may be used in the methods described herein include 5-ethynyl-2'deoxyuracil (also termed herein ethynyluracil or EdU) and 5-azido-2'-deoxyuracil (also termed herein azidouracil or AdU) as well as their triphosphate and phosphoramidite forms. EdU can be synthesized essentially as described by C.-S. Yu and F. Oberdorfer, Synlett, 2000, 1: 86-88; and AdU can be synthesized using a method similar to that described in P. Sunthankar et al., Anal. Biochem., 1998, 258: 195-201 to synthesize azido-dUMP. EdU is also commercially available from Berry and Associates, Inc. (Dexter, Mich.).

In certain embodiments, the reactive bioorthoganol moiety is carried by the sugar (ribose and deoxyribose) of the nucleoside (or nucleotide). In certain embodiments, the bioorthoganol moiety is indirectly attached to the sugar, while in other embodiments the bioorthoganol moiety is directly covalently attached to the sugar. In certain embodiments, the nucleotide is a nucleotide monophosphate with the reactive bioorthoganol moiety attached to the phosphate moiety. In certain embodiments, the nucleotide is a nucleotide diphosphate with the reactive bioorthoganol moiety attached to the terminal phosphate moiety. In certain embodiments, the nucleotide is a nucleotide triphosphate with the reactive bioorthoganol moiety attached to the terminal phosphate moiety. The sugar carrying the reactive bioorthoganol moiety can covalently attached to a purine (e.g., adenine or guanine) or a pyrimidine (e.g., cytosine, uracil or thymine). In certain embodiments, the base is uracil, while in other embodiments the base is adenine. Non-limiting examples of the nucleotide triphosphate analogues that may be used in the methods described herein (see FIG. 1) include $N_3$-dATP (azide-dATP), $N_3$-dUTP (azide-dUTP), $N_3$-dTTP, $N_3$-dGTP, $N_3$-dCTP, E-dATP (ethynyl-dATP) and E-dUTP (ethynyl-dUTP), E-dGTP, E-dCTP, E-dTTP.

The reactive bioorthoganol moiety can be a 1,3-dipole such as a nitrile oxide, an azide, a diazomethane, a nitrone or a nitrile imine. In certain embodiments, the 1,3-dipole is an azide. Alternatively, the reactive bioorthoganol moiety can be a dipolarophile such as an alkene (e.g., vinyl, propylene, and the like) or an alkyne (e.g., ethynyl, propynyl, and the like). In certain embodiments, the dipolarophile is an alkyne, such as, for example, an ethynyl group.

Figure 2:
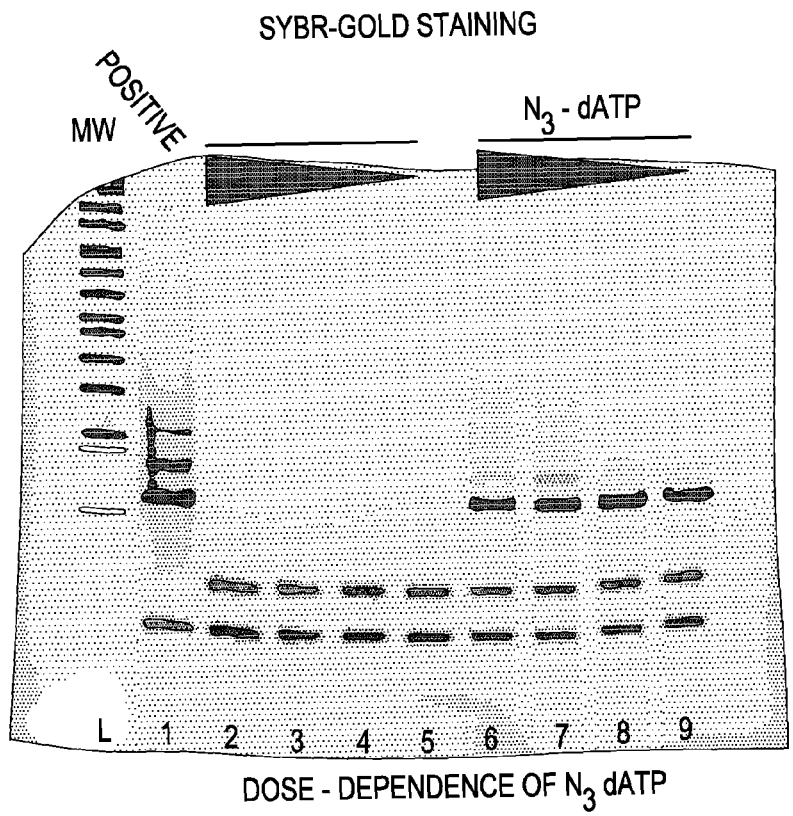

Chemical Modification of Nucleic Acids Containing Azide, Alkyne or Phosphine Moieties The nucleic acids that can be chemically modified using the methods described herein contain azide moieties, alkyne moieties or phosphine moieties that are incorporated into nucleic acids using various amplification techniques utilizing nucleobases that contain azide moieties, alkyne moieties or phosphine moieties. Such nucleobases have been chemical synthesized as described herein. These azide moieties, alkyne moieties and phosphine moieties are non-native, non-perturbing bioorthoganol chemical moieties that possess unique chemical functionality that can be modified through highly selective reactions. Non-limiting examples of such reactions used in the methods described herein are shown in FIG. 2, wherein the chemical labeling of nucleic acids that contain azide moieties or alkyne moieties utilize Copper(I)-catalyzed Azide-Alkyne Cycloaddition, also referred to herein as "click" chemistry, the chemical labeling of nucleic acids that contain azide moieties or phosphine moieties utilize Staudinger ligation, and the chemical labeling of nucleic acids that contain activated-alkyne moieties or activated-alkyne reactive moieties.

"Click" Chemistry

Azides and terminal or internal alkynes can undergo a 1,3-dipolar cycloaddition (Huisgen cycloaddition) reaction to give a 1,2,3-triazole. However, this reaction requires long reaction times and elevated temperatures. Alternatively, azides and terminal alkynes can undergo Copper(I)-catalyzed Azide-Alkyne Cycloaddition (CuAAC) at room temperature. Such copper(I)-catalyzed azide-alkyne cycloadditions, also known as "click" chemistry, is a variant of the Huisgen 1,3-dipolar cycloaddition wherein organic azides and terminal alkynes react to give 1,4-regioisomers of 1,2,3-triazoles. Examples of "click" chemistry reactions are described by Sharpless et al. (U.S. Patent Application Publication No. 20050222427, published Oct. 6, 2005, PCT/US03/17311; Lewis W G, et al., Angewandte Chemie-Int'l Ed. 41 (6): 1053; method reviewed in Kolb, H. C., et al., Angew. Chem. Inst. Ed. 2001, 40:2004-2021), which developed reagents that react with each other in high yield and with few side reactions in a heteroatom linkage (as opposed to carbon-carbon bonds) in order to create libraries of chemical compounds. As described herein, "click" chemistry is used in the methods for labeling nucleic acids.

The copper used as a catalyst for the "click chemistry reaction used in the methods described herein to conjugate a label (reporter group, solid support or carrier molecule) to a nucleic acid is in the Cu (I) reduction state. The sources of copper(I) used in such copper(I)-catalyzed azide-alkyne cycloadditions can be any cuprous salt including, but not limited to, cuprous halides such as cuprous bromide or cuprous iodide. However, this regioselective cycloaddition can also be conducted in the presence of a metal catalyst and a reducing agent. In certain embodiments, copper can be provided in the Cu (II) reduction state (for example, as a salt, such as but not limited to $Cu(NO_3)_2$ $Cu(OAc)_2$ or $CuSO_4$), in the presence of a reducing agent wherein Cu(I) is formed in situ by the reduction of Cu(II). Such reducing agents include, but are not limited to, ascorbate, Tris(2-Carboxyethyl) Phosphine (TCEP), 2,4,6-trichlorophenol (TCP), NADH, NADPH, thiosulfate, metallic copper, quinone, hydroquinone, vitamin $K_1$, glutathione, cysteine, 2-mercaptoethanol, dithiothreitol, $Fe^{2+}$, $Co^{2+}$, or an applied electric potential. In other embodiments, the reducing agents include metals selected from Al, Be, Co, Cr, Fe, Mg, Mn, Ni, Zn, Au, Ag, Hg, Cd, Zr, Ru, Fe, Co, Pt, Pd, Ni, Rh, and W.

The copper(I)-catalyzed azide-alkyne cycloadditions for labeling nucleic acids can be performed in water and a variety of solvents, including mixtures of water and a variety of (partially) miscible organic solvents including alcohols, dimethyl sulfoxide (DMSO), dimethyl formamide (DMF), tert-butanol (tBuOH) and acetone.

Without limitation to any particular mechanism, copper in the Cu (I) state is a preferred catalyst for the copper(I)-catalyzed azide-alkyne cycloadditions, or "click" chemistry reactions, used in the methods described herein. Certain metal ions are unstable in aqueous solvents, by way of example Cu(I), therefore stabilizing ligands/chelators can be used to improve the reaction. In certain embodiments at least one copper chelator is used in the methods described herein, wherein such chelators binds copper in the Cu (I) state. In certain embodiments at least one copper chelator is used in the methods described herein, wherein such chelators binds copper in the Cu (II) state. In certain embodiments, the copper (I) chelator is a 1,10 phenanthroline-containing copper (I) chelator. Non-limiting examples of such phenanthroline-containing copper (I) chelators include, but are not limited to, bathophenanthroline disulfonic acid (4,7-diphenyl-1,10-phenanthroline disulfonic acid) and bathocuproine disulfonic acid (BCS; 2,9-dimethyl-4,7-diphenyl-1,10-phenanthroline disulfonate). Other chelators used in such methods include, but are not limited to, N-(2-acetamido)iminodiacetic acid (ADA), pyridine-2,6-dicarboxylic acid (PDA), S-carboxymethyl-L-cysteine (SCMC), trientine, tetra-ethylenepolyamine (TEPA), NNNN-tetrakis(2-pyridylmethyl)ethylenediamine (TPEN), EDTA, neocuproine, N-(2-acetamido)iminodiacetic acid (ADA), pyridine-2,6-dicarboxylic acid (PDA), S-carboxymethyl-L-cysteine (SCMC), tris-(benzyl-triazolylmethyl)amine (TBTA), or a derivative thereof. Most metal chelators, a wide variety of which are known in the chemical, biochemical, and medical arts, are known to chelate several metals, and thus metal chelators in general can be tested for their function in 1,3 cycloaddition reactions catalyzed by copper. In certain embodiments, histidine is used as a chelator, while in other embodiments glutathione is used as a chelator and a reducing agent.

The concentration of the reducing agents used in the "click" chemistry reaction described herein can be in the micromolar to millimolar range. In certain embodiments the concentration of the reducing agent is from about 100 micromolar to about 100 millimolar. In other embodiments the concentration of the reducing agent is from about 10 micromolar to about 10 millimolar. In other embodiments the concentration of the reducing agent is from about 1 micromolar to about 1 millimolar.

In certain embodiments, the methods describe herein for labeling nucleic acids using "click" chemistry, at least one copper chelator is added after copper(II) used in the reaction has been contacted with a reducing agent. In other embodiments, at least one copper chelator can be added immediately after contacting copper(II) with a reducing agent. In other embodiments, the copper chelator(s) is added between about five seconds and about twenty-four hours after copper(II) and a reducing agent have been combined in a reaction mixture. In other embodiments, at least one copper chelator can be added any time to a reaction mixture that includes copper(II) and a reducing agent, such as, by way of example only, immediately after contacting copper(II) and a reducing agent, or within about five minutes of contacting copper(II) and a reducing agent in the reaction mixture. In some embodiments, at least one copper chelator can be added between about five seconds and about one hour, between about one minute and about thirty minutes, between about five minutes and about one hour, between about thirty minutes and about two hours, between about one hour and about twenty-four hours, between about one hour and about five hours, between about two hours and about eight hours, after copper(II) and a reducing agent have been combined for use in a reaction mixture.

In other embodiments, one or more copper chelators can be added more than once to such "click" chemistry reactions. In embodiments in which more than one copper chelator is added to a reaction, two or more of the copper chelators can bind copper in the Cu (I) state or, one or more of the copper chelators can bind copper in the Cu (I) state and one or more additional chelators can bind copper in the Cu (II) state. In certain embodiments, one or more copper chelators can be added after the initial addition of a copper chelator to the "click" chemistry reaction. In certain embodiments, the one or more copper chelators added after the initial addition of a copper chelator to the reaction can be the same or different from a copper chelator added at an earlier time to the reaction.

The concentration of a copper chelator used in the "click" chemistry reaction described herein can be determined and optimized using methods well known in the art, including those disclosed herein using "click" chemistry to label nucleic acids followed by detecting such labeled nucleic acids to determine the efficiency of the labeling reaction and the integrity of the labeled nucleic acid(s). In certain embodiments, the chelator concentrations used in the methods described herein is in the micromolar to millimolar range, by way of example only, from 1 micromolar to 100 millimolar. In certain embodiments the chelator concentration is from about 10 micromolar to about 10 millimolar. In other embodiments the chelator concentration is from about 50 micromolar to about 10 millimolar. In other embodiments the chelator, can be provided in a solution that includes a water miscible solvent such as, alcohols, dimethyl sulfoxide (DMSO), dimethyl formamide (DMF), tert-butanol (tBuOH) and acetone. In other embodiments the chelator, can be provided in a solution that includes a solvent such as, for example, dimethyl sulfoxide (DMSO) or dimethylformamide (DMF).

In certain embodiments of the methods for labeling nucleic acids utilizing "click" chemistry described herein, the nucleic acid can possess an azide moiety, whereupon the label possesses an alkyne moiety, whereas in other embodiments the nucleic acid can possess an alkyne moiety, and the label possesses an azide moiety.

In certain embodiments are provided methods for forming a modified nucleic acid polymer conjugate, wherein the method comprises:

incorporating an azide modified nucleotide into the nucleic acid polymer by contacting the azide modified nucleotide with at least one other nucleotide in the presence of a DNA amplification enzyme to form an azide modified nucleic acid polymer; and contacting the azide modified nucleic acid polymer with a reporter molecule, carrier molecule or solid support that comprises an activated or terminal alkyne or phosphine moiety to form a nucleic acid polymer-reporter molecule, carrier molecule, solid support conjugate.

In an alternative embodiment are provided methods for forming a modified nucleic acid polymer conjugate, wherein the method comprises:

incorporating a terminal alkyne modified nucleotide into the nucleic acid polymer by contacting the terminal alkyne modified nucleotide with at least one other nucleotide in the presence of a DNA amplification enzyme to form a terminal alkyne modified nucleic acid polymer; and contacting the terminal alkyne modified nucleic acid polymer with a reporter molecule, carrier molecule or solid support that comprises an azido moiety to form a nucleic acid polymer-reporter molecule, carrier molecule, solid support conjugate.

Staudinger Ligation

The Staudinger reaction, which involves reaction between trivalent phosphorous compounds and organic azides (Staudinger et al. Helv. Chim. Acta 1919, 2, 635), has been used for a multitude of applications. (Gololobov et al. Tetrahedron 1980, 37, 437); (Gololobov et al. Tetrahedron 1992, 48, 1353). There are almost no restrictions on the nature of the two reactants. The Staudinger ligation is a modification of the Staudinger reaction in which an electrophilic trap (usually a methyl ester) is placed on a triaryl phosphine. In the Staudinger ligation, the aza-ylide intermediate rearranges, in aqueous media, to produce an amide linkage and the phosphine oxide, ligating the two molecules together, whereas in the Staudinger reaction the two products are not covalently linked after hydrolysis. Such ligations have been described in U.S. Patent Application No. 20060276658. In certain embodiments, the phosphine can have a neighboring acyl group such as an ester, thioester or N-acyl imidazole (i.e. a phosphinoester, phosphinothioester, phosphinoimidazole) to trap the aza-ylide intermediate and form a stable amide bond upon hydrolysis. In certain embodiments, the phosphine can be a di- or triarylphosphine to stabilize the phosphine. The phosphines used in the Staudinger ligation methods described herein to conjugate a label to a nucleic acid include, but are not limited to, cyclic or acyclic, halogenated, bisphosphorus, or even polymeric. Similarly, the azides can be alkyl, aryl, acyl or phosphoryl. In certain embodiments, such ligations are carried out under oxygen-free anhydrous conditions.

In certain embodiments of the methods for labeling nucleic acid utilizing Staudinger ligation described herein, the nucleic acid can possess an azide moiety, whereupon the label possesses a phosphine moiety, whereas in other embodiments the nucleic acid can possess a phosphine moiety, and the label possesses an azide moiety.

In certain embodiments are provided methods for forming a modified nucleic acid polymer conjugate, wherein the methods comprises:

incorporating a phosphine modified nucleotide into the nucleic acid polymer by contacting the phosphine modified nucleotide with at least one other nucleotide in the presence of a DNA amplification enzyme to form a phosphine modified nucleic acid polymer; and contacting the phosphine modified nucleic acid polymer with a reporter molecule, carrier molecule or solid support that comprises an azido moiety to form a nucleic acid polymer-reporter molecule, carrier molecule, solid support conjugate.

Activated-Alkyne Chemistry

Azides and alkynes can undergo catalyst-free [3+2] cycloaddition by a using the reaction of activated alkynes with azides. Such catalyst free [3+2] cycloaddition can be used in methods described herein to conjugate a label (reporter molecule, solid support or carrier molecule) to a nucleic acid. Alkynes can be activated by ring strain such as, by way of example only, eight membered ring structures, appending electron-withdrawing groups to such alkyne rings, or alkynes can be activated by the addition of a Lewis acid such as, by way of example only, Au(I) or Au(III).

In certain embodiments of the methods for labeling nucleic acids utilizing activated alkynes described herein, the nucleic acid can possess an azide moiety, whereupon the label possesses an activated alkyne moiety, whereas in other embodiments the nucleic acid can possess an activated alkyne moiety, and the label possesses an azide moiety.

After nucleic acids have been modified with azide moieties, alkyne moieties or phosphine moieties, they can be reacted under appropriate conditions to form conjugates with reporter molecules, solid supports or carrier molecules. In the methods and compositions described herein the azide moiety, alkyne moiety or phosphine moiety is used as a reactive functional group or chemical handle on the modified nucleic acid wherein an azide reactive moiety on a reporter molecule, a solid support or a carrier molecule, or an alkyne reactive moiety on a reporter molecule, a solid support or a carrier molecule, or a phosphine reactive moiety on a reporter molecule, a solid support or a carrier molecule is reacted with the modified nucleic acid to form a covalent conjugate comprising the nucleic acid and at least one reporter molecule, at least one solid support and/or at least one carrier molecule.

In certain embodiments, two azide-reactive groups are used to label nucleic acids: the first is an alkyne moiety used in a "click" chemistry reaction, and the second is a phosphine, such as a triarylphosphine, used in a Staudinger ligation. In one embodiment, "click" chemistry is utilized to form a conjugate with a nucleic acid polymer containing an azide moiety and a reporter molecule, solid support or carrier molecule, wherein the reporter molecule, solid support and carrier molecule contain an alkyne moiety. In another embodiment, "click" chemistry is utilized to form a conjugate with a nucleic acid polymer containing an alkyne moiety and a reporter molecule, solid support and/or carrier molecule, wherein the reporter molecule, solid support and carrier molecule contain an azide moiety. In another embodiment, a Staudinger ligation is utilized to form a conjugate with a nucleic acid polymer containing an azide moiety and a reporter molecule, solid support and/or carrier molecule, wherein the reporter molecule, solid support and carrier molecule contain an triaryl phosphine moiety. In another embodiment, a Staudinger ligation is utilized to form a conjugate with a nucleic acid polymer containing a triaryl phosphine moiety and a reporter molecule, solid support and/or carrier molecule, wherein the reporter molecule, solid support and carrier molecule contain an azide moiety. The methods described herein are not intended to be limited to these two azide-reactive groups, or chemical reactions, but it is envisioned that any chemical reaction utilizing an azide-reactive group attached to a reporter molecule, solid support or carrier molecule can be used with the azide, alkyne or phosphine modified nucleic acid polymers described herein.

In certain embodiments are provided methods for forming a modified nucleic acid polymer conjugate, wherein the method comprises:

incorporating an azide modified nucleotide into the nucleic acid polymer by contacting the azide modified nucleotide with at least one other nucleotide in the presence of a DNA amplification enzyme to form an azide modified nucleic acid polymer; and contacting the azide modified nucleic acid polymer with a reporter molecule, carrier molecule or solid support that comprises an activated or terminal alkyne or phosphine moiety to form a nucleic acid polymer-reporter molecule, carrier molecule, solid support conjugate.

In an alternative embodiment are provided methods for forming a modified nucleic acid polymer conjugate, wherein the method comprises:

incorporating a terminal alkyne modified nucleotide into the nucleic acid polymer by contacting the terminal alkyne modified nucleotide with at least one other nucleotide in the presence of a DNA amplification enzyme to form a terminal alkyne modified nucleic acid polymer; and contacting the terminal alkyne modified nucleic acid polymer with a reporter molecule, carrier molecule or solid support that comprises an azido moiety to form a nucleic acid polymer-reporter molecule, carrier molecule, solid support conjugate.

The methods, as described herein, that utilize cycloaddition reactions to label nucleic acids can be carried out at room temperature in aqueous conditions with excellent regioselectivity by the addition of catalytic amounts of Cu(I) salts to the reaction mixture. See, e.g., Tomoe, et al., (2002) *Org. Chem.* 67:3057-3064; and, Rostovtsev, et al., (2002) *Angew. Chem. Int. Ed.* 41:2596-2599. The resulting five-membered ring resulting from "click" chemistry cycloaddition is not generally reversible in reducing environments and is stable against hydrolysis for extended periods in aqueous environments. Thus, nucleic acids attached to a labeling agent, a detection agent, a reporter molecule, a solid support or a carrier molecule via such five-membered ring are stable.

The reporter molecules, solid supports and carrier molecules used in the methods and compositions described herein, can contain at least one alkyne moiety or at least one phosphine moiety capable of reacting with an azide moiety. The reporter molecules, solid supports and carrier molecules used in the methods and compositions described herein, can contain at least one azide moiety capable of reacting with an alkyne moiety or a phosphine moiety. The reporter molecules, solid supports and carrier molecules used in the methods and compositions described herein, can contain at least one phosphine moiety capable of reacting with an azide moiety. In certain embodiments, the phosphine moieties of the reporter molecules solid supports and carrier molecules described herein are triarylphosphine moieties.

In certain embodiments, the reporter molecules used in the methods and compositions described herein can include, but are not limited to labels, while the solid supports can include, but are not limited to, solid support resins, microtiter plates and microarray slides. The carrier molecules can include, but are not limited to, affinity tags, nucleotides, oligonucleotides and polymers.

Reporter Molecules

The reporter molecules used in the methods and compositions provided herein include any directly or indirectly detectable reporter molecule known by one skilled in the art that can be covalently attached to a modified nucleic acid described herein. In certain embodiments, the reporter molecules used in the methods and compositions provided herein include any directly or indirectly detectable reporter molecule known by one skilled in the art that can be covalently attached to an azide modified nucleic acid, an alkyne modified nucleic acid or a phosphine modified nucleic acid.

Reporter molecules used in the methods and compositions described herein can contain, but are not limited to, a chromophore, a fluorophore, a fluorescent protein, a phosphorescent dye, a tandem dye, a particle, a hapten, an enzyme and a radioisotope. In certain embodiments, such reporter molecules include fluorophores, fluorescent proteins, haptens, and enzymes.

A fluorophore used in reporter molecule in the methods and compositions described herein, can contain one or more aromatic or heteroaromatic rings, that are optionally substituted one or more times by a variety of substituents, including without limitation, halogen, nitro, cyano, alkyl, perfluoroalkyl, alkoxy, alkenyl, alkynyl, cycloalkyl, arylalkyl, acyl, aryl or heteroaryl ring system, benzo, or other substituents typically present on fluorophores known in the art.

A fluorophore used in reporter molecule in the methods and compositions described herein, is any chemical moiety that exhibits an absorption maximum at wavelengths greater than 280 nm, and retains its spectral properties when covalently attached to a modified nucleotide such as, by way of example only, an azide, and alkyne or a phosphine. Fluorophores used as in reporter molecule in the methods and compositions described herein include, without limitation; a pyrene (including any of the corresponding derivative compounds disclosed in U.S. Pat. No. 5,132,432), an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine (including any corresponding compounds in U.S. Ser. Nos. 09/968,401 and 09/969,853), a carbocyanine (including any corresponding compounds in U.S. Ser. Nos. 09/557,275; 09/969,853 and 09/968,401; U.S. Pat. Nos. 4,981,977; 5,268, 486; 5,569,587; 5,569,766; 5,486,616; 5,627,027; 5,808,044; 5,877,310; 6,002,003; 6,004,536; 6,008,373; 6,043,025; 6,127,134; 6,130,094; 6,133,445; and publications WO 02/26891, WO 97/40104, WO 99/51702, WO 01/21624; EP 1 065 250 A1), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774,339; 5,187,288; 5,248,782; 5,274,113; and 5,433,896), a xanthene (including any corresponding compounds disclosed in U.S. Pat. Nos. 6,162,931; 6,130,101; 6,229,055; 6,339,392; 5,451,343 and U.S. Ser. No. 09/922,333), an oxazine (including any corresponding compounds disclosed in U.S. Pat. No. 4,714,763) or a benzoxazine, a carbazine (including any corresponding compounds disclosed in U.S. Pat. No. 4,810,636), a phenalenone, a coumarin (including an corresponding compounds disclosed in U.S. Pat. Nos. 5,696,157; 5,459,276; 5,501,980 and 5,830,912), a benzofuran (including an corresponding compounds disclosed in U.S. Pat. Nos. 4,603,209 and 4,849, 362) and benzphenalenone (including any corresponding compounds disclosed in U.S. Pat. No. 4,812,409) and derivatives thereof. As used herein, oxazines include resorufins (including any corresponding compounds disclosed in U.S. Pat. No. 5,242,805), aminooxazinones, diaminooxazines, and their benzo-substituted analogs.

Xanthene type fluorophores used in reporter molecule in the methods and compositions described herein include, but are not limited to, a fluorescein, a rhodol (including any corresponding compounds disclosed in U.S. Pat. Nos. 5,227,487 and 5,442,045), or a rhodamine (including any corresponding compounds in U.S. Pat. Nos. 5,798,276; 5,846,737; U.S. Ser. No. 09/129,015). As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945,171). In certain embodiments, the fluorophore is a xanthene that is bound via a linkage that is a single covalent bond at the 9-position of the xanthene. In other embodiments, the xanthenes include derivatives of 3H-xanthen-6-ol-3-one attached at the 9-position, derivatives of 6-amino-3H-xanthen-3-one attached at the 9-position, or derivatives of 6-amino-3H-xanthen-3-imine attached at the 9-position.

In certain embodiments, the fluorophores used in reporter molecules in the methods and compositions described herein include xanthene (rhodol, rhodamine, fluorescein and derivatives thereof) coumarin, cyanine, pyrene, oxazine and borapolyazaindacene. In other embodiments, such fluorophores are sulfonated xanthenes, fluorinated xanthenes, sulfonated coumarins, fluorinated coumarins and sulfonated cyanines.

Figure 3:
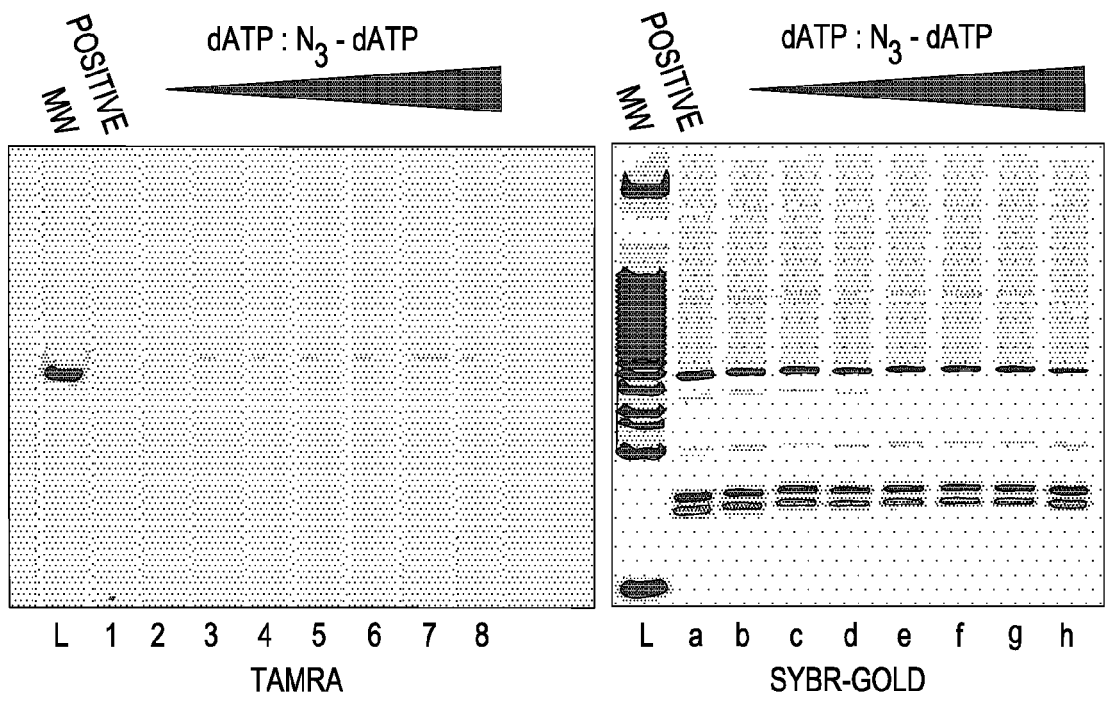

Non-limiting examples of the fluorophores used in reporter molecules in the methods and compositions described herein are shown in FIG. 3, wherein such fluorphores have been modified with azide moieties, alkyne moieties or phosphine moieties. In certain embodiments, the such fluorphores used in "click" chemistry reactions form triazole products wherein the conjugate does not requires UV excitation and any quenching effect due to conjugation of azido or alkyne groups to the fluorescent π-system is overcome.

The choice of the fluorophore attached to the modified nucleic acid will determine the absorption and fluorescence emission properties of the modified nucleic acid. Physical properties of a fluorophore label that can be used for detection of modified nucleic acids include, but are not limited to, spectral characteristics (absorption, emission and stokes shift), fluorescence intensity, lifetime, polarization and photo-bleaching rate, or combination thereof. All of these physical properties can be used to distinguish one fluorophore from another, and thereby allow for multiplexed analysis. In certain embodiments, the fluorophore has an absorption maximum at wavelengths greater than 480 nm. In other embodiments, the fluorophore absorbs at or near 488 nm to 514 nm (particularly suitable for excitation by the output of the argon-ion laser excitation source) or near 546 nm (particularly suitable for excitation by a mercury arc lamp). In other embodiment a fluorophore can emit in the NIR (near infra red region) for tissue or whole organism applications.

Many of fluorophores can also function as chromophores and thus the described fluorophores are also chromophores used in reporter molecules in the methods and compositions described herein.

In addition to fluorophores, enzymes also find use as labels for the detection reagents/reporter molecules used in the methods and compositions described herein. Enzymes are desirable labels because amplification of the detectable signal can be obtained resulting in increased assay sensitivity. The enzyme itself does not produce a detectable response but functions to break down a substrate when it is contacted by an appropriate substrate such that the converted substrate produces a fluorescent, calorimetric or luminescent signal. Enzymes amplify the detectable signal because one enzyme on a labeling reagent can result in multiple substrates being converted to a detectable signal. This is advantageous where there is a low quantity of target present in the sample or a fluorophore does not exist that will give comparable or stronger signal than the enzyme. However, fluorophores are most preferred because they do not require additional assay steps and thus reduce the overall time required to complete an assay. The enzyme substrate is selected to yield the preferred measurable product, e.g. calorimetric, fluorescent or chemiluminescence. Such substrates are extensively used in the art, many of which are described in the MOLECULAR PROBES HANDBOOK, supra.

In certain embodiments, calorimetric or fluorogenic substrate and enzyme combination use oxidoreductases such as, by way of example only, horseradish peroxidase and a substrate such as, by way of example only, 3,3'-diaminobenzidine (DAB) or 3-amino-9-ethylcarbazole (AEC), which yield a distinguishing color (brown and red, respectively). Other calorimetric oxidoreductase substrates used with the enzymatic reporter molecules described herein include, but are not limited to: 2,2-azino-bis(3-ethylbenzothiazoline-6-sulfonic acid) (ABTS), o-phenylenediamine (OPD), 3,3',5,5'-tetramethylbenzidine (TMB), o-dianisidine, 5-aminosalicylic acid, 4-chloro-1-naphthol. Fluorogenic substrates used with the enzymatic reporter molecules described herein include, but are not limited to, homovanillic acid or 4-hydroxy-3-methoxyphenylacetic acid, reduced phenoxazines and reduced benzothiazines, including Amplex® Red reagent and its variants (U.S. Pat. No. 4,384,042), Amplex UltraRed and its variants in (WO05042504) and reduced dihydroxanthenes, including dihydrofluoresceins (U.S. Pat. No. 6,162,931) and dihydrorhodamines including dihydrorhodamine 123. Peroxidase substrates can be used with the enzymatic reporter molecules described herein. Such peroxide substrates include, but are not limited to, tyramides (U.S. Pat. Nos. 5,196,306; 5,583,001 and 5,731,158) which represent a unique class of peroxidase substrates in that they can be intrinsically detectable before action of the enzyme but are "fixed in place" by the action of a peroxidase in the process described as tyramide signal amplification (TSA). These substrates are extensively utilized to label targets in samples that are cells, tissues or arrays for their subsequent detection by microscopy, flow cytometry, optical scanning and fluorometry.

In other embodiments the colorimetric (and in some cases fluorogenic) substrates and enzymes combination used in reporter molecules described herein include a phosphatase enzyme such as, by way of example only, an acid phosphatase, an alkaline phosphatase or a recombinant version of such a phosphatase. A colorimetric substrate used in combination with such phosphatases include, but are not limited to, 5-bromo-6-chloro-3-indolyl phosphate (BCIP), 6-chloro-3-indolyl phosphate, 5-bromo-6-chloro-3-indolyl phosphate, p-nitrophenyl phosphate, or o-nitrophenyl phosphate or with a fluorogenic substrate such as 4-methylumbelliferyl phosphate, 6,8-difluoro-7-hydroxy-4-methylcoumarinyl phosphate (DiFMUP, U.S. Pat. No. 5,830,912), fluorescein diphosphate, 3-O-methylfluorescein phosphate, resorufin phosphate, 9H-(1,3-dichloro-9,9-dimethylacridin-2-one-7-yl) phosphate (DDAO phosphate), or ELF 97, ELF 39 or related phosphates (U.S. Pat. Nos. 5,316,906 and 5,443,986).

Other enzymes used in reporter molecules described herein include glycosidases, including, but not limited to, beta-galactosidase, beta-glucuronidase and beta-glucosidase. The colorimetric substrates used with such enzymes include, but are not limited to, 5-bromo-4-chloro-3-indolyl beta-D-galactopyranoside (X-gal) and similar indolyl galactosides, glucosides, and glucuronides, o-nitrophenyl beta-D-galactopyranoside (ONPG) and p-nitrophenyl beta-D-galactopyranoside. Preferred fluorogenic substrates include resorufin beta-D-galactopyranoside, fluorescein digalactoside (FDG), fluorescein diglucuronide and their structural variants (U.S. Pat. Nos. 5,208,148; 5,242,805; 5,362,628; 5,576,424 and 5,773,236), 4-methylumbelliferyl beta-D-galactopyranoside, carboxyumbelliferyl beta-D-galactopyranoside and fluorinated coumarin beta-D-galactopyranosides (U.S. Pat. No. 5,830,912).

Additional enzymes used in reporter molecules described herein include, but are not limited to, hydrolases such as cholinesterases and peptidases, oxidases such as glucose oxidase and cytochrome oxidases, and reductases for which suitable substrates are known.

Enzymes and their appropriate substrates that produce chemiluminescence can also be used in reporter molecules described herein. Such enzymes include, but are not limited to, natural and recombinant forms of luciferases and aequorins. In addition, the chemiluminescence-producing substrates for phosphatases, glycosidases and oxidases such as those containing stable dioxetanes, luminol, isoluminol and acridinium esters an also be used in reporter molecules described herein.

In addition to enzymes, haptens can be used in label/reporter molecules described herein. In certain embodiments, such haptens include hormones, naturally occurring and synthetic drugs, pollutants, allergens, affector molecules, growth factors, chemokines, cytokines, lymphokines, amino acids, peptides, chemical intermediates, nucleotides, digoxin, biotin and the like. Biotin is useful because it can function in an enzyme system to further amplify the detectable signal, and it can function as a tag to be used in affinity chromatography for isolation purposes. For detection purposes, an enzyme conjugate that has affinity for biotin is used, such as, by way of example only, avidin-Horse Radish Peroxidase (HRP). Subsequently a peroxidase substrate as described herein can be added to produce a detectable signal.

Fluorescent proteins can also be used in label/reporter molecules described herein for use in the methods, compositions and modified nucleic acids described herein. Non-limiting examples of such fluorescent proteins include green fluorescent protein (GFP) and the phycobiliproteins and the derivatives thereof. The fluorescent proteins, especially phycobiliprotein, are particularly useful for creating tandem dye labeled modified nucleic acids. These tandem dyes comprise a fluorescent protein and a fluorophore for the purposes of obtaining a larger stokes shift wherein the emission spectra is farther shifted from the wavelength of the fluorescent protein's absorption spectra. This is particularly advantageous for detecting a low quantity of a target in a sample wherein the emitted fluorescent light is maximally optimized, in other words little to none of the emitted light is reabsorbed by the fluorescent protein. The fluorescent protein and fluorophore function as an energy transfer pair wherein the fluorescent protein emits at the wavelength that the fluorophore absorbs and the fluorophore then emits at a wavelength farther from the fluorescent proteins emission wavelength than could have been obtained with only the fluorescent protein. A particularly useful combination is the phycobiliproteins disclosed in U.S. Pat. Nos. 4,520,110; 4,859,582; 5,055,556 and the sulforhodamine fluorophores disclosed in 5,798,276, or the sulfonated cyanine fluorophores disclosed in U.S. Ser. Nos. 09/968/401 and 09/969/853; or the sulfonated xanthene derivatives disclosed in U.S. Pat. No. 6,130,101 and those combinations disclosed in U.S. Pat. No. 4,542,104. Alternatively, the fluorophore functions as the energy donor and the fluorescent protein is the energy acceptor.

Carrier Molecules Azide Reactive, Alkyne Reactive and Phosphine Reactive

In the methods and compositions described herein the modified nucleic acids can be conjugated to a carrier molecule. In certain embodiments, the modified nucleic acids contain at least one alkyne moiety or at least one phosphine moiety capable of reacting with a carrier molecule containing an azide moiety. In other embodiments, the modified nucleic acids contain at least one azide moiety capable of reacting with a carrier molecule containing an alkyne moiety or a phosphine moiety. In other embodiments, the modified nucleic acids contain at least one phosphine moiety capable of reacting with a carrier molecule containing an azide moiety. In certain embodiments, the phosphine moieties of the modified nucleic acids and carrier molecules are triaryl phosphine moieties.

A variety of carrier molecules can be used in the methods and compositions described herein, including, but not limited to, antigens, steroids, vitamins, drugs, haptens, metabolites, toxins, environmental pollutants, amino acids, peptides, proteins, nucleic acids, nucleic acid polymers, carbohydrates, lipids, and polymers. In certain embodiments, the carrier molecule contain an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus or combinations thereof.

In other embodiments, the carrier molecule is selected from a hapten, a nucleotide, an oligonucleotide, a nucleic acid polymer, a protein, a peptide or a polysaccharide. In still other embodiments, the carrier molecule is an amino acid, a peptide, a protein, a polysaccharide, a nucleoside, a nucleotide, an oligonucleotide, a nucleic acid, a hapten, a psoralen, a drug, a hormone, a lipid, a lipid assembly, a tyramine, a synthetic polymer, a polymeric microparticle, a biological cell, cellular components, an ion chelating moiety, an enzymatic substrate or a virus. In further embodiments, the carrier molecule is an antibody or fragment thereof, an antigen, an avidin or streptavidin, a biotin, a dextran, an IgG binding protein, a fluorescent protein, agarose, and a non-biological microparticle.

In certain embodiments wherein the carrier molecule is an enzymatic substrate, the enzymatic substrate is selected from an amino acid, a peptide, a sugar, an alcohol, alkanoic acid, 4-guanidinobenzoic acid, a nucleic acid, a lipid, sulfate, phosphate, —$CH_2OCO$-alkyl and combinations thereof. In certain embodiments, such enzyme substrates can be cleaved by enzymes selected from peptidases, phosphatases, glycosidases, dealkylases, esterases, guanidinobenzotases, sulfatases, lipases, peroxidases, histone deacetylases, exonucleases, reductases, endoglycoceramidases and endonucleases.

In other embodiments, the carrier molecule is an amino acid (including those that are protected or are substituted by phosphates, carbohydrates, or $C_1$ to $C_{22}$ carboxylic acids), or a polymer of amino acids such as a peptide or protein. In a related embodiment, the carrier molecule contains at least five amino acids, more preferably 5 to 36 amino acids. Such peptides include, but are not limited to, neuropeptides, cytokines, toxins, protease substrates, and protein kinase substrates. Other peptides may function as organelle localization peptides, that is, peptides that serve to target the conjugated compound for localization within a particular cellular substructure by cellular transport mechanisms, including, but not limited to, nuclear localization signal sequences. In certain embodiments, the protein carrier molecules include enzymes, antibodies, lectins, glycoproteins, histones, albumins, lipoproteins, avidin, streptavidin, protein A, protein G, phycobiliproteins and other fluorescent proteins, hormones, toxins and growth factors. In other embodiments, the protein carrier molecule is an antibody, an antibody fragment, avidin, streptavidin, a toxin, a lectin, or a growth factor. In further embodiments, the carrier molecules contain haptens including, but not limited to, biotin, digoxin, digoxigenin and fluorophores.

The carrier molecules used in the methods and composition described herein can also contain a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. In other embodiments, the nucleotide carrier molecule is a nucleoside or a deoxynucleoside or a dideoxynucleoside, while in other embodiments, the carrier molecule contains a peptide nucleic acid (PNA) sequence or a locked nucleic acid (LNA) sequence. In certain embodiments, the nucleic acid polymer carrier molecules are single- or multi-stranded, natural or synthetic DNA or RNA oligonucleotides, or DNA/RNA hybrids, or incorporating an unusual linker such as morpholine derivatized phosphates (AntiVirals, Inc., Corvallis Oreg.), or peptide nucleic acids such as N-(2-aminoethyl)glycine units, where the nucleic acid contains fewer than 50 nucleotides, more typically fewer than 25 nucleotides.

The carrier molecules used in the methods and composition described herein can also contain a carbohydrate or polyol, including a polysaccharide, such as dextran, FICOLL, heparin, glycogen, amylopectin, mannan, inulin, starch, agarose and cellulose, or a polymer such as a poly(ethylene glycol). In certain embodiments, the polysaccharide carrier molecule includes dextran, agarose or FICOLL.

The carrier molecules used in the methods and composition described herein can also include a lipid including, but not limited to, glycolipids, phospholipids, and sphingolipids. In certain embodiments, such lipids contain 6-25 carbons. In other embodiments, the carrier molecules include a lipid vesicle, such as a liposome, The carrier molecules used in the methods and composition described herein can also be a cell, cellular systems, cellular fragment, or subcellular particles, including virus particles, bacterial particles, virus components, biological cells (such as animal cells, plant cells, bacteria, or yeast), or cellular components. Non-limiting examples of such cellular components that are useful as carrier molecules in the methods and composition described herein include lysosomes, endosomes, cytoplasm, nuclei, histones, mitochondria, Golgi apparatus, endoplasmic reticulum and vacuoles.

The carrier molecules used in the methods and composition described herein can also non-covalently associates with organic or inorganic materials.

The carrier molecules used in the methods and composition described herein can also include a specific binding pair member wherein the nucleic acid can be conjugated to a specific binding pair member and used in the formation of a bound pair. In certain embodiments, the presence of a labeled specific binding pair member indicates the location of the complementary member of that specific binding pair; each specific binding pair member having an area on the surface or in a cavity which specifically binds to, and is complementary with, a particular spatial and polar organization of the other. In certain embodiments, the dye compounds (fluorophores or chromophores) described herein function as a reporter molecule for the specific binding pair. Exemplary binding pairs are set forth in Table 2.

TABLE 2

Representative Specific Binding Pairs

| antigen | antibody |
|---|---|
| biotin | avidin (or streptavidin or anti-biotin) |
| IgG* | protein A or protein G |
| drug | drug receptor |
| folate | folate binding protein |
| toxin | toxin receptor |
| carbohydrate | lectin or carbohydrate receptor |
| peptide | peptide receptor |
| protein | protein receptor |
| enzyme substrate | enzyme |
| DNA (RNA) | cDNA (cRNA)† |
| hormone | hormone receptor |
| ion | chelator |

*IgG is an immunoglobulin
†cDNA and cRNA are the complementary strands used for hybridization In a particular aspect the carrier molecule, used in the methods and compositions described herein, is an antibody fragment, such as, but not limited to, anti-Fc, an anti-Fc isotype, anti-J chain, anti-kappa light chain, anti-lambda light chain, or a single-chain fragment variable protein; or a non-antibody peptide or protein, such as, for example but not limited to, soluble Fc receptor, protein G, protein A, protein L, lectins, or a fragment thereof. In one aspect the carrier molecule is a Fab fragment specific to the Fc portion of the target-binding antibody or to an isotype of the Fc portion of the target-binding antibody (U.S. Ser. No. 10/118,204). The monovalent Fab fragments are typically produced from either murine monoclonal antibodies or polyclonal antibodies generated in a variety of animals, for example but not limited to, rabbit or goat. These fragments can be generated from any isotype such as murine IgM, $IgG_1$, $IgG_{2a}$, $IgG_{2b}$, or $IgG_3$.

In alternative embodiments, a non-antibody protein or peptide such as protein G, or other suitable proteins, can be used alone or coupled with albumin. Preferred albumins include human and bovine serum albumins or ovalbumin. Protein A, G and L are defined to include those proteins known to one skilled in the art or derivatives thereof that comprise at least one binding domain for IgG, i.e. proteins that have affinity for IgG. These proteins can be modified but do not need to be and are conjugated to a reactive moiety in the same manner as the other carrier molecules described.

In another aspect, the carrier molecules, used in the methods and compositions described herein, can be whole intact antibodies. Antibody is a term of the art denoting the soluble substance or molecule secreted or produced by an animal in response to an antigen, and which has the particular property of combining specifically with the antigen that induced its formation. Antibodies themselves also serve are antigens or immunogens because they are glycoproteins and therefore are used to generate anti-species antibodies. Antibodies, also known as immunoglobulins, are classified into five distinct classes—IgG, IgA, IgM, IgD, and IgE. The basic IgG immunoglobulin structure consists of two identical light polypeptide chains and two identical heavy polypeptide chains (linked together by disulfide bonds).

When IgG is treated with the enzyme papain a monovalent antigen-binding fragment can be isolated, referred herein to as a Fab fragment. When IgG is treated with pepsin (another proteolytic enzyme), a larger fragment is produced, F(ab')$_2$. This fragment can be split in half by treating with a mild reducing buffer that results in the monovalent Fab' fragment. The Fab' fragment is slightly larger than the Fab and contains one or more free sulfhydryls from the hinge region (which are not found in the smaller Fab fragment). The term "antibody fragment" is used herein to define the Fab', F(ab')$_2$ and Fab portions of the antibody. It is well known in the art to treat antibody molecules with pepsin and papain in order to produce antibody fragments (Gorevic et al., Methods of Enzyol., 116:3 (1985)).

The monovalent Fab fragments used as carrier molecules in the methods and compositions described herein are produced from either murine monoclonal antibodies or polyclonal antibodies generated in a variety of animals that have been immunized with a foreign antibody or fragment thereof (U.S. Pat. No. 4,196,265 discloses a method of producing monoclonal antibodies). Typically, secondary antibodies are derived from a polyclonal antibody that has been produced in a rabbit or goat but any animal known to one skilled in the art to produce polyclonal antibodies can be used to generate anti-species antibodies. The term "primary antibody" describes an antibody that binds directly to the antigen as opposed to a "secondary antibody" that binds to a region of the primary antibody. Monoclonal antibodies are equal, and in some cases, preferred over polyclonal antibodies provided that the ligand-binding antibody is compatible with the monoclonal antibodies that are typically produced from murine hybridoma cell lines using methods well known to one skilled in the art.

In one aspect the antibodies used as carrier molecules in the methods and compositions described herein are generated against only the Fc region of a foreign antibody. Essentially, the animal is immunized with only the Fc region fragment of a foreign antibody, such as murine. The polyclonal antibodies are collected from subsequent bleeds, digested with an enzyme, pepsin or papain, to produce monovalent fragments. The fragments are then affinity purified on a column comprising whole immunoglobulin protein that the animal was immunized against or just the Fc fragments.

Solid Supports Azide Reactive, Alkyne Reactive or Phosphine Reactive

In an aspect of the methods and composition described herein, the modified nucleic acids can be covalently conjugated to a solid support. This includes, but is not limited to, any azide modified nucleic acid disclosed herein and any solid support disclosed herein. In certain embodiments, the modified nucleic acids contain at least one alkyne moiety or at least one phosphine moiety capable of reacting with a solid support containing an azide moiety. In other embodiments, the modified nucleic acids contain at least one azide moiety capable of reacting with a solid support containing an alkyne moiety or a phosphine moiety. In other embodiments, the modified nucleic acids contain at least one phosphine moiety capable of reacting with a solid support containing an azide moiety. In certain embodiments, the phosphine moieties of the modified nucleic acids and solid supports are triarylphosphine moieties.

A variety of solid supports can be used in the methods and compositions described herein. Such solid supports are not limited to a specific type of support, and therefore a large number of supports are available and are known to one of ordinary skill in the art. Such solid supports include, but are not limited to, solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports. Other non-limiting examples of solid supports used in the methods and compositions described herein include silica gels, polymeric membranes, particles, derivatized plastic films, derivatized glass, derivatized silica, glass beads, cotton, plastic beads, alumina gels, polysaccharides such as Sepharose, poly (acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly(ethylene glycol)), nylon, latex bead, magnetic bead, paramagnetic bead, superparamagnetic bead, starch and the like. In certain embodiments, the solid supports used in the methods and compositions described herein are substantially insoluble in liquid phases.

In certain embodiments, the solid support may include a solid support reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, wherein such functional groups are used to covalently attach the azide-containing nucleic acids described herein. In other embodiments, the solid support may include a solid support reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, wherein such functional groups are used to covalently attach the alkyne-containing nucleic acids described herein. In still other embodiments, the solid support may include a solid support reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, wherein such functional groups are used to covalently attach the phosphine-containing nucleic acids described herein. In other embodiments, the solid supports include azide, alkyne or phosphine functional groups to covalently attach nucleic acids modified with azide, alkyne or phosphine moieties.

A suitable solid phase support used in the methods and compositions described herein, can be selected on the basis of desired end use and suitability for various synthetic protocols. By way of example only, where amide bond formation is desirable to attach the modified nucleic acids described herein to the solid support, resins generally useful in peptide synthesis may be employed, such as polystyrene (e.g., PAM-resin obtained from Bachem Inc., Peninsula Laboratories, etc.), POLYHIPE™ resin (obtained from Aminotech, Canada), polyamide resin (obtained from Peninsula Laboratories), polystyrene resin grafted with polyethylene glycol (TentaGel™, Rapp Polymere, Tubingen, Germany), polydimethyl-acrylamide resin (available from Milligen/Biosearch, California), or PEGA beads (obtained from Polymer Laboratories). In certain embodiments, the modified nucleic acids described herein are deposited onto a solid support in an array format. In certain embodiments, such deposition is accomplished by direct surface contact between the support surface and a delivery mechanism, such as a pin or a capillary, or by ink jet technologies which utilize piezoelectric and other forms of propulsion to transfer liquids from miniature nozzles to solid surfaces. In the case of contact printing, robotic control systems and multiplexed printheads allow automated microarray fabrication. For contactless deposition by piezoelectric propulsion technologies, robotic systems also allow for automatic microarray fabrication using either continuous and drop-on-demand devices.

Compositions

In one aspect, the modified nucleic acids, reporter molecules and carrier molecules provided herein can be used to form a first composition that includes a modified nucleic acids, a first reporter molecule, and a carrier molecule. In another embodiment, a second nucleic acid that includes a first composition in combination with a second conjugate, wherein the second conjugate comprises a carrier molecule or solid support that is covalently bonded to a second reporter molecule. The first and second reporter molecules have different structures and preferably have different emission spectra. In other embodiments, the first and second reporter molecules are selected so that their fluorescence emissions essentially do not overlap. In other embodiments, the reporter molecules have different excitation spectra, while in other embodiments the reporter molecules have similar excitation wavelengths and are excited by the same laser. In such compositions, the carrier molecule (or solid support) of the conjugates in the second composition may be the same or a different molecule. The discussion herein pertaining to the identity of various carrier molecules is generally applicable to this embodiment as well as other embodiments.

In another aspect, the modified nucleic acids, reporter molecules and solid supports provided herein can be used to form a first composition that comprises a modified nucleic acid, a first reporter molecule, and a solid support. In another embodiment, a second composition that includes a first composition in combination with a second conjugate. The second conjugate comprises a solid support or carrier molecule (described herein) that is covalently bonded to a second reporter molecule. The first and second reporter molecules have different structures and preferably have different emission spectra. In other embodiments, the first and second reporter molecules are selected so that their fluorescence emissions essentially do not overlap. In other embodiments, the reporter molecules have different excitation spectra, while in other embodiments the reporter molecules have similar excitation wavelengths and are excited by the same laser. In such composition, the solid support (or carrier molecule) of the conjugates in the second composition may be the same or a different molecule. The discussion herein pertaining to the identity of various solid supports is generally applicable to this embodiment of the invention as well as other embodiments.

Labeling and Separating Modified Nucleic Acids

Methods for forming modified nucleic acid-label (reporter molecule, solid support or carrier molecule) conjugates are described herein. In one aspect the modified biomolecule-reporter molecule conjugates are formed in solution and then separated using methods known in the art. It was unexpectedly found that by adding a copper chelator to the "click" chemistry conjugation reaction the labeling efficiency of modified nucleic acids and their resolution in gel electrophoresis improved as compared to those reactions without the addition of a copper chelator. In certain embodiments, the methods of labeling nucleic acids using "click" chemistry, involve an azide modified nucleic acid and a label that includes a terminal alkyne that are reacted in a mixture that includes copper (II), a reducing agent, and at least one copper (I) chelator. In other embodiments, novel methods are provided for forming conjugates in solution with azide modified nucleic acids and a reporter molecule comprising a terminal alkyne under "click" chemistry conditions. In other embodiments, "click" chemistry is used to form conjugates with alkyne modified nucleic acids and a reporter molecule comprising an azide. In other embodiments, Staudinger ligation is used to form conjugates with azide modified nucleic acids and a reporter molecule comprising a phosphine, while other embodiments use Staudinger ligation to form conjugates with phosphine modified nucleic acids and a reporter molecule comprising an azide. Still other embodiments use activated alkyne modified nucleic acids to form conjugates with reporter molecules comprising azides, or azide modified nucleic acids forming conjugates with activated alkyne containing reporter molecules.

In other aspects provided herein, the methods of labeling nucleic acids using "click" chemistry, wherein a nucleic acid that includes an azido group and a label that comprises a terminal alkyne are reacted in a mixture that includes copper (II), a reducing agent, and at least one copper (I) chelator to produce a labeled nucleic acid, results in the preservation of the structural integrity of the labeled nucleic acid. In other embodiments, methods of labeling glycoproteins wherein the structural integrity of the nucleic acid after labeling is not reduced includes "click" chemistry in which a nucleic acid that includes a terminal alkyne and a label that comprises an azido group are reacted in a mixture that includes copper (II), a reducing agent, and at least one copper chelator.

The methods for labeling nucleic acids that comprise an azido group using "click" chemistry described herein can also be used for nucleic acids that comprise a terminal alkyne, wherein the label to be reacted with the nucleic acid comprises an azido group. The methods for labeling and detecting nucleic acids that comprise an azido group using "click" chemistry described herein can also be used for nucleic acids that comprise a terminal alkyne, wherein the label to be reacted with the nucleic acid comprises an azido group. In one embodiment, is a method using the "click" chemistry reaction described herein to form nucleic acid-reporter molecule conjugates in which the reaction mixture includes a reporter molecule with an azide moiety, an alkyne modified nucleic acid, copper (II) ions, at least one reducing agent and a copper chelator. In certain embodiments, such alkyne modified nucleic acids are alkyne modified glycoproteins and such reporter molecule with an azide moiety are any reporter molecule described herein. In other embodiments, such alkyne modified nucleic acids are alkyne modified glycoproteins and such reporter molecule with an azide moiety are any fluorophore based reporter molecule described herein.

Other methods provided herein, are methods for labeling and detecting separated nucleic acids using the "click" chemistry cycloaddition reaction described herein. The method includes: combining in a reaction mixture a nucleic acid that comprises an azido group, a label that includes a terminal alkyne group, copper (II), a reducing agent, and a copper chelator; incubating the reaction mixture under conditions that promote chemical conjugation of the label to the nucleic acid, separating the nucleic acid using one or more biochemical or biophysical separation techniques, and detecting the nucleic acid. In other embodiments, the method includes: combining in a reaction mixture a nucleic acid that comprises an alkyne group, a label that includes an azide group, copper (II), a reducing agent, and a copper chelator; incubating the reaction mixture under conditions that promote chemical conjugation of the label to the nucleic acid, separating the nucleic acid using one or more biochemical or biophysical separation techniques, and detecting the nucleic acid.

In one embodiment is a method for forming a modified nucleic acid label (reporter molecule, solid support or carrier molecule) conjugate, wherein the method includes the steps of:

a) forming an azide-alkyne cycloaddition reaction mixture that includes a label having a terminal alkyne moiety, an azido modified nucleic acid, copper(II) ions, at least one reducing agent and a copper chelator;

b) incubating the azide-alkyne cycloaddition reaction mixture for a sufficient amount of time to form a nucleic acid-label conjugate;

c) separating the nucleic acid-label conjugate to form a separated nucleic acid-label conjugate wherein the nucleic acid label conjugated is formed and separated.

In an alternative embodiment, step a) comprises a label having an azido moiety and the modified nucleic acid comprises an alkyne.

In another alternative embodiment, step a) comprises forming a Staudinger ligation reaction.

In yet another embodiment, step a) does not comprise copper(II) ions, at least one reducing agent and a copper chelator wherein the label comprises an azido moiety or an activated alkyne and the modified nucleic acid comprises an azido moiety or an activated alkyne.

In another embodiment is a method for detecting modified nucleic acids, wherein the method includes the steps of:

a) forming an azide-alkyne cycloaddition reaction mixture that includes a reporter molecule having a terminal alkyne moiety, an azido modified nucleic acid, copper (II) ions, at least one reducing agent and a copper chelator;

b) incubating the azide-alkyne cycloaddition reaction mixture for a sufficient amount of time to form a nucleic acid-reporter molecule conjugate;

c) separating the nucleic acid-reporter molecule conjugate to form a separated nucleic acid-reporter molecule conjugate;

d) illuminating the separated nucleic acid-reporter molecule conjugate with an appropriate wavelength to form an illuminated nucleic acid-reporter molecule conjugate, and e) observing the illuminated nucleic acid-reporter molecule conjugate wherein the nucleic acids is detected.

In another embodiment is a method for detecting modified nucleic acids, wherein the method includes the steps of:

a) forming an azide-alkyne cycloaddition reaction mixture that includes a reporter molecule having an azide moiety, an alkyne modified nucleic acid, copper(II) ions, at least one reducing agent and a copper chelator;

b) incubating the azide-alkyne cycloaddition reaction mixture for a sufficient amount of time to form a nucleic acid-reporter molecule conjugate;

c) separating the nucleic acid-reporter molecule conjugate to form a separated nucleic acid-reporter molecule conjugate;

d) illuminating the separated nucleic acid-reporter molecule conjugate with an appropriate wavelength to form an illuminated nucleic acid-reporter molecule conjugate, and e) observing the illuminated nucleic acid-reporter molecule conjugate wherein the nucleic acid is detected.

In addition such "click" chemistry reaction mixtures can include, without limitation, one or more buffers, polymers, salts, detergents, or solubilizing agents. The reaction can be performed under anaerobic conditions, such as under nitrogen or argon gas, and can be performed for any feasible length of time, such as, for example, from ten minutes to six hours, from about twenty minutes to about three hours, or from about thirty minutes to about two hours. The reaction can be performed at a wide range of temperatures, for example ranging from about 4 degrees Celsius to about 50 degrees Celsius, and is preferably performed at temperatures between about 10 degrees and about 40 degrees, and typically between about 15 degrees and about 30 degrees.

Separation and Detection

Another aspect provided herein are methods directed toward detecting modified nucleic acids after the modified nucleic acids have been labeled, using "click" chemistry reactions, Staudinger ligation or activated alkyne reactions, and separated using, for example, chromatographic methods or electrophoresis methods such as, but not limited to, gel electrophoresis. In certain embodiments such nucleic acids have been modified using the methods described herein. The separation methods used to separate such modified nucleic acids includes, but are not limited to, thin layer or column chromatography (including, for example, size exclusion, ion exchange, or affinity chromatography) or isoelectric focusing, gel electrophoresis, capillary electrophoresis, capillary gel electrophoresis, and slab gel electrophoresis. Gel electrophoresis can be denaturing or nondenaturing gel electrophoresis, and can include denaturing gel electrophoresis followed by nondenaturing gel electrophoresis (e.g., "2D" gels). In certain embodiments, the modified nucleic acids are used to form conjugates with a reporter molecule, a carrier molecule and/or a solid support prior to separation using the methods described herein. In other embodiments, the modified nucleic acids are used to form conjugates with a reporter molecule, a carrier molecule and/or a solid support after separation using the methods described herein.

In other embodiments, the separation methods used in such separation and detection methods can be any separation methods used for nucleic acids, such as, for example, chromatography, capture to solid supports, and electrophoresis. In certain embodiments of such separation and detection methods, gel electrophoresis is used to separate nucleic acids and the separated nucleic acids are detected in the gel by the attached labels. By way of example only, nucleic acids that have incorporated azido moieties can be labeled in a solution reaction with a terminal alkyne-containing fluorophore, and the nucleic acids can be optionally further purified from the reaction mixture and electrophoresed. The nucleic acids can be visualized in the gel using light of the appropriate wavelength to stimulate the fluorophore label. Single or double stranded nucleic acids can be attached to solid supports prior to incorporation of azido or alkyne nucleotides followed by "click" reaction with a respective azido or alkyne chemical or polymer. Nucleic acids that have alkyne or azide-nucleotides can be attached to solid supports before or after the click reaction.

Gel electrophoresis can use any feasible buffer system described herein including, but not limited to, Tris-acetate EDTA, Tris-borate EDTA, Tris-glycine, BisTris and Bistris-Tricine. In certain embodiments, the electrophoresis gel used in the methods described herein comprise acrylamide, including by way for example only, acrylamide at a concentration from about 2.5% to about 30%, or from about 5% to about 20%. In certain embodiments, such polyacrylamide electrophoresis gel comprise 1% to 10% crosslinker, including but not limited to, bisacrylamide. In certain embodiments, the electrophoresis gel used in the methods described herein comprises agarose, including by way for example only, agarose at concentration from about 0.1% to about 5%, or from about 0.5% to about 4%, or from about 1% to about 3%. In certain embodiments, the electrophoresis gel used in the methods described herein comprises acrylamide and agarose, including by way for example only, electrophoresis gels comprising from about 2.5% to about 30% acrylamide and from about 0.1% to about 5% agarose, or from about 5% to about 20% acrylamide and from about 0.2% to about 2.5% agarose.

In certain embodiments, such polyacrylamide/agarose electrophoresis gels comprise 1% to 10% crosslinker, including but not limited to, bisacrylamide. In certain embodiments, the gels used to separate nucleic acids can be gradient gels.

The methods described herein can be used to detect modified nucleic acids for "in-gel" detection using slab gel electrophoresis or capillary gel electrophoresis. In one aspect, the method includes combining an azido modified nucleic acid, a label that includes a terminal alkyne, copper (II), a reducing agent, and a copper (I) chelator in a reaction mixture; incubating the reaction mixture under conditions that promote chemical conjugation of the label to the nucleic acid; separating the nucleic acid using one or more biochemical separation techniques; and detecting the nucleic acid. The label used in such methods can be any label described herein. The copper (I) chelator used in such methods can be any chelator described herein. In certain embodiments, the copper (I) chelator use in such methods is a 1,10 phenanthroline-containing copper (I) chelator. In other embodiments, the copper (I) chelator is bathocuproine disulfonic acid (BCS; 2,9-dimethyl-4,7-diphenyl-1,10-phenanthroline disulfonate). In other embodiments, the copper (I) chelator used in such methods can be used to chelate copper(II).

Without limitation to any specific mechanism, it is known that copper can promote the cleavage of nucleic acids. The addition of a copper chelator in such methods reduces the detrimental effects of copper used in the "click" chemistry reactions, and thereby preserves the structural integrity of the nucleic acids. Thus, the methods described herein preserve the structural integrity of labeled and detected nucleic acids, and thereby provide improved methods of separating and detecting nucleic acids labeled using "click" chemistry. In addition, the methods of detecting separated nucleic acids using click chemistry, in which the structural integrity of the separated molecules is preserved, improves the detection of such nucleic acids.

Figure 10:
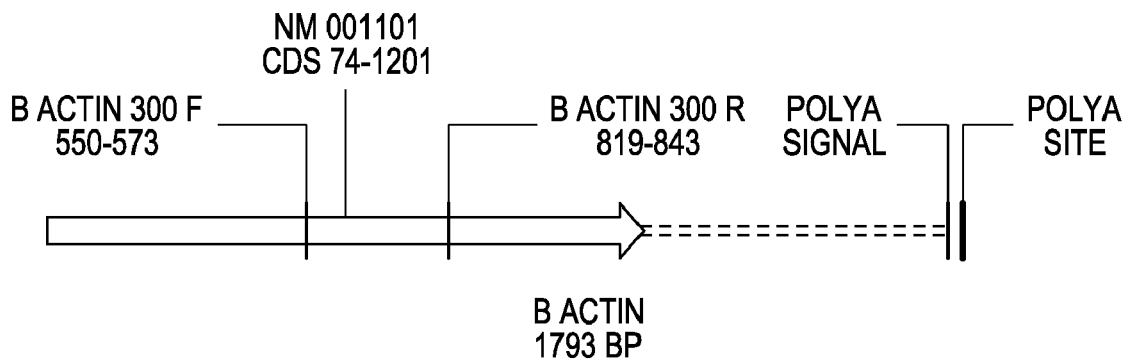

In certain embodiments, the addition of a chelator including, but not limited to BCS, preserves Telomerase Laddering (see FIG. 10).

In another embodiment of "in-gel" detection, the method includes combining an alkyne modified nucleic acid that comprises a terminal alkyne, a label that includes an azido group, copper (II), a reducing agent, and a copper (I) chelator in a reaction mixture; incubating the reaction mixture under conditions that promote chemical conjugation of the label to the nucleic acid; separating the labeled nucleic acid using one or more biochemical separation techniques; and detecting the nucleic acid. In these methods, the structural integrity of labeled and detected nucleic acids is preserved. The label used in such methods can be any label described herein. The copper (I) chelator used in such methods can be any chelator described herein. In certain embodiments, the copper (I) chelator use in such methods is a 1,10 phenanthroline-containing copper (I) chelator. In other embodiments, the copper (I) chelator is bathocuproine disulfonic acid (BCS; 2,9-dimethyl-4,7-diphenyl-1,10-phenanthroline disulfonate. In other embodiments, the copper (I) chelator used in such methods can be used to chelate copper(II).

In certain embodiments, in-gel fluorescence detection utilizes fluorescent- and/or UV-excitable alkyne containing probes, or fluorescent- and/or UV-excitable azide containing probes. In certain embodiments, the labels used in such separation and detection methods are any fluorophores described herein which has been derivatized to contain an alkyne, an azide or a phosphine. Incertain embodiments, such fluorphores include, but are not limited to, fluorescein, rhodamine, TAMRA, an Alexa dye, a SYPRO dye, or a BODIPY dye.

The method described herein can be used for multiplexed detection of nucleic acids, by labeling a modified nucleic acid using the methods described herein, and then using a total nucleic acid stain to stain the gel that includes the modified nucleic acids labeled with a fluorophore having distinct spectral emission.

In another aspect, nucleic acids can be labeled with an azido tag, electrophoresed on gels, and the resulting gels can be incubated with an alkyne tag, such as a fluorescent alkyne tag in the presence of copper (I). Copper (I) can be added in its natural form (e.g. CuBr) or can be produced in situ from copper (II) compounds with the addition of a reducing agent. The reducing agent used in such methods can be any reducing agent described herein, including but not limited to, ascorbate or TCEP. Addition of a chelator that stabilizes copper (I) can enhance the chemical ligation. The fluorescent label used in such methods can be any fluorophore described herein. The copper (I) chelator used in such methods can be any chelator described herein. In certain embodiments, the copper (I) chelator use in such methods is a 1,10 phenanthroline-containing copper (I) chelator. In other embodiments, the copper (I) chelator is bathocuproine disulfonic acid (BCS; 2,9-dimethyl-4,7-diphenyl-1,10-phenanthroline disulfonate). In other embodiments, the copper (I) chelator used in such methods can be used to chelate copper(II). After the ligation step, the gel is washed and the tagged proteins are visualized using standard fluorescence scanning devices.

In other embodiments, nucleic acids can be labeled with an alkyne tag, electrophoresed on gels, and the resulting gels can be incubated with an azide tag, such as a fluorescent azide tag in the presence of copper (I). Copper (I) can be added in its natural form (e.g. CuBr) or can be produced in situ from copper (II) compounds with the addition of a reducing agent. The reducing agent used in such methods can be any reducing agent described herein, including but not limited to, ascorbate or TCEP. Addition of a chelator that stabilizes copper (I) can enhance the chemical ligation. The fluorescent label used in such methods can be any fluorophore described herein. The copper (I) chelator used in such methods can be any chelator described herein. In certain embodiments, the copper (I) chelator use in such methods is a 1,10 phenanthroline-containing copper (I) chelator. In other embodiments, the copper (I) chelator is bathocuproine disulfonic acid (BCS; 2,9-dimethyl-4,7-diphenyl-1,10-phenanthroline disulfonate. In other embodiments, the copper (I) chelator used in such methods can be used to chelate copper(II). After the ligation step, the gel is washed and the tagged proteins are visualized using standard fluorescence scanning devices.

In further embodiments, nucleic acids can be labeled with an azide tag, electrophoresed on gels, and the resulting gels can be incubated with a phosphine tag, such as a fluorescent phosphine containing tag, using Staudinger ligation. After the ligation step, the gel is washed and the tagged nucleic acids are visualized using standard fluorescence scanning devices. In such methods the use of copper, which contributes to the degradation of nucleic acids such as proteins, can be avoided.

In certain embodiments, a label attached to a nucleic acid using a "click" chemistry reaction with a copper (I) chelator as disclosed herein, can also be used for the separation of nucleic acids. By way of example only, affinity chromatography or bead capture techniques can be used to separate nucleic acids labeled with biotin or other affinity tags using the methods described herein. The captured molecules can be detected using the affinity tags or by other means, and/or further analyzed for structure or function.

Methods for Labeling Immobilized Modified Nucleic Acids

Another aspect provides a method for labeling modified nucleic acids that have been immobilized on a solid support. Solid supports used in such methods have been described herein, and can be solid or semi-solid matrix. Such solid supports include, but are not limited to, glass, slides, arrays, silica particles, polymeric particles, microtiter plates and polymeric gels. In this aspect the nucleic acids are modified using the methods described herein. In certain aspects it is advantageous to first immobilize the modified nucleic acids and then to subsequently form a nucleic acid conjugate comprising the nucleic acid and a reporter molecule, carrier molecule and the solid support, wherein the reporter molecule, carrier molecule or solid support comprise a reactive group used to form the conjugate. In certain embodiments such reactive groups are alkynes for reacting with azides. In certain embodiments such reactive groups are activated alkynes for reacting with azides. In certain embodiments such reactive groups are phosphines for reacting with azides. In certain embodiments such reactive groups are azides for reacting with alkynes. In certain embodiments, the conjugate is formed under "click" chemistry conditions wherein the reporter molecule, carrier molecule or solid support comprises an alkyne or an azide. In another aspect the conjugate is formed under Staudinger ligation conditions wherein the reporter molecule, carrier molecule or solid support comprises a triaryl phosphine or an azide. In another aspect the conjugate is formed using activated alkynes wherein the reporter molecule, carrier molecule or solid support comprises an activated alkyne or an azide.

In certain aspects it is advantageous to first immobilize the modified nucleic acid and then to detect the immobilized nucleic acid using standard hybridization techniques wherein the hybridized probe is detected using methods well known in the art. In this instance the modified nucleic acid comprises a reactive group that are alkynes for reacting with azides. In certain embodiments such reactive groups are activated alkynes for reacting with azides. In certain embodiments such reactive groups are phosphines for reacting with azides. In certain embodiments such reactive groups are azides for reacting with alkynes.subsequently form a nucleic acid conjugate comprising the nucleic acid and a solid support, wherein the solid support comprises a reactive group used to form the conjugate.

In certain embodiments, it is advantageous to first immobilize the azido modified nucleic acids and then to subsequently form the nucleic acid conjugate comprising a reporter molecule, carrier molecule or solid support wherein the reporter molecule, carrier molecule or solid support comprise an azide reactive group prior to forming the conjugate. In certain embodiments, the conjugate is formed under "click" chemistry conditions wherein the reporter molecule, carrier molecule or solid support comprises a terminal alkyne. In another aspect the conjugate is formed under Staudinger ligation conditions wherein the reporter molecule, carrier molecule or solid support comprises a triaryl phosphine.

In another aspect, the modified nucleic acid is attached to a solid support using functional groups other than functional groups used in "click" chemistry or Staudinger ligation, whereupon the attached modified nucleic acid is used to form a conjugate under "click" chemistry conditions or Staudinger ligation with reporter molecules, carrier molecule or another solid support that have functional groups used in "click" chemistry or Staudinger ligation. By way of example only, the modified nucleic acid can be immobilized to a solid support using hydroxyl, carboxyl, amino, thiol, aldehyde, halogen, nitro, cyano, amido, urea, carbonate, carbamate, isocyanate, sulfone, sulfonate, sulfonamide or sulfoxide functional groups. In certain embodiments the modified nucleic acid is an azido modified nucleic acid, an alkyne modified nucleic acid or a phosphine modified nucleic acid.

In certain embodiments, the azido modified nucleic acid is attached to a solid support using functional groups other than azide reactive functional groups, whereupon the attached azido modified nucleic acid is used to form a conjugate under click chemistry conditions wherein the reporter molecule, carrier molecule or another solid support comprises a terminal alkyne. In another embodiment the azido modified nucleic acid is attached to a solid support using functional groups other than azide reactive functional groups, whereupon the attached azido modified nucleic acid is used to form a conjugate under Staudinger ligation conditions wherein the reporter molecule, carrier molecule or other solid support comprises a triaryle phosphine.

In another aspect is provided a method for detecting immobilized azido modified nucleic acids, wherein the method includes the following:
a) immobilizing the azido modified nucleic acids on a solid or semi-solid matrix to form an immobilized azido modified nucleic acid;
b) contacting the immobilized azido modified nucleic acid with a reporter molecule that contains an alkyne reactive group to form a contacted azido modified nucleic acid;
c) incubating the contacted azido modified nucleic acid for a sufficient amount of time to form a reporter molecule-nucleic acid conjugate;
d) illuminating the reporter molecule-nucleic acid conjugate with an appropriate wavelength to form an illuminated reporter molecule-nucleic acid conjugate, and
e) observing the illuminated reporter molecule-nucleic acid conjugate whereby the immobilized azido modified nucleic acid is detected.

In another aspect is provided a method for detecting immobilized alkyne modified nucleic acids, wherein the method includes the following:
a) immobilizing the alkyne modified nucleic acids on a solid or semi-solid matrix to form an immobilized alkyne modified nucleic acid;
b) contacting the immobilized alkyne modified nucleic acid with a reporter molecule that contains an azide reactive group to form a contacted alkyne modified nucleic acid;
c) incubating the contacted alkyne modified nucleic acid for a sufficient amount of time to form a reporter molecule-nucleic acid conjugate;
d) illuminating the reporter molecule-nucleic acid conjugate with an appropriate wavelength to form an illuminated reporter molecule-nucleic acid conjugate, and
e) observing the illuminated reporter molecule-nucleic acid conjugate whereby the immobilized alkyne modified nucleic acid is detected.

RNAi

RNAi is method for selectively decreasing gene expression and is a cost effective method used to study specific gene targets. Typically RNAi oligos are short 20 basepair nucleotides. Hybridization of the oligonucleotide to a targeted gene triggers specific degradation of the gene and thereby decreases gene expression. Using Click modified oligos could potentially increase the specificity of the Watson-Crick binding of these short oligonucleotides by increasing the Tm. Similar types of experiments have been done with locked nucleic acids (LNA) (Elmen, J. et al 2005, Nuc Acid Res). The Click modification could also potentially decrease the susceptibility of the free RNAi oligos to destruction by nucleases after transfection, thereby increasing the half life and effectiveness of the oligonucleotides.

Methods Using Chemically Labeled Nucleic Acids

It was unexpectedly observed that azide modified-dATP and alkyne modified-dUTP could be incorporated into a nucleic acid polymer using amplification techniques including, but not limited to PCR. It was also unexpectedly observed that azide modified-dATP and alkyne modified-dUTP could be incorporated into a nucleic acid polymer using a Telomerase resulting in Telomerase laddering (see FIGS. 4-7 (Example 1-4). Telomerase is an enzyme that adds specific DNA sequence repeats ("TTAGGG" in all vertebrates) to the 3' ("three prime") end of DNA strands in the telomere regions, which are found at the ends of eukaryotic chromosomes. The enzyme is a reverse transcriptase that carries its own RNA molecule, which is used as a template when it elongates telomeres, which are shortened after each replication cycle. Therefore, one aspect of the methods of using the modified nucleotides described herein is in a telomerase activity assay.

In another aspect, such modified nucleotides are labeled using click-chemistry based, while in other embodiments such modified nucleotides are labeled using Staudinger Ligation. In still other embodiments, such modified nucleotides are labeled using activated alkyne reactivity. In certain embodiments, the modified nucleotides are azide modified nucleotides which are labeled using click-chemistry, while in other embodiments such modified nucleotides are azide nucleotides labeled using Staudinger Ligation. In still other embodiments, such modified nucleotides are azide modified nucleotides which are labeled using activated alkyne reactivity. In certain embodiments, the modified nucleotides are alkyne modified nucleotides which are labeled using click-chemistry, while in other embodiments such modified nucleotides are activated alkyne modified nucleotides which are labeled using activated alkyne reactions with azides. In certain embodiments, the modified nucleotides are azide modified-dATP which are labeled using click-chemistry (see FIG. 6), while in other embodiments such modified nucleotides are azide modified-dATP labeled using Staudinger Ligation. In still other embodiments, such modified nucleotides are azide modified-dATP which are labeled using activated alkyne reactivity. In certain embodiments, the modified nucleotides are alkyne modified-dATP which are labeled using click-chemistry, while in other embodiments such modified nucleotides are activated alkyne modified-dATP which are labeled using activated alkyne reactions with azides. In certain embodiments, the modified nucleotides are azide modified-dATP which are labeled using click-chemistry, while in other embodiments such modified nucleotides are azide modified-dUTP labeled using Staudinger Ligation. In still other embodiments, such modified nucleotides are azide modified-dATP or dUTP which are labeled using activated alkyne reactivity. In certain embodiments, the modified nucleotides are alkyne modified-dUTP which are labeled using click-chemistry (see FIGS. 7-9), while in other embodiments such modified nucleotides are activated alkyne modified-dUTP which are labeled using activated alkyne reactions with azides. The telomerase assay can serve as a highly significant cancer diagnostic as this enzyme is activated in 90% of known human and other animal cancers. The level of telomerase activity can be used as a reliable biomarker that represents the different levels of the cancer disease. Therefore, this assay can help diagnose and evaluate the level of cancer progression in a patient and help determine the response to anticancer treatments.

Thus, in one embodiment is provided a method of measuring Telomerase Enzyme Activity, comprising steps of:

a) contacting a cell with an effective amount of a dNTP mix, a dNTP that comprises an azide group or an alkyne group, a telomerase substrate primer molecule that may contain a terminal biotin molecule, a telomerase enzyme such that the azide or alkyne modified dNTP is incorporated into at least one nucleic acid polymer;

b) contacting the nucleic acid polymer with a reporter molecule comprising an alkyne, activated alkyne, azide, or phosphine moiety to form a modified nucleic acid polymer reporter molecule conjugate;

c) separating the modified nucleic acid polymer reporter molecule from free unreacted reporter; and d) Detecting the labeled nucleic acid reporter molecule conjugate.

In another aspect, such modified nucleotides described herein are incorporated into nucleic acid polymers using the methods described herein including, but not limited to, polymerase chain reaction (PCR), ligation-based thermocycling approaches, reverse transcription-PCR, real-time PCR, linear amplification techniques and isothermal DNA amplification techniques such as, by way of example only, real-time strand displacement amplification (SDA), rolling-circle amplification (RCA), multiple-displacement amplification (MDA), Q-beta replicase amplification, automated Q-beta replicase amplification assay and other RNA polymerase mediated techniques such as, for example, nucleic acid sequence based amplification or NASBA. Such incorporated nucleotides are then labeled using click-chemistry, while in other embodiments such modified nucleotides are labeled using Staudinger Ligation. In still other embodiments, such incorporated nucleotides are labeled using activated alkyne reactivity. In certain embodiments, the incorporated nucleotides are azide modified nucleotides which are labeled using click-chemistry, while in other embodiments such modified nucleotides are azide nucleotides labeled using Staudinger Ligation. In still other embodiments, such incorporated nucleotides are azide modified nucleotides which are labeled using activated alkyne reactivity. In certain embodiments, the incorporated nucleotides are alkyne modified nucleotides which are labeled using click-chemistry, while in other embodiments such modified nucleotides are activated alkyne modified nucleotides which are labeled using activated alkyne reactions with azides. In certain embodiments, the incorporated nucleotides are azide modified-dATP which are labeled using click-chemistry (see FIG. 6), while in other embodiments such modified nucleotides are azide modified-dATP labeled using Staudinger Ligation. In still other embodiments, such incorporated nucleotides are azide modified-dATP which are labeled using activated alkyne reactivity. In certain embodiments, the incorporated nucleotides are alkyne modified-dATP which are labeled using click-chemistry, while in other embodiments such modified nucleotides are activated alkyne modified-dATP which are labeled using activated alkyne reactions with azides. In certain embodiments, the incorporated nucleotides are azide modified-dUTP which are labeled using click-chemistry, while in other embodiments such modified nucleotides are azide modified-dUTP labeled using Staudinger Ligation. In still other embodiments, such modified nucleotides are azide modified-dUTP which are labeled using activated alkyne reactivity. In certain embodiments, the incorporated nucleotides are alkyne modified-dUTP which are labeled using click-chemistry (see FIGS. 7-9), while in other embodiments such modified nucleotides are activated alkyne modified-d UTP which are labeled using activated alkyne reactions with azides.

Figure 9:
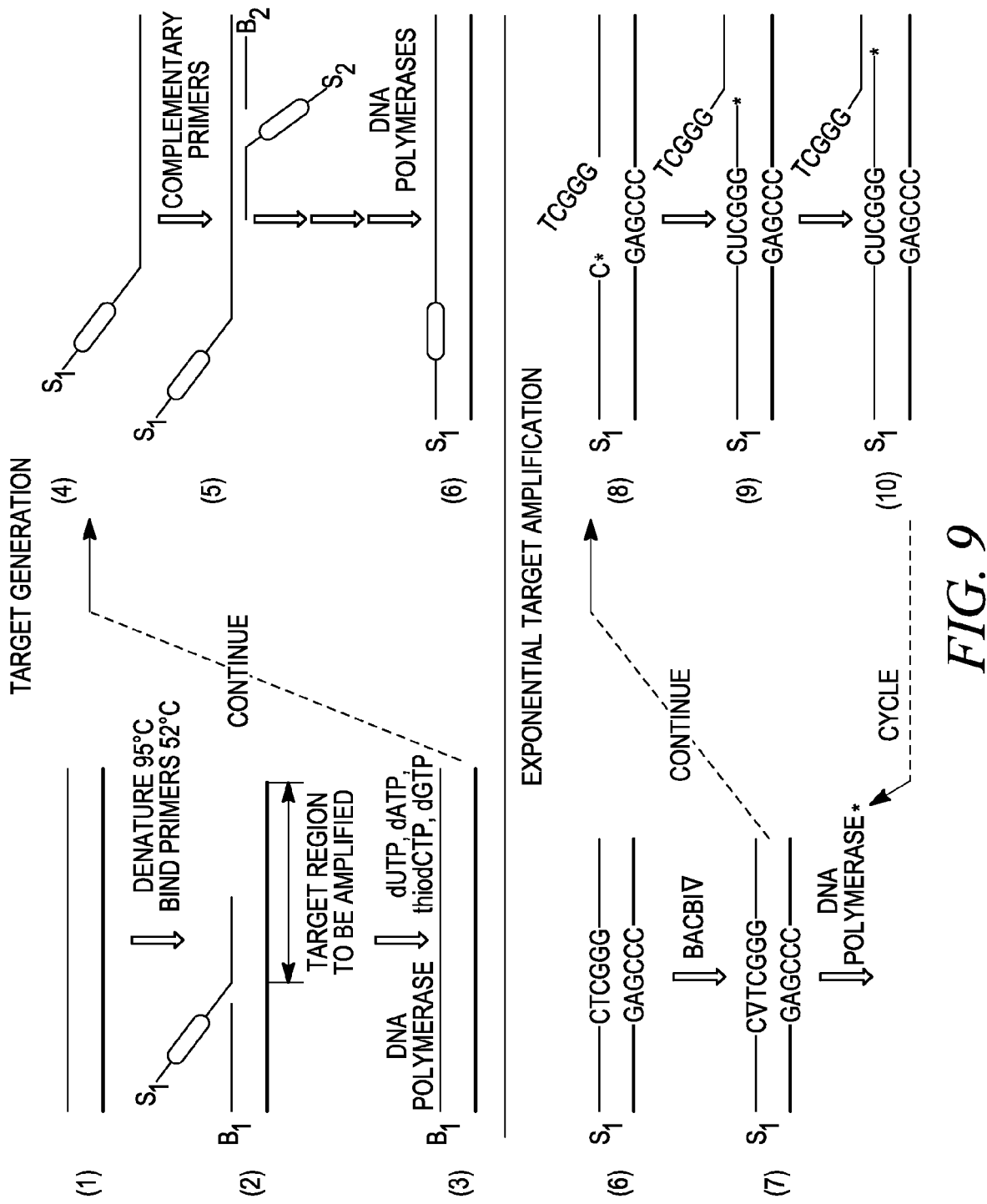

In another aspect, such modified nucleotides described herein are incorporated into nucleic acid polymers using isothermal amplification. Such incorporated nucleotides are then labeled using click-chemistry, while in other embodiments such modified nucleotides are labeled using Staudinger Ligation. In still other embodiments, such incorporated nucleotides are labeled using activated alkyne reactivity. In certain embodiments, the incorporated nucleotides are azide modified nucleotides which are labeled using click-chemistry, while in other embodiments such modified nucleotides are azide nucleotides labeled using Staudinger Ligation. In still other embodiments, such incorporated nucleotides are azide modified nucleotides which are labeled using activated alkyne reactivity. In certain embodiments, the incorporated nucleotides are alkyne modified nucleotides which are labeled using click-chemistry, while in other embodiments such modified nucleotides are activated alkyne modified nucleotides which are labeled using activated alkyne reactions with azides. In certain embodiments, the incorporated nucleotides are azide modified-dATP which are labeled using click-chemistry, while in other embodiments such modified nucleotides are azide modified-dATP labeled using Staudinger Ligation. In still other embodiments, such incorporated nucleotides are azide modified-dATP which are labeled using activated alkyne reactivity. In certain embodiments, the incorporated nucleotides are alkyne modified-dATP which are labeled using click-chemistry, while in other embodiments such modified nucleotides are activated alkyne modified-dATP which are labeled using activated alkyne reactions with azides. In certain embodiments, the incorporated nucleotides are azide modified-dUTP which are labeled using click-chemistry, while in other embodiments such modified nucleotides are azide modified-dUTP labeled using Staudinger Ligation. In still other embodiments, such modified nucleotides are azide modified-dUTP which are labeled using activated alkyne reactivity. In certain embodiments, the incorporated nucleotides are alkyne modified-dUTP which are labeled using click-chemistry (see FIGS. 7-9), while in other embodiments such modified nucleotides are activated alkyne modified-dUTP which are labeled using activated alkyne reactions with azides. In particular, FIG. 9 shows that E-dUTP can be incorporated using various polymerases, thereby showing an isothermal DNA extension assay for second strand cDNA synthesis using primer extension.

In certain embodiments, a mixture of modified nucleotides are incorporated using the methods described herein including, but not limited to, polymerase chain reaction (PCR), ligation-based thermocycling approaches, reverse transcription-PCR, real-time PCR, linear amplification techniques and isothermal DNA amplification techniques such as, by way of example only, real-time strand displacement amplification (SDA), rolling-circle amplification (RCA), multiple-displacement amplification (MDA), Q-beta replicase amplification, automated Q-beta replicase amplification assay and other RNA polymerase mediated techniques such as, for example, nucleic acid sequence based amplification or NASBA. In certain embodiments the mixture of modified nucleotides is a mixture of azide modified nucleotides, while in other embodiments the mixture of modified nucleotides is a mixture of alkyne modified nucleotides. In certain embodiments the mixture of modified nucleotides is a mixture of azide modified dATP and dUTP nucleotides, while in other embodiments the mixture of modified nucleotides is a mixture of alkyne modified dATP and dUTP. In certain embodiments, the nucleic acid polymers having a mixtures of modified nucleotides is labeled as described above.

Figure 4:
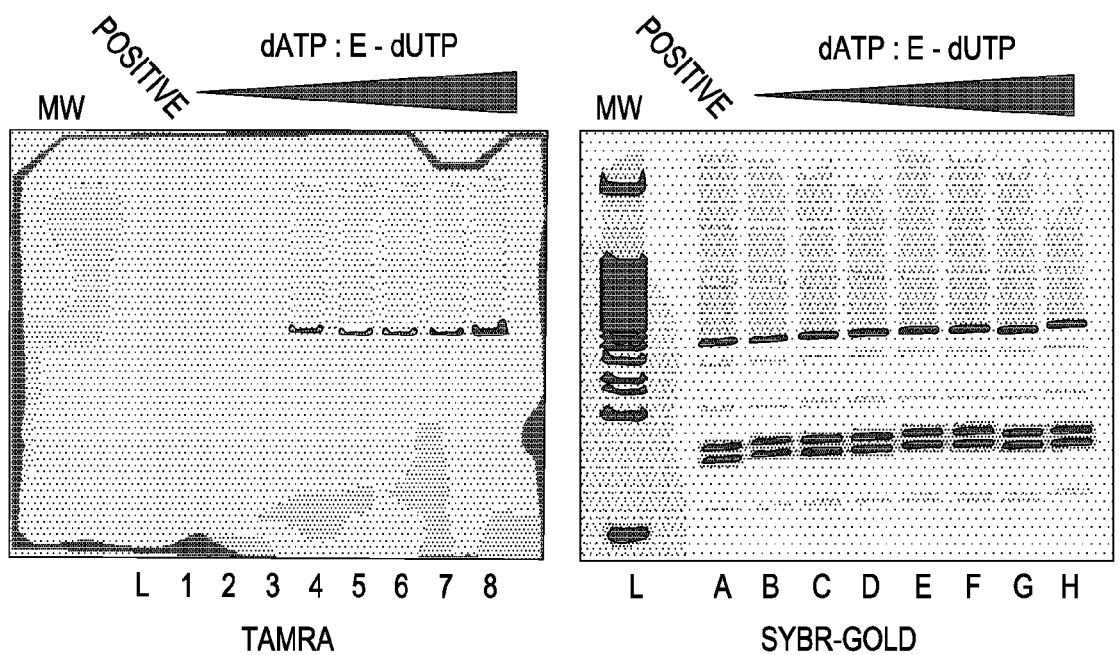
Figure 5:
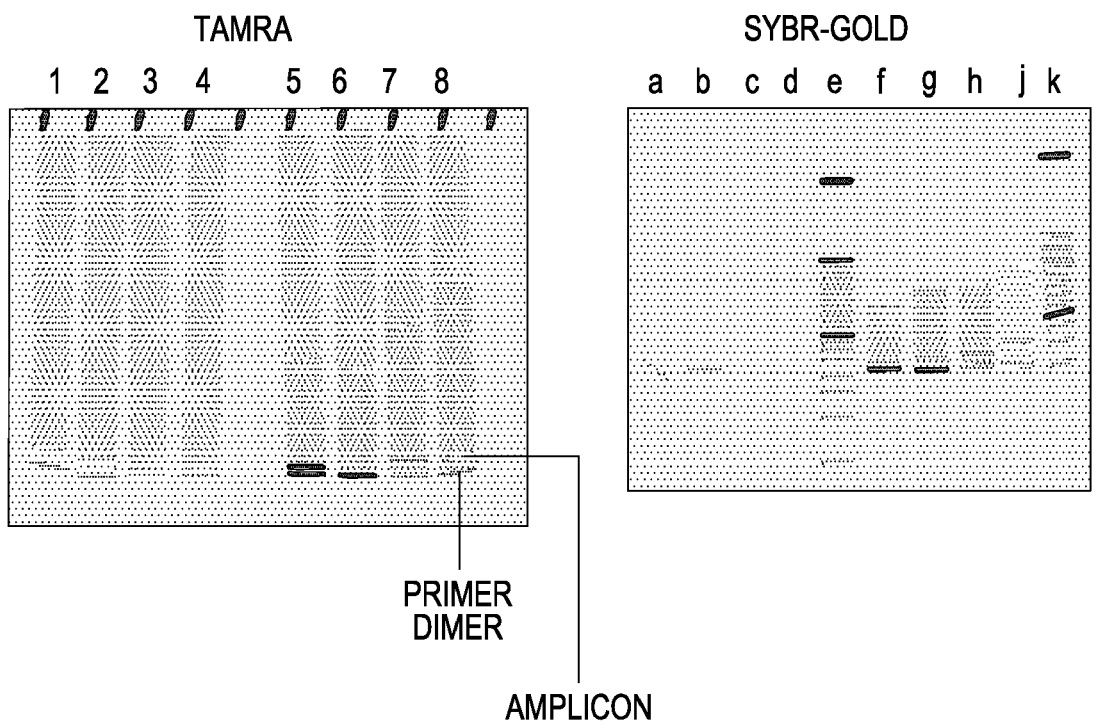
Figure 7:
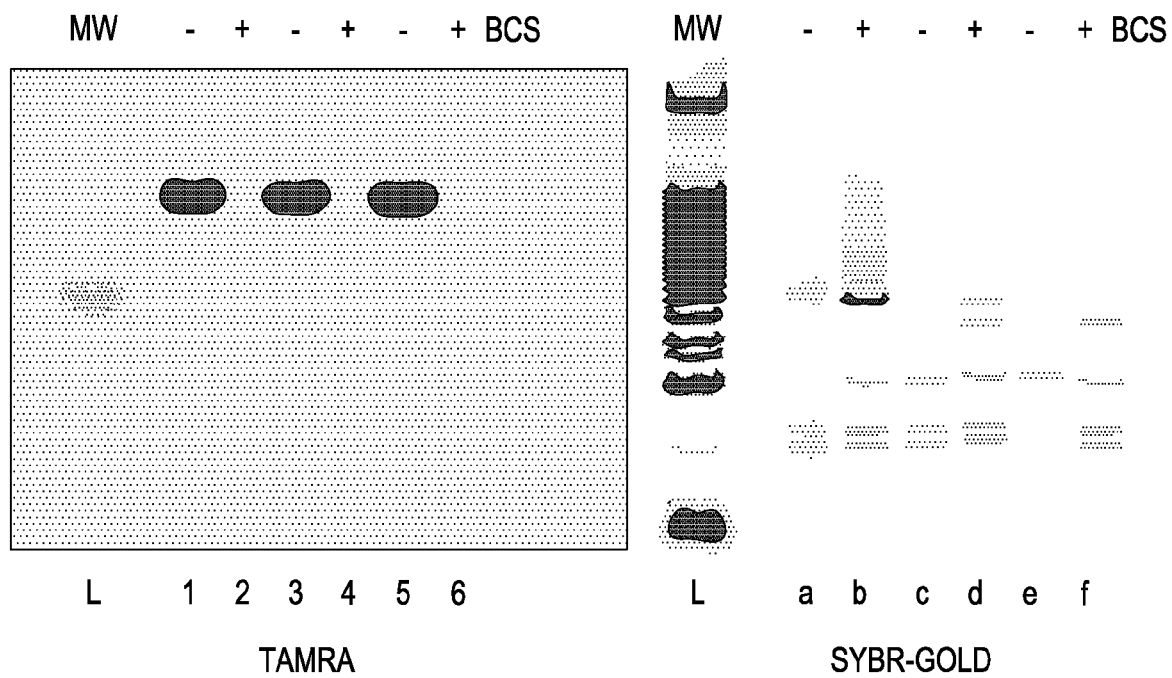

FIGS. 4 and 5 demonstrate that azido-dATP is incorporated by telomerase enzyme which is a reverse transcriptase (RNA dependent DNA polymerase), while FIG. 7 demonstrates that ethynyl-dUTP is also incorporated by telomerase enzyme. Thus, another aspect of methods using the modified nucleotides described herein is to detect products of RT-PCR using a nucleotide mixtures containing either an ethynyl or azido dNTP or enzymes such as reverse transcriptase and DNA polymerase. The product of such an experiment will be purified and then subjected to click based labeling method. The final labeled product can be purified either by precipitation or size exclusion chromatography. Additionally, the starting telomerase primer can be biotinylated allowing for purification of the telomerase modified product after the click reaction. The method is an example of first strand cDNA synthesis (RT-PCR).

Another aspect using the modified nucleotides described herein is "click" chemistry based oligonucleotide labeling for Fluorescene In-Situ Hybridization (FISH) and Chromogenic In-Situ Hybridization (CISH) and Silver In-situ Hybridization (SISH). In such methods, standard polymerases including, but not limited to, Klenow (Exo-), modified or wild type T7 DNA polymerase (Sequenase) or Bst polymerase (Large fragment) are used to amplify a template strand for a given sequence using primers as well as using ethynyl or azido dNTPs. The prepared DNA fragments can then be purified and subjected to the "click" reaction with either azido or alkyne labels, fluorescent labels, Qdots and nanoparticles to create a labeled probe. In certain embodiments, such probes are labeled using Staudinger Ligation, while in other embodiments such probes are labeled using activated alkyne reactions. Probes for methods like insitu hybridization can also be created using PCR and all of the commercially available PCR polymerases. Isothermal amplification of plasmids or bacterial artificial chromosomes (BAC) templates using phi29 DNA polymerase or other polymerases with strand displacement activity can also be done. In certain embodiments, labeling is done during a diagnostic or clinical assay. In other embodiments, such labeling in FISH and CISH is an automated in situ hybridization platforms where the hybridization can be followed by the click reaction to generate the signal. By way of example only, such automated systems are instruments from Dako, Ventana Medical Systems, and Vision Biosystems.

In another aspect RNA probes can be used for FISH and CISH, wherein such probes are labeled using "click" chemistry. In certain embodiments, such probes are labeled using Staudinger Ligation, while in other embodiments such probes are labeled using activated alkyne reactions. In certain embodiments, such RNA probes are prepared by the incorporation of modified nucleotides using in-vitro transcription system to generate an RNA probe. Alternative methods use small RNA oligonucleotides that can be labeled via aminoallyl —NHS ester chemistry. In certain embodiments, DNA dependent RNA polymerase from phage T7 or SP6 are used to incorporate alkyne modified oligonucleotide, by way of example only ethynyl oligonucleotides, or azido oligonucleotides to produce a modified RNA probe. Such modified RNA probes are the labeled with either azido or alkyne fluorescent or chromogenic labels using "click chemistry", thereby generating fluorogenic or chromogenic RNA probes.

Modifying Phosphoproteins Using Nucleotide Analogs

In another aspect, phosphoproteins can be modified in vivo or in vitro using alkyne or azide-tagged nucleotides whereby the azide or alkyne moiety is placed on the gamma phosphate of phosphoroproteins. By way of example only, such modifications can be accomplished by adding one of the nucleotides shown in FIG. 1 to a reaction mixture containing a protein kinase and a kinase target molecule. In certain embodiments, the phosphoprotein is an azide-containing phosphoroprotein that can be reacted under "click" chemistry conditions with an alkyne containing label including, but not limited to, fluorophores or affinity reagent for quantitation, visualization, or enrichment. In certain embodiments, the phosphoroprotein is an alkyne-containing phosphoroprotein that can be reacted under "click" chemistry conditions with an azide containing label including, but not limited to, fluorphores or affinity reagent for quantitation, visualization, or enrichment. In other embodiments, such modified phosphoroproteins can be used to form conjugates with a reporter molecule, a carrier molecule and/or a solid substrate.

In one aspect, modified nucleotide substrates containing azide or alkyne moieties are added directly to cultured cells for metabolic incorporation of the tagged gamma-phosphate molecule into cellular macromolecules including proteins. The process may involve treatment of the cells with pharmacological agents to detect alterations in phosphorylation dynamics. Entry of the compounds into live cultured cells could be enhanced by modifying the nucleotides with functional groups that would afford permeability, or by concomitant addition of cell permeablizing agents.

In another aspect, the kinase reaction could be performed in vitro using cellular extracts as the source of kinases and substrates. The modified nucleotides would be added to the reaction mixture and the reaction mixtures incubated with or without the addition of pharmacological agents of interest. The in vitro reaction may also entail adding an exogenous kinase or substrate source to the cellular extract along with the nucleotide analogs. In another application, the method could be used in vitro without cellular extracts, using purified kinases and kinase substrates. In certain embodiments, the kinase reaction can be conducted using kinase substrates deposited as an array on a solid substrate.

In each of these aspects the reaction mix may contain a buffer optimized for the particular kinase(s) of interest, a kinase source, a metal ion source, glycerol, nucleotide ATP analog, and ATP. The "click" detection reaction with an alkyne probe would be performed in the presence of copper (I), or copper(II) in the presence of a copper(II) reducing agent, a copper(I) chelating agent, and an appropriate buffer to maintaining optimal pH conditions.

In another aspect of methods using the modified nucleotides described herein is the preparation of Peptide-nucleic Acid (PNA) Conjugates using Click Chemistry, Staudinger Ligation or activated alkyne reactions. In such methods, a peptide with an O-GlcNac modification on one or more amino acids is subjected to a GalT1 reaction in the presence of UDP-GalNAz, resulting in an azido modified peptide. Such Post-Translational modifications have been described in the co-pending application entitled "Labeling of Glycoproteins" with Ser. No. 60/772,221, which is herein incorporated by reference in its entirety. In addition any post-translationally modified protein described in the co-pending application entitled "Labeling of Glcoproteins" with Ser. No. 60/772,221 can be used in the methods using modified nucleotide as described herein In certain embodiments, a peptide-nucleic acid conjugate is created by reacting the an azido-linked peptide with an alkynyl modified oligonucleotides under "click" chemistry reaction conditions. In certain embodiments, a peptide-nucleic acid conjugate is created by reacting the an azido-linked peptide with an alkynyl modified oligonucleotides in presence of 1 or 2 mM copper, 10 mM Sodium Ascorbate and 20 mM BCS. In certain embodiments, a peptide-nucleic acid conjugate is created by reacting the an azido-linked peptide with an ethynyl modified oligonucleotides under "click" chemistry reaction conditions. In certain embodiments, a peptide-nucleic acid conjugate is created by reacting the an azido-linked peptide with an ethynyl modified oligonucleotides in presence of 1 or 2 mM copper, 10 mM Sodium Ascorbate and 20 mM BCS.

In certain embodiments, a peptide-nucleic acid conjugate is created by reacting the an alkyne-linked peptide with an azide modified oligonucleotide under "click" chemistry reaction conditions. In certain embodiments, a peptide-nucleic acid conjugate is created by reacting the an alkyne-linked peptide with an azide modified oligonucleotide in presence of 1 or 2 mM copper, 10 mM Sodium Ascorbate and 20 mM BCS. In certain embodiments, a peptide-nucleic acid conjugate is created by reacting an ethynyl-linked peptide with an azide modified oligonucleotides under "click" chemistry reaction conditions. In certain embodiments, a peptide-nucleic acid conjugate is created by reacting the ethynyl-linked peptide with an azide modified oligonucleotides in presence of 1 or 2 mM copper, 10 mM Sodium Ascorbate and 20 mM BCS.

Samples and Sample Preparation

The end user will determine the choice of the sample and the way in which the sample is prepared. Samples that can be used with the methods and compositions described herein include, but are not limited to, any biological derived material or aqueous solution that contains a nucleic acid. In certain embodiments, a sample also includes material in which a nucleic acid has been added. The sample that can be used with the methods and compositions described herein can be a biological fluid including, but not limited to, whole blood, plasma, serum, nasal secretions, sputum, saliva, urine, sweat, transdermal exudates, cerebrospinal fluid, or the like. In other embodiments, the samples are biological fluids that include tissue and cell culture medium wherein nucleic acid of interest has been secreted into the medium. Cells used in such cultures include, but are not limited to, prokaryotic cells and eukaryotic cells that include primary cultures and immortalized cell lines. Such eukaryotic cells include, without limitation, ovary cells, epithelial cells, circulating immune cells, β cells, hepatocytes, and neurons. In certain embodiments, the sample may be whole organs, tissue or cells from an animal, including but not limited to, muscle, eye, skin, gonads, lymph nodes, heart, brain, lung, liver, kidney, spleen, thymus, pancreas, solid tumors, macrophages, mammary glands, mesothelium, and the like.

Various buffers can be used in the methods described herein, including inorganic and organic buffers. In certain embodiments the organic buffer is a zwitterionic buffer. By way of example only, buffers that can be used in the methods described herein include phosphate buffered saline (PBS), phosphate, succinate, citrate, borate, maleate, cacodylate, N-(2-Acetamido)iminodiacetic acid (ADA), 2-(N-morpholino)-ethanesulfonic acid (MES), N-(2-acetamido)-2-aminoethanesulfonic acid (ACES), piperazine-N,N'-2-ethanesulfonic acid (PIPES), 2-(N-morpholino)-2-hydroxypropanesulfonic acid (MOPSO), N,N-bis-(hydroxyethyl)-2-aminoethanesulfonic acid (BES), 3-(N-morpholino)-propanesulfonic acid (MOPS), N-tris-(hydroxymethyl)-2-ethanesulfonic acid (TES), N-2-hydroxyethyl-piperazine-N-2-ethanesulfonic acid (HEPES), 3-(N-tris-(hydroxymethyl)methylamino)-2-hydroxypropanesulfonic acid (TAPSO), 3-(N,N-Bis[2-hydroxyethyl]amino)-2-hydroxypropanesulfonic acid (DIPSO), N-(2-Hydroxyethyl)piperazine-N'-(2-hydroxypropanesulfonic acid) (HEPPSO), 4-(2-Hydroxyethyl)-1-piperazinepropanesulfonic acid (EPPS), N-[Tris(hydroxymethyl)methyl]glycine (Tricine), N,N-Bis(2-hydroxyethyl)glycine (Bicine), (2-Hydroxy-1,1-bis(hydroxymethyl)ethyl)amino]-1-propanesulfonic acid (TAPS), N-(1,1-Dimethyl-2-hydroxyethyl)-3-amino-2-hydroxypropanesulfonic acid (AMPSO), tris(hydroxy methyl)amino-methane (Tris), TRIS-Acetate-EDTA (TAE), glycine, bis[2-hydroxyethyl]iminotris[hydroxymethyl]methane (BisTris), or combinations thereof. In certain embodiments, wherein such buffers are used in gel electrophoresis separations the buffer can also include ethylene diamine tetraacetic acid (EDTA).

The concentration of such buffers used in the methods described herein is from about 0.1 mM to 1 M. In certain embodiments the concentration is between 10 mM to about 1 M. In certain embodiments the concentration is between about 20 mM and about 500 mM, and in other embodiments the concentration is between about 50 mM and about 300 mM. In certain embodiments, the buffer concentration is from about 0.1 mM to about 50 mM, while in other embodiments the buffer concentration if from about 0.5 mM to about 20 mM.

The pH will vary depending upon the particular assay system, generally within a readily determinable range wherein one or more of the sulfonic acid moieties is deprotonated.

In certain embodiments, buffers used in the methods described herein have a pH between 5 and 9 at ambient temperature. In certain embodiments the buffer has a pH between 6 and 8.5 at ambient temperature. In certain embodiments the buffer has a pH between 6 and 8 at ambient temperature. In certain embodiments the buffer has a pH between 6 and 7 at ambient temperature. In certain embodiments the buffer has a pH between 5 and 9 at 25° C. In certain embodiments the buffer has a pH between 6 and 8.5 at 25° C. In certain embodiments the buffer has a pH between 6 and 8 at 25° C. In certain embodiments the buffer has a pH between 6 and 7 at 25° C.

In certain embodiments, the samples used in the methods described herein have a non-ionic detergent to the sample. Non-limiting examples of such non-ionic detergents added to the samples used in the methods described herein are polyoxyalkylene diols, ethers of fatty alcohols including alcohol ethoxylates (Neodol from Shell Chemical Company and Tergitol from Union Carbide Corporation), alkyl phenol ethoxylates (Igepal surfactants from General Aniline and Film Corporation), ethylene oxide/propylene oxide block copolymers (PLURONIC™ Series from BASF Wyandotte Corporation), polyoxyethylene ester of a fatty acids (Stearox CD from Monsanto Company), alkyl phenol surfactants (Triton series, including Triton X-100 from Rohm and Haas Company), polyoxyethylene mercaptan analogs of alcohol ethoxylates (Nonic 218 and Stearox SK from Monsanto Company), polyoxyethylene adducts of alkyl amines (Ethoduomeen and Ethomeen surfactants from Armak Company), polyoxyethylene alkyl amides, sorbitan esters (such as sorbitan monolaurate) and alcohol phenol ethoxylate (Surfonic from Jefferson Chemical Company, Inc.). Non-limiting examples of sorbitan esters include polyoxyethylene(20) sorbitan monolaurate (TWEEN20), polyoxyethylene(20) sorbitan monopalmitate (TWEEN40), polyoxyethylene(20) sorbitan monostearate (TWEEN60) and polyoxyethylene(20) sorbitan monooleate (TWEEN 80). In certain embodiments, the concentration of such non-ionic detergents added to a sample is from 0.01 to 0.5%. In other embodiments the concentration is from about 0.01 to 0.4 vol. %. In other embodiments the concentration is from about 0.01 to 0.3 vol. %. In other embodiments the concentration is from about 0.01 to 0.2 vol. %. In other embodiments the concentration is from about 0.01 to 0.1 vol. %.

Illumination

The compounds and compositions described herein may, at any time before, after or during an assay, be illuminated with a wavelength of light that results in a detectable optical response, and observed with a means for detecting the optical response. In certain embodiments, such illumination can be by a violet or visible wavelength emission lamp, an arc lamp, a laser, or even sunlight or ordinary room light, wherein the wavelength of such sources overlap the absorption spectrum of a fluorophore or chromaphore of the compounds or compositions described herein. In certain embodiments, such illumination can be by a violet or visible wavelength emission lamp, an arc lamp, a laser, or even sunlight or ordinary room light, wherein the fluorescent compounds, including those bound to the complementary specific binding pair member, display intense visible absorption as well as fluorescence emission.

In certain embodiments, the sources used for illuminating the fluorophore or chromophore of the compounds or compositions described herein include, but are not limited to, hand-held ultraviolet lamps, mercury arc lamps, xenon lamps, argon lasers, laser diodes, blue laser diodes, and YAG lasers. These illumination sources are optionally integrated into laser scanners, flow cytometer, fluorescence microplate readers, standard or mini fluorometers, or chromatographic detectors. The fluorescence emission of such fluorophores is optionally detected by visual inspection, or by use of any of the following devices: CCD cameras, video cameras, photographic film, laser scanning devices, fluorometers, photodiodes, photodiode arrays, quantum counters, epifluorescence microscopes, scanning microscopes, flow cytometers, fluorescence microplate readers, or by means for amplifying the signal such as photomultiplier tubes. Where the sample is examined using a flow cytometer, a fluorescence microscope or a fluorometer, the instrument is optionally used to distinguish and discriminate between the fluorescent compounds of the invention and a second fluorophore with detectably different optical properties, typically by distinguishing the fluorescence response of the fluorescent compounds of the invention from that of the second fluorophore. Where a sample is examined using a flow cytometer, examination of the sample optionally includes isolation of particles within the sample based on the fluorescence response by using a sorting device.

In certain embodiments, fluorescence is optionally quenched using either physical or chemical quenching agents. Examples of quenching moieties include, but are not limited to DABCYL (i.e., 4-(4'-dimethylaminophenylazo)-benzoic acid) succinimidyl ester, diarylrhodamine carboxylic acid, succinimidyl ester (or QSY-7), and 4',5'-dinitrofluorescein carboxylic acid, succinimidyl ester (or QSY-33) (all available, for example, from Molecular Probes), quencher1 (Q1; available from Epoch Biosciences, Bothell, Wash.), or "Black hole quenchers" BHQ-1, BHQ-2, and BHQ-3 (available from BioSearch Technologies, Inc., Novato, Calif.).

Kits of the Invention

In another aspect, the present invention provides kits that include $N_3$-dATP, an enzyme; an azide reactive reporter molecule, carrier molecule or solid support.

In one aspect, the invention includes a kit for labeling a nucleic acid that includes at least one label that comprises a terminal alkyne, a solution comprising copper, and a solution that comprises a copper (I) chelator. The kit can further comprise a solution that comprises a reducing agent, one or more buffers, or one or more detergents.

In one embodiment, an alkyne label provided in a kit is a fluorophore, such as, but not limited to, a xanthene, coumarin, borapolyazaindacene, pyrene and cyanine. In one embodiment, a kit provides two or more different terminal alkyne-containing labels one or more of which is a fluorophore, In other embodiments, an alkyne label provided in a kit is a tag, such as but not limited to a peptide or a hapten, such as biotin.

In preferred embodiments, a copper (I) chelator provided in the kit is a 1,10 phenanthroline, preferably bathocuproine disulfonic acid. In some embodiments, copper is provided in the form of a copper sulfate or copper acetate solution. In some embodiments, a reducing agent is provided in the form of ascorbate.

In another aspect, the invention includes a kit for labeling a nucleic acid that includes at least one label that comprises an azido group, a solution comprising copper, an a solution that comprises a copper (I) chelator. The kit can further comprise a solution that comprises a reducing agent, one or more buffers, or one or more detergents.

In one embodiment of this aspect, an azido-containing label provided in a kit is a fluorophore, such as, but not limited to, a xanthene, coumarin, borapolyazaindacene, pyrene and cyanine. In other embodiments, an azido label provided in a kit is a tag, such as but not limited to a peptide or a hapten, such as biotin.

In one embodiment, a kit provides two or more different azido-containing labels one or more of which is a fluorophore, In preferred embodiments, a copper (I) chelator provided in the kit is a 1,10 phenanthroline, preferably bathocuproine disulfonic acid. In some embodiments, copper is provided in the form of a copper sulfate or copper acetate solution. In some embodiments, a reducing agent is provided in the form of ascorbate.

A detailed description of the invention having been provided above, the following examples are given for the purpose of illustrating the invention and shall not be construed as being a limitation on the scope of the invention or claims.

EXAMPLES

Example 1

Telomerase Assay with $N_3$-dUTP and $N_3$-dATP

TRAPeze™ TELOMERASE assays (Chemicon Kit S7700) were performed with $N_3$-dUTP and $N_3$-dATP. Each reaction contained the following:
(a) 1×TRAP reaction buffer (20 mM Tris-HCl, pH 8.3, 1.5 $MgCl_2$ 63 mM KCl, 0.05% Tween 20, 1 mM EGTA)
(b) 50 μM of different combinations of deoxynucleoside triphosphates (see Table 1 for details)
(c) 1 μl of TS primer (TRAPeze Telomerase Kit, Chemicon)
(d) 1 μl of Primer Mix (contains three separate primers—a K1 Fwd primer, RP Rev Primer and TSK 1 internal control primer from the (TRAPeze Telomerase Kit, Chemicon)
(e) 2 units of Taq DNA polymerase
(f) 2 μl of positive control cells (500 cells) of the TRAPeze Telomerase Kit (Chemicon). The cell extract was prepared and further diluted in CHAPS buffer, the components of which were 10 mM Tris-HCl pH 7.5, 1 mM $MgCl_2$, 1 mM EGTA, 0.1 mM Benzamidine, 5 mm β-mercaptoethanol, 0.5% CHAPS and 10% Glycerol.
(g) PCR grade water as required to bring the volume of each reaction to 50 μl.

The reaction was carried out in an Applied Biosystems PCR instrument under the following conditions: 30° C.—30 minutes—hold 32 cycles of 95° C.—30 sec
59° C.—30 sec
72° C.—1 minute
Followed by: 4° C.—infinity The reactions were pulled out, mixed with TRACK—IT Cyan orange loading dye. The reactions labeled 1, 2, 3, 4 (see FIG. 4 and Table 1) were subjected to a 4-20% Tri Borate EDTA—polyacrylamide gel. The gel was run at 10V for 10 minutes; 190V for 90 minutes. The gel was then pulled out of the cassette and stained with 1:10,000 fold dilution of stock SYBR GOLD in TBE for 20-30 minutes and then scanned for a signal (Ex: 473, Em: 520).

The results of the amplification are shown in FIG. 4, and the listing of the dNTP combinations in each reaction (gel lane) is given in Table 1.

TABLE 1

| dNTP combinations in the reactions | |
|---|---|
| Lanes (in gel) | dNTPs |
| 1 | 50 μM of dATP dTTP, dCTP, and dGTP. |
| 2 | 50 μM of $N_3$-dUTP, dATP, dCTP, and dGTP |
| 3 | 50 μM of $N_3$-dATP, dATP, dCTP, and dGTP |
| 4 | 50 μM of $N_3$-dUTP, $N_3$-dATP, dCTP, and dGTP |

The left most lane labeled "L" on the gel is a 10 bp ss DNA ladder (200 ng per lane).

From FIG. 4 it is seen that $N_3$-dUTP is incorporated by Taq polymerase (lane 2), and that $N_3$-dATP is incorporated both by telomerase and Taq polymerase (lane 3).

Example 2

Dose-Dependence of Telomerase Assay with $N_3$-dUTP and $N_3$-dATP

TRAPeze™ TELOMERASE assays (Chemicon Kit S7700) were performed with $N_3$-dUTP and $N_3$-dATP. Each reaction contained the following:
(a) 1×TRAP reaction buffer (20 mM Tris-HCl, pH 8.3, 1.5 $MgCl_2$ 63 mM KCl, 0.05% Tween 20, 1 mM EGTA)
(b) 50 μM of deoxynucleoside triphosphates (see Table 2 for details)
(c) 1 μl of TS primer (TRAPeze Telomerase Kit, Chemicon)
(d) 1 μl of Primer Mix (contains three separate primers—a K1 Fwd primer, RP Rev Primer and TSK 1 internal control primer from the (TRAPeze Telomerase Kit, Chemicon)
(e) 2 units of Taq DNA polymerase
(f) 2 μl of positive control cells (500 cells) of the TRAPeze Telomerase Kit (Chemicon). The cell extract was prepared and further diluted in CHAPS buffer, the components of which were 10 mM Tris-HCl pH 7.5, 1 mM $MgCl_2$, 1 mM EGTA, 0.1 mM Benzamidine, 5 mm β-mercaptoethanol, 0.5% CHAPS, and 10% Glycerol
(g) PCR grade water as required to bring the volume of each reaction to 50 μl.

The reaction was carried out in an Applied Biosystems PCR instrument under the following conditions: 30° C.—30 minutes—hold (At the end of the 30 minute Telomerase reaction, appropriate volumes of azido-dNTPs were added to bring the final concentration to 50 μM. The PCR step was then carried out after that)

32 cycles of 95° C.—30 sec
   59° C.—30 sec
   72° C.—1 minute
   Followed by: 4° C.—infinity The reactions were pulled out, mixed with TRACK—IT Cyan orange loading dye. The reactions labeled 1, 2, 3, 4 (see FIG. 5 and Table 2) were subjected to a 4-20% Tris Borate EDTA—polyacrylamide gel. The gel was run at 10V for 10 minutes; 190V for 90 minutes. The gel was then pulled out of the cassette and stained with 1:10,000 fold dilution of stock SYBR GOLD in TBE for 20-30 minutes and then scanned for a signal (Ex: 473, Em: 520).

The results of the amplification are shown in FIG. 5, and the listing of the dNTP combinations in each reaction (gel lane) is given in Table 2.

TABLE 2 dNTP combinations in the reactions

| Lanes (in gel) | dNTPs |
|---|---|
| 1 | 50 μM of dATP, dTTP, dCTP, and dGTP. |
| 2 | 50 μM $N_3$-dUTP, dATP, dCTP, and dGTP |
| 3 | 10 μM $N_3$-dUTP, 50 μM dATP, dCTP, and dGTP |
| 4 | 1 μM $N_3$-dUTP, 50 μM dATP, dCTP, and dGTP |
| 5 | 0.1 μM $N_3$-dUTP, 50 μM dATP, dCTP, and dGTP |
| 6 | 50 μM $N_3$-dATP, dTTP, dCTP, and dGTP |
| 7 | 10 μM $N_3$-dATP, 50 μM dATP, dCTP, and dGTP |
| 8 | 1 μM $N_3$-dATP, 50 μM dATP, dCTP, and dGTP |
| 9 | 0.1 μM $N_3$-dATP, 50 μM dATP, dCTP, and dGTP |

The left most lane labeled "L" on the gel is a 10 bp ss DNA ladder (200 ng per lane).

From FIG. 5 it is seen that $N_3$-dUTP is not incorporated by the Telomerase enzyme within a range of 100 nM to 50 micro molar, but it is incorporated by Taq polymerase (lane 2-5). However, $N_3$-dATP is incorporated both by telomerase and Taq polymerase (lanes 6-9).

Example 3

"Click"-Chemistry Based Telomerase Activity Assay: -Dose-Dependence of Telomerase Assay with $N_3$-dATP TRAPeze™ TELOMERASE assays (Chemicon Kit S7700) were performed with $N_3$-dATP. Each reaction contained the following:
(a) 1×TRAP reaction buffer (20 mM Tris-HCl, pH 8.3, 1.5 MgCl$_2$ 63 mM KCl, 0.05% Tween 20, 1 mM EGTA)
(b) 50 μM of different combinations of deoxynucleoside triphosphates (see Table 3 for details)
(c) 1 μl of TS primer (TRAPeze Telomerase Kit, Chemicon)
(d) 1 μl of Primer Mix (contains three separate primers—a K1 Fwd primer, RP Rev Primer and TSK 1 internal control primer from the (TRAPeze Telomerase Kit, Chemicon)
(e) 2 units of Taq DNA polymerase
(f) 2 μl of positive control cells (500 cells) of the TRAPeze Telomerase Kit Chemicon). The cell extract was prepared and further diluted in CHAPS buffer, the components of which were 10 mM Tris-HCl pH 7.5, 1 mM MgCl$_2$, 1 mM EGTA, 0.1 mM Benzamidine, 5 mm β-mercaptoethanol, 0.5% CHAPS, and 10% Glycerol
(g) PCR grade water as required to bring the volume of each reaction to 50 μl.

The reaction was carried out in an Applied Biosystems PCR instrument under the following conditions: 30° C.—30 minutes—hold
   32 cycles of 95° C.—30 sec
   59° C.—30 sec
   72° C.—1 minute
   Followed by: 4° C.—infinity The reactions were cleaned through size exclusion columns (Chromaspin TE30, Clonetech). The eluate was then subjected to click reaction using a final concentration of 25% propylene glycol; 1 mM copper sulfate; 10 mM bathocuproinedisulfonic acid (BCS), 10 mM Sodium Ascorbate and 50 μM alkyne-TAMRA. The reaction was performed for 30 minutes at room temperature. This was followed by clean up on a size exclusion as described above. The reactions were pulled out, mixed with the TRACK—IT Cyan orange loading dye. The reactions (see FIG. 6 and Table 3) were subjected to a 20% TBE—polyacrylamide gel. The gel was run at 10V for 10 minutes; 190V for 90 minutes. The gel was pulled out of the cassette and scanned for TAMRA (Ex: 530 nm Em: 580 nm). The same gel was then stained with SYBR GOLD for 30 minutes and then scanned as described above.

Figure 6:
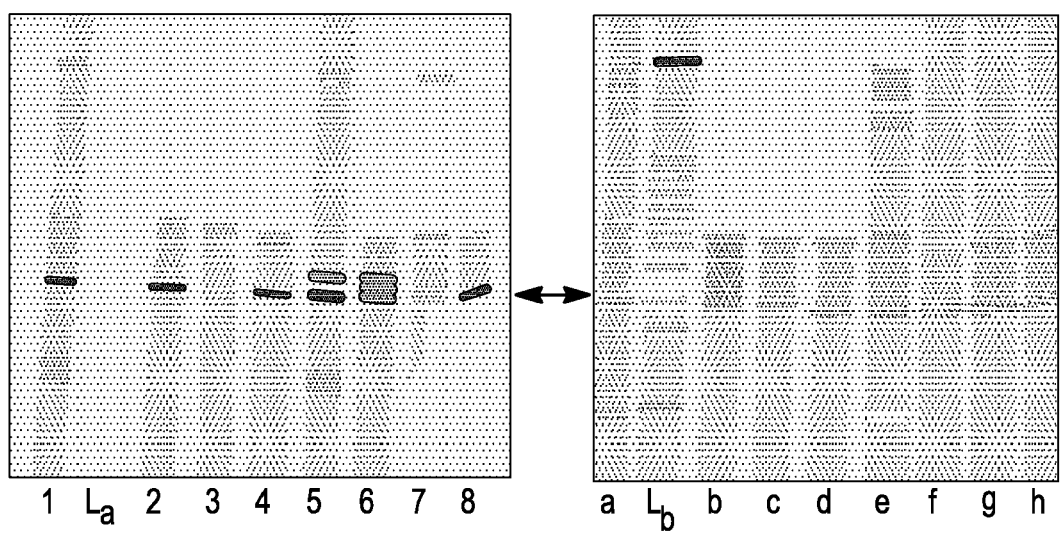

The results of the amplification are shown in FIG. 6, and the listing of the dNTP combinations in each reaction (gel lane) is given in Table 3.

TABLE 3 dNTP combinations in the reactions

| Lanes (in gel) | dNTPs |
|---|---|
| 1 or a | 50 μM of dATP, dTTP, dCTP, and dGTP. |
| 2 or b | 50 μM of dATP, dTTP, dCTP, and dGTP |
| 3 or c | 10 μM $N_3$-dATP + 40 μM dATP, 50 μM dATP, dCTP, and dGTP |
| 4 or d | 30 μM dATP + 20 μM $N_3$-dATP, 50 μM dTTP, dCTP, and dGTP |
| 5 or e | 25 μM dATP + 25 μM $N_3$-dATP, 50 μM dTTP, dCTP, and dGTP |
| 6 or f | 20 μM dATP + 30 μM $N_3$-dATP, 50 μM dTTP, dCTP, and dGTP |
| 7 or g | 10 μM dATP + 40 μM $N_3$-dATP, 50 μM dTTP, dCTP, and dGTP |
| 8 or h | 50 μM $N_3$-dATP, 50 μM dTTP, dCTP, and dGTP |

The left most lane labeled "L" on the gel is a 10 bp ss DNA ladder (200 ng per lane).

From FIG. 6 it is seen that there is a dose dependence of the "click" reaction with the best signal coming from the 100% 50 μM of $N_3$-dATP. Also the PCR reaction with 50 μM of $N_3$-dATP was not as efficient.

Example 4

"Click"-Chemistry Based Telomerase Activity Assay: -Dose-Dependence of Telomerase Assay with E-dUTP TRAPeze TELOMERASE assays (Chemicon Kit S7700) were performed with ethynyl-dUTP. Each reaction contained the following:
(a) 1×TRAP reaction buffer (20 mM Tris-HCl, pH 8.3, 1.5 MgCl$_2$ 63 mM KCl, 0.05% Tween 20, 1 mM EGTA)
(b) 50 μM of different combinations of deoxynucleoside triphosphates (see Table 4 for details)
(c) 1 μl of TS primer (TRAPeze Telomerase Kit, Chemicon)

(d) 1 µl of Primer Mix (contains three separate primers—a K1 Fwd primer, RP Rev Primer and TSK 1 internal control primer from the (TRAPeze Telomerase Kit, Chemicon)

(e) 2 units of Taq DNA polymerase (f) 2 µl of positive control cells (500 cells) of the TRAPeze Telomerase Kit (Chemicon). The cell extract was prepared and further diluted in CHAPS buffer, the components of which were 10 mM Tris-HCl pH 7.5, 1 mM $MgCl_2$, 1 mM EGTA, 0.1 mM Benzamidine, 5 mm β-mercaptoethanol, 0.5% CHAPS, and 10% Glycerol (g) PCR grade water as required to bring the volume of each reaction to 50 µl.

The reaction was carried out in an Applied Biosystems PCR instrument under the following conditions: 30° C.—30 minutes—hold 32 cycles of 95° C.—30 sec 59° C.—30 sec 72° C.—1 minute Followed by: 4° C.—infinity The reactions were cleaned through size exclusion columns (Chromaspin TE30, Clonetech). The eluate was then subjected to click reaction using a final concentration of 25% propylene glycol; 1 mM copper sulfate; 10 mM BCS, 10 mM Sodium Ascorbate and 50 µM azido-TAMRA. The reaction was performed for 30 minutes at room temperature. This was followed by clean up on a size exclusion as described above. The reactions were pulled out, mixed with the TRACK—IT Cyan orange loading dye. The reactions (see FIG. 7 and Table 4) were subjected to a 20% TBE—polyacrylamide gel. The gel was run at 10V for 10 minutes; 190V for 90 minutes. The gel was pulled out of the cassette and scanned for TAMRA (Ex: 530 nm Em: 580 nm). The same gel was then stained with SYBR GOLD for 30 minutes and then scanned as described above.

The results of the amplification are shown in FIG. 7, and the listing of the dNTP combinations in each reaction (gel lane) is given in Table 4.

TABLE 4 dNTP combinations in the reactions

| Lanes (in gel) | dNTPs |
|---|---|
| 1 or A | 50 µM of dATP, dTTP, dCTP, and dGTP. |
| 2 or B | 50 µM of dATP, dTTP, dCTP, and dGTP |
| 3 or C | 40 µM dTTP + 10 µM e-dUTP, 50 µM dATP, dCTP, and dGTP |
| 4 or D | 30 µM dTTP + 20 µM e-dUTP, 50 µM dATP, dCTP, and dGTP |
| 5 or E | 25 µM dTTP + 25 µM e-dUTP, 50 µM dATP, dCTP, and dGTP |
| 6 or F | 20 µM dTTP + 30 µM e-dUTP, 50 µM dATP, dCTP, and dGTP |
| 7 or G | 10 µM dTTP + 40 µM e-dUTP, 50 µM dATP, dCTP, and dGTP |
| 8 or H | 50 µM e-dUTP, 50 µM dTTP, dCTP, and dGTP |

The left most lane labeled "L" on the gel is the 10 bp ss DNA ladder (200 ng per lane).

From FIG. 7 it is seen that there is a dose dependence of the click reaction with the best signal coming from the 100% 50 µM of $N_3$-dATP. Also the PCR reaction with 50 µM of E-dUTP was as efficient as with natural dNTPs.

Example 5

PCR Incorporation and Detection of Azide or Alkyne Nucleic Acids

The reaction was carried out in an Applied Biosystems PCR instrument under the following conditions: 30° C.—30 minutes—hold 32 cycles of 95° C.—30 sec 59° C.—30 sec 72° C.—1 minute Followed by: 4° C.—infinity In addition, PCR was preformed with Taq and Pfu-turbo DNA polymerase. Briefly, a 1 pmol of either a 36 (lane 1/5/1/f) or 38 (lanes 2/6/b/g) or 44 (lanes 3/7/c/h) or 60 bp (lanes 4/8/d/l) amplicon was amplified by PCR using 10 nmolar forward and reverse Primer, 50 µM modified dNTPs (e-dUTP, dTTP, dCTP, and dGTP), 1×Taq or Pfu Turbo buffer and 1.5 mM MgCl2 (for Taq polymerase).

The reactions were cleaned through size exclusion columns (Chromaspin TE30, Clonetech). The eluate was then subjected to click reaction using a final concentration of 25% propylene glycol; 1 mM copper sulfate; 10 mM BCS, 10 mM Sodium Ascorbate and 50 µM azido-TAMRA or 50 µM alkyne-TAMRA. The reaction was performed for 30 minutes at room temperature. This was followed by clean up on a size exclusion as described above. The reactions were pulled out, mixed with the TRACK—IT Cyan orange loading dye. The reactions (see FIG. 8 and Table 4) were subjected to a 20% TBE—polyacrylamide gel. The gel was run at 10V for 10 minutes; 190V for 90 minutes. The gel was pulled out of the cassette and scanned for TAMRA (Ex: 530 nm Em: 580 nm). The same gel was then stained with SYBR GOLD for 30 minutes and then scanned as described above.

FIG. 8 shows a 20% TBE PAGE that has been scanned for TAMRA (left; Ex 532-Em 580) followed by staining with SYBR GOLD (right). Lanes 1, 2, 3 and 4 (or a, b, c, d) have been loaded with 2 ul of the PCR product while lanes 5, 6, 7 and 8 (or f, g, h, 1, k) have been loaded with 6 ul of the PCR product. The fact that one can see ladders or the 36 bp internal control band in a TRAP assay indicates that not only can Telomerase incorporate azido or alkyne modified compounds but Taq polymerase can also do the same, since the subsequent step in TRAP assay after Telomerase reaction is the PCR step.

Example 6

Incorporation of E-dUTP in an Isothermal Extension Assay Using Different Polymerases Single stranded DNA oligomers shown below were used for a primer extension assay using "clickable" dNTPs. The oligos used were designed to titrate the dUTP in the sequence.

```
Oligo 3
                                              (SEQ ID NO: 1)
5'-
TTAGGGTTAGGGTTAGGGTTTGGGTTTGGGTTTGGGTTTGGGTTTGGGTT
TGGGCTGGCCGTCGTTTTAC Oligo 4
                                              (SEQ ID NO:2)
5'-
TTTGGGTTTGGGTTTGGGTTTGGGTTTGGGTTTGGGTTTGGGTTAGGGTTTGGGTT
TGGGCTGGCCGTCGTTTTAC
```

M13 Primer for Annealing at the End of all of these Oligos

5'-GTAAAACGACGGCCAG-3' (SEQ ID NO: 3)

100 pmol of Oligo 3 or 4 were annealed with the 500 pmol M13 primer in an annealing buffer (7 mM Tris-HCl pH 7.5, 2.5 mM MgCl2, 20 mM NaCl). The reaction mix was heated up to 95 C for 5 minutes, 20 minutes at 65 C and then cooled to ambient temperatures. All the reactions were supplied with 50 uM dNTPs each. The dNTP mix consisted of 50 uM of e-dUTP, dATP, dGTP, dCTP each. The reaction was initiated by addition of the polymerase. Details of the different reactions are given in Table 5:

TABLE 5

| Lane | Oligo | polymerase | Conditions of experiment |
|---|---|---|---|
| 1 or a | O3 | Klenow (Exo –ve) | Annealing buffer/30' @37 C. |
| 2 or b | O3 | Taq polymerase | 1 × TS buffer (1.5 mM MgCl2)/30' @72 C. for 30, in a dry bath |
| 3 or c | O3 | Pfu (Turbo) | 1 × Pfu turbo buffer/95 C. for 30 seconds; 59 C. for 1 minute; 72 C. for 2' in an applied biosystems PCR instrument |
| 4 or d | O3 | Taq polymerase | 1 × annealing buffer (2.5 mM MgCl2)/same conditions as for reaction 3 |
| 5 or e | O4 | Klenow (Exo –ve) | Annealing buffer/30' @37 C. |
| 6 or f | O4 | Taq polymerase | 1 × TS buffer (1.5 mM MgCl2)/30' @72 C. for 30, in a dry bath |
| 7 or g | O4 | Pfu (Turbo) | 1 × Pfu turbo buffer/95 C. for 30 seconds; 59 C. for 1 minute; 72 C. for 2' in an applied biosystems PCR instrument |
| 8 or h | O4 | Pfu (Turbo) | 1 × Pfu turbo buffer/95 C. for 30 seconds; 59 C. for 1 minute; 72 C. for 2' in an applied biosystems PCR instrument |

Lanes designated $L_a$ and $L_b$ are the 25 bp DNA ladder.

The extended dsDNA product was subjected to a "click" reaction. The volume of the reaction product was brought to 25 of 50 ul. The final concentrations of the reaction components were 25% propylene glycol, 1 mM Copper (II), 10 mM Sodium Ascorbate, 10 mM BCS and 50 uM azido-TAMRA. The reactions were rocked on a tube shaker for 30-60 minutes at room temperature. The contents of the tube were then subjected to size exclusion chromatography using Chroamspin columns. The purified ds DNA was then mixed with 1/10 volume of 10× blue juice and loaded on to a 2-% TBE PAGE which was run at constant 200V for 2 hours.

After completion of the run the gel was scanned for TAMRA (Ex: 530 nm and Em 580 nm), the results of which are shown on the left part of FIG. 9. After scanning for TAMRA the gel was stained with 1:10,000 fold dilution of SYBR GOLD in 1×TBE and scanned for signal (Ex: 473 Em: 580) shown on the right.

Example 7

Incorporation of Cu(I) Chelator BCS to Preserve TrAP Laddering

TRAPeze TELOMERASE assays (Chemicon Kit S7700) were performed with BCS. Each reaction contained the following:
(a) 1×TRAP reaction buffer (20 mM Tris-HCl, pH 8.3, 1.5 mM MgCl$_2$ 63 mM KCl, 0.05% Tween 20, 1 mM EGTA)
(b) 50 of N$_3$-dATP+50 μM of dGTP, dCTP, dTTP. (see Table 6 for details)
(c) 1 μl of TS primer (TRAPeze Telomerase Kit, Chemicon)
(d) 1 μl of Primer Mix (contains three separate primers—a K1 Fwd primer, RP Rev Primer and TSK 1 internal control primer from the (TRAPeze Telomerase Kit, Chemicon)
(e) 2 units of Taq DNA polymerase
(f) 2 μl of positive control cells (500 cells) of the TRAPeze Telomerase Kit (Chemicon). The cell extract was prepared and further diluted in CHAPS buffer, the components of which were 10 mM Tris-HCl pH 7.5, 1 mM MgCl$_2$, 1 mM EGTA, 0.1 mM Benzamidine, 5 mm β-mercaptoethanol, 0.5% CHAPS and 10% Glycerol.
(g) PCR grade water as required to bring the volume of each reaction to 50 μl.

The reaction was carried out in an Applied Biosystems PCR instrument under the following conditions: 30° C.—30 minutes—hold
32 cycles of 95° C.—30 sec
59° C.—30 sec
72° C.—1 minute
Followed by: 4° C.—infinity The reactions were cleaned through size exclusion columns (Chromaspin TE30, Clonetech). The eluate was then subjected to click reaction using a final concentration of 25% propylene glycol; 1 mM copper sulfate; in presence or absence of 10 mM BCS (see Table 6), 10 mM Sodium Ascorbate and 50 μM alkyne-TAMRA. The reaction was performed for 30 minutes at room temperature. This was followed by clean up on the size exclusion as described above. The reactions were mixed with the TRACK—IT Cyan orange loading dye and were subjected to a 20% TBE—polyacrylamide gel (see FIG. 10). The gel was run at 10V for 10 minutes; 190V for 90 minutes. The gel was pulled out of the cassette and scanned for TAMRA (Ex: 530 nm Em: 580 nm). The same gel was then stained with SYBR GOLD for 30 minutes and then scanned with an excitation source at 473 nm and emission at 520 nm.

TABLE 6

| Lane | Telomerase | Chelator for click labeling | Comments |
|---|---|---|---|
| 1 or a | 500 cells (Telomerase +ve) | none | All other components of the click reaction are as described |
| 2 or b | 500 cells (Telomerase +ve) | 10 mM BCS | |
| 3 or c | 500 cells (Telomerase –ve) | None | Sau 3 cells do not express Telomerase. |
| 4 or d | 500 cells (Telomerase –ve) | 10 mM BCS | |
| 5 or e | Heat inactivated cells | None | Telomerase enzyme is sensitive to heat. Heating the +ve control cells for 10 minutes at 80 C. destroys telomerase activity. |
| 6 or f | Heat inactivated cells | 10 mM BCS | |

The results of the amplification are shown in FIG. 10, where the gel shows a high molecular weight product that appears in the absence of BCS irrespective of the activity of Telomerase. However, the TRAP "laddering" pattern of the assay product is restored upon addition of the BCS.

Example 8

Figure 11:
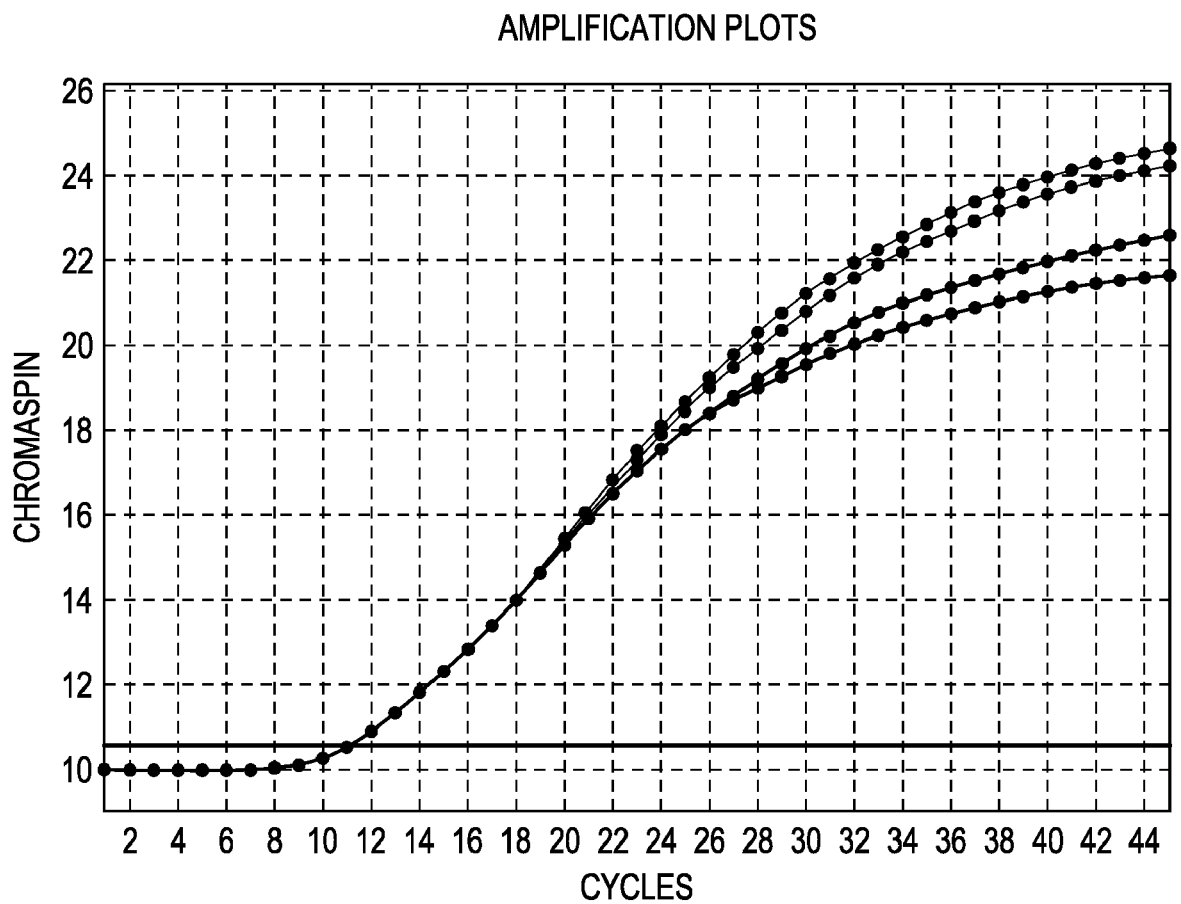

Click Chemistry Based Detection of Amplified DNA Products Using Isothermal DNA Amplification Technology-Helicase Dependent Amplification (See FIG. 11)

8a) Helicase Dependent Amplification (See FIG. 11)
a. mHDA: A mixture of DNA Helicase, a DNA polymerase, deoxyoligonucleotide primers and deoxynucleotide triphosphates with either: (1) an azido-dATP or an ethylene-dUTP (in place of dTTP) or (2) an azido-dUTP or ethylene-dUTP in addition to the four dNTPs are added together. The reaction mixture is heated to 95° C. for 5 minutes followed by incubation of the reaction mix at 37° C. for 1 to 3 hours depending upon the length of the target and amount of final product required.

After completion the polymerase reaction is complete, Click reaction components are added to the amplified DNA. The click reaction components are CuSo4, BCS, Na-Ascorbate and either an azido-fluorophore or an alkyne-fluorophore. The reaction is then run directly on an agarose gel or detected using a secondary matrix.

8b) b. tHDA: A mixture of DNA Helicase, Bst DNA polymerase (from *Bacillus stearoethermophillus*), deoxyoligonucleotide primers and deoxynucleotide triphosphates with either: (1) an azido-dATP or an ethylene-dUTP (in place of dTTP) or (2) an azido-dUTP or ethylene-dUTP in addition to the four dNTPs are added together. The reaction mixture is heated to 95° C. for 5 minutes followed by incubation of the reaction mix at 65° C. for 1 to 2 hours depending upon the length of the target and amount of final product required.

After completion the polymerase reaction is complete, Click reaction components are added to the amplified DNA. The click reaction components are $CuSO_4$, BCS, Na-Ascorbate and either an azido-fluorophore or an alkyne-fluorophore. The reaction is then run directly on an agarose gel.

c. Circular HDA: This method of DNA amplification uses T7 Helicase and T7DNA polymerase and is similar to rolling circle DNA amplification. Other accessory proteins in this platform include T7 single strand DNA binding protein. This platform can be used for in vitro amplification of plasmid or covalent closed circular DNA. This technology has significant use in clinical diagnostics and molecular biology e.g., in DNA sequencing and mutagenesis. As described above azido or alkyne modified nucleotides triphosphates are used during the DNA amplification methods and then either the alkyne or azido dye molecules are added to create a label on the newly synthesized DNA.

d. rt-HDA: this method takes advantage of the reverse transcriptase activity of reverse transcriptase under constant temperature conditions combined with polymerase activity of Bst polymerase. Detection of the amplified DNA is performed as described above using an azido or alkyne dNTPs and azido/alkyne dyes are added at the end of the amplification reaction under conditions that promote a Click reaction between the modified dNTP and the dye label.

Strand Displacement Amplification (SDA) (see FIG. 12):

SDA is an isothermal nucleic acid amplification method. Primer containing a restriction site is annealed to template. Amplification primers are then annealed to 5' adjacent sequences (form a nick) and amplification is started at a fixed temperature. Newly synthesized DNA are nicked by a restriction enzyme, polymerase starts amplification again, displacing the newly synthesized strands. One hundred and nine copies of DNA can be made in one reaction. For better labeling and detection of the amplified product, an azido or alkyne dUTP is added which will be incorporated into the newly synthesized strand because the enzyme is a member of a family of pol I DNA polymerases which have been shown in the art to incorporate azido or alkyne modified dNTPs using Taq polymerase. Once the amplification reaction is finished, the azido or alkyne dNTP in the polymerized strand is ligated to an azido or alkyne dye under conditions that will promote the Click reaction.

Loop Mediated Isothermal DNA Amplification:

LAMP (Loop-mediated Isothermal Amplification) method is a nucleic acid amplification method that uses 4 primers, which recognize 6 distinct regions on the target gene and a DNA polymerase with strand displacement activity to carry out reaction under isothermal condition. Amplification and detection of a gene can be completed in a single step, by incubating the mixture of samples, primers, DNA polymerase with strand displacement activity and substrate at a constant temperature between 60-65° C. The method provides high amplification efficiency, with DNA being amplified 109-110 times in 15-60 minutes. Because of its high specificity, the presence of amplified product can indicate the presence of target gene. Since this also uses Bst DNA polymerase, Click chemistry can be used to detect labeling.

Rolling Circle DNA Amplification/Phi29 Based DNA Amplification:

This method uses phi 29 DNA polymerase and can amplify DNA (Linear or circular) with high fidelity and efficiency. Many labs, industrial and academic use it for clinical pathology, academic research and preparation of DNA probes from in situ hybridizations. We propose to do either of the following steps:

(1) add either an azido-dUTP or ethylene-dUTP to replace dTTP in the reaction mix or (2) add either an azido-dUTP or ethylene-dUTP in addition to the four dNTPs Once the polymerase reaction is complete, Click reaction components are added to the amplified DNA. The Click reaction components are $CuSO_4$, BCS, Na-Ascorbate and either an azido-fluorophore or an alkyne-fluorophore. The reaction can then be run directly on an agarose gel As has been described above, Click chemistry can be used between azido/alkyne nucleotides and alkyne/azido dyes to label and detect DNA in other isothermal DNA amplification technologies such as multiple displacement amplification, transcription mediated amplification, etc.

Preparation of Probes for ISH/FISH

The probes for in situ hybridization can also be made using "Click" labeling. Using standard polymerases e.g., Klenow (Exo-), T7 DNA polymerase (Sequenase) or Bst polymerase (Large fragment), one can amplify a template strand for a given sequence using primers as well as using ethynyl or azido dNTPs. The prepared DNA fragments can then be purified and subjected to the click reaction with either azido or alkyne dyes or nanoparticles to create a labeled probe. This is suited to both chromogenically detectable in situ hybridization as well as fluorescent (dyes and Qdots) based probes.

A major advantage that is predicted is that this kind of labeling can be done at the time of diagnostic or clinical assay. In addition the applications include automated in situ hybridization platforms such as instruments from Dako, Ventana Medical Systems, and Vision Biosystems where the hybridization can be followed by the Click reaction to generate the signal.

First Strand cDNA Synthesis (RT-PCR)

As has been demonstrated, ethynyl-dUTP or azido-dATP are incorporated by the telomerase enzyme which is a reverse transcriptase (RNA dependent DNA polymerase). Therefore, this methodology can be used to detect products of RT-PCR. In this method the nucleotide mix can contain either an ethynyl or azido dNTP and enzymes such as reverse transcriptase and DNA polymerase. The product of such an experiment is purified and then subjected to the Click based labeling method. The final labeled product is purified either by precipitation or size exclusion chromatography.

Second Strand cDNA Synthesis (Primer Extension)

The isothermal DNA extension assay shown above was carried out with various different polymerase and serves as an example of second strand cDNA synthesis.

Preparation of RNA Probes for FISH

Currently, the two methods of choice for preparation of the RNA FISH probes are the following:

(1) The small RNA oligonucleotides that can be labeled either via aminoallyl —NHS ester chemistry.

(2) The incorporation of modified nucleotides using in vitro transcription system to generate a RNA probe.

Based on these two technologies and our understanding of the "Clickable" nucleotides, DNA dependent RNA polymerase from phage T7 or SP6 is used to incorporate the ethynyl or azido oligonucleotides to produce a modified RNA probe that is subjected to Click chemistry using either azido or alkyne fluorescent or chromogenic labels. This is used to generate fluorogenic or chromogenic RNA probes.

Method to Prepare Peptide-Nucleic Acid Conjugates Using Click Chemistry:

A peptide with a O-GlcNac modification on one or more amino acids is subjected to a Gal TI reaction in the presence of UDP-GalNAz. This results in an azido modified peptide. As explained above, an oligodeoxynucleotide can be created using either alkyne or azido linked nucleotides. A peptide-nucleic acid conjugate is then created by reacting the Azido-linked peptide and ethynyl decorated oligonucleotides in presence of 1 or 2 mM copper, 10 mM Sodium Ascorbate and 20 mM BCS.

Example 9

Apoptosis Assay

Induce apoptosis in cells using the desired method. It may be desirable to prepare a negative control sample using the cell line of interest by incubating cells in the absence of inducing agent.

Suspend $1-2 \times 10^6$ cells in 0.5 mL of phosphate-buffered saline (PBS). Add the cell suspension into 5 mL of 1% (w/v) paraformaldehyde in PBS and place on ice for 15 minutes. Centrifuge the cells for 5 minutes at 300×g and discard the supernatant. Wash the cells in 5 mL of PBS then pellet the cells by centrifugation. Repeat. Resuspend the cells in 0.5 ml of PBS. Add the cells to 5 mL of ice-cold 70% (v/v) ethanol. Let the cells stand for a minimum of 30 minutes on ice or in a −20° C. freezer. In some biological systems, storage of the cells at −20° C. in 70% (v/v) ethanol for at least 12-18 hours prior to performing the assay yields the best results. Cells can be stored at −20° C. for several days before use.

Resuspend the positive and negative control cells by swirling the vials. Remove 1 mL aliquots of the control cell suspensions (approximately $1 \times 10^6$ cells/mL) and place in 12×75 mm flow cytometry centrifuge tubes. Centrifuge (300×g) the control cell suspensions for 5 minutes and remove the 70% (v/v) ethanol by aspiration, being careful to not disturb the cell pellet. Resuspend the control cells of each tube with 1 mL of Wash Buffer (Component H of Molecular Probes product A23210). Centrifuge for 5 minutes at 300×g and remove the supernatants by aspiration. Repeat. Prepare a DNA-labeling solution; a total volume of 50 µL is required for each sample. Mix 10 µL of reaction buffer (Component G, Molecular Probes Product A23210), 0.75 µL of TdT enzyme (terminal deoxynucleotidyltransferase. Component C, Molecular Probes Product A23210), 8.0 µL of EdUTP (violet cap) and 31.25 µL of dH$_2$O. The DNA-labeling solution is active for approximately 24 hours. Resuspend the control cell pellets of each tube in 50 µL of the DNA-labeling solution. Incubate the cells in the DNA-labeling solution for 60 minutes at 37° C. in a temperature controlled bath. Shake the samples every 15 minutes to keep the cells in suspension. For samples other than the control cells, incubation times at 37° C. may need to be adjusted to longer or shorter periods depending on the characteristics of the experimental samples. The DNA-labeling reaction for the control cells can also be carried out at 22-24° C. overnight. At the end of the incubation time add 1.0 mL of Rinse Buffer (Component I, Molecular Probes product A23210) to each tube and centrifuge at 300×g for 5 minutes. Remove the supernatants by aspiration. Repeat the cell rinsing with 1.0 mL of Rinse Buffer. Centrifuge the samples at 300×g and remove the supernatants by aspiration. Prepare 100 µL of Click Chemistry labeling solution for each sample by mixing 5.0 µL of the Alexa Fluor 488 dye-labeled azide with 95 µL of Rinse Buffer, containing copper sulfate, sodium ascorbate, and BCS in concentrations and proportions as described above. Resuspend the cell pellets in 100 µL of the Click Chemistry labeling solution. Incubate the cells in this solution for 1-3 hours at room temperature. Protect the samples from light during the incubation. Add 0.5 mL of the Propidium Iodide/RNase A Staining Buffer (Component F, Molecular Probes product A23210) to each sample. Incubate the cells for an additional 30 minutes at room temperature. Protect the samples from light during the incubation. Analyze the samples by flow cytometry. It is recommended that the samples be analyzed within 3 hours of completing the staining procedure. For microscopy applications, it is recommended that the cells be deposited onto slides after the Click Chemistry labeling staining step, but prior to the propidium iodide/RNase treatment. Cells that have undergone apoptosis should fluorescence brightly when viewed with filter sets appropriate for fluorescein. For adherent cell lines, detached cells present in the supernatant have a higher probability of being apoptotic than do cells that have remained adherent. Detached cells should be collected prior to trypsinization of the adherent cell layer.

Example 10

Digoxin Azide

Mild acid hydrolysis of digoxin will cleave the sugar moieties and provide the known alcohol derivative. Reaction of this alcohol with phosgene, followed by alkylation with 6-amino-hexanyl-1-azide trifluoroacetic acid salt, will provide the desired azido-digoxin analogue.

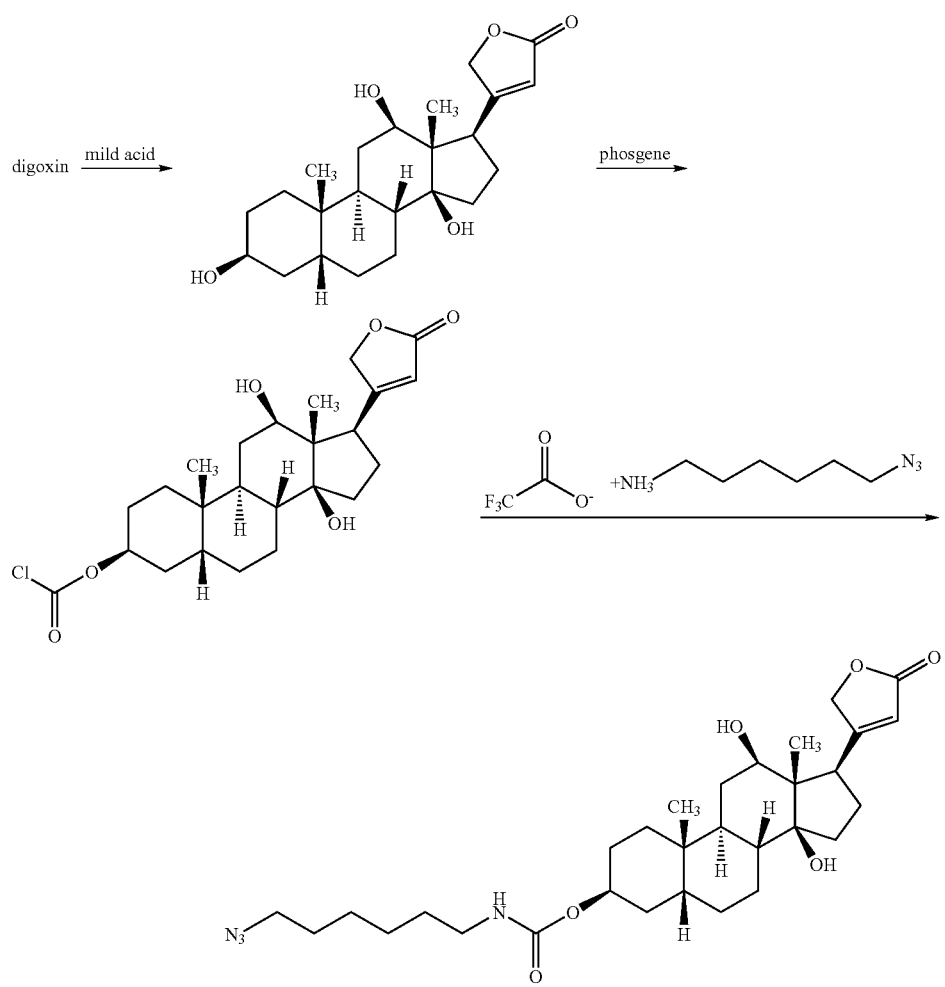
Example 11
Digoxin Alkyne
Mild acid hydrolysis of digoxin will effectively cleave the sugar moieties and provide the known alcohol derivative. Reaction of this alcohol with phosgene, followed by alkylation with propargylamine will provide the desired alkynyl-digoxin analogue.
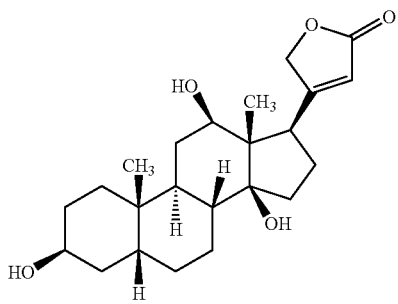
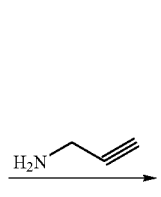

Example 12

Synthesis of Dapoxyl® alkyne

The synthesis of Dapoxyl® alkyne is shown in the following reaction scheme.

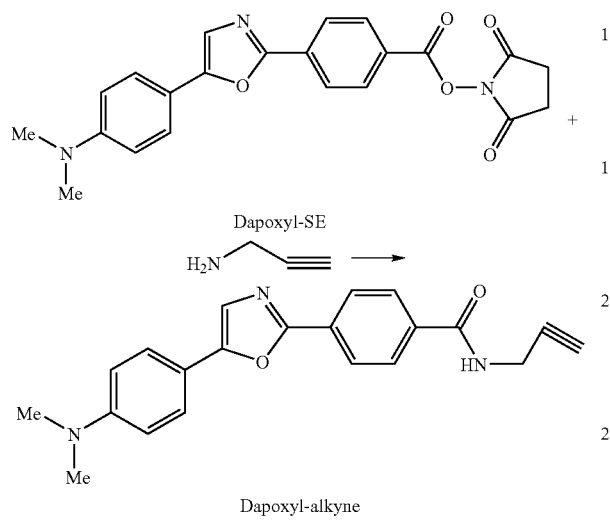

To a solution of Dapoxyl® carboxylic acid, succinimidyl ester (50 mg, 0.12 mmol) in DMF (0.4 mL) at RT was added propargylamine (42 µL, 0.61 mmol). The initial clear orange solution turned yellow and cloudy. After 15 min at RT the reaction was complete, and the solution was concentrated to dryness. The residue was purified via HPLC to afford the product (36 mg, 84%). TLC (10% EtOAc, CHCl$_3$) R$_f$=0.30; ESI m/z 346 (M$^+$, C$_{21}$H$_{19}$N$_3$O$_2$ requires 346).

Example 13

Synthesis of 5-Carboxytetramethyl rhodamine alkyne (5-TAMRA-alkyne)

The synthesis of 5-Carboxytetramethyl rhodamine alkyne (5-TAMRA-alkyne) is shown in the following reaction scheme.

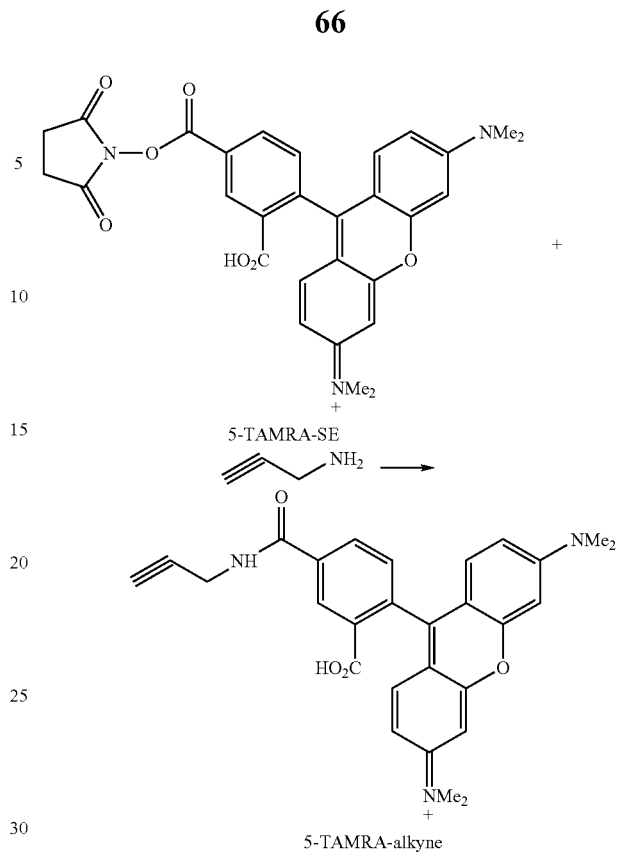

To a solution of 5-carboxytetramethyl rhodamine, succinimidyl ester (5-TAMRA-SE, 0.10 g, 0.19 mmol) in DMF (0.5 mL) was added propargylamine (25 µL, 0.38 mmol) and H$_2$O (0.5 mL). After stirring the solution for 30 min at RT, the solution was concentrated in vacuo. Purification via HPLC (Phenomenex Prodigy ODS, internal diameter 21.2 mm, eluent 25-40% CH$_3$CN in 25 mM TEAA, pH 4.7, flow rate of 15 mL/min) gave 68 mg of product (82%, a purple solid) t$_R$=23-33 min. TLC (CH$_3$CN:H$_2$O, 8:2) R$_f$=0.67.

Example 14

Synthesis of Biotin alkyne

The synthesis of Biotin alkyne is shown in the following reaction scheme.

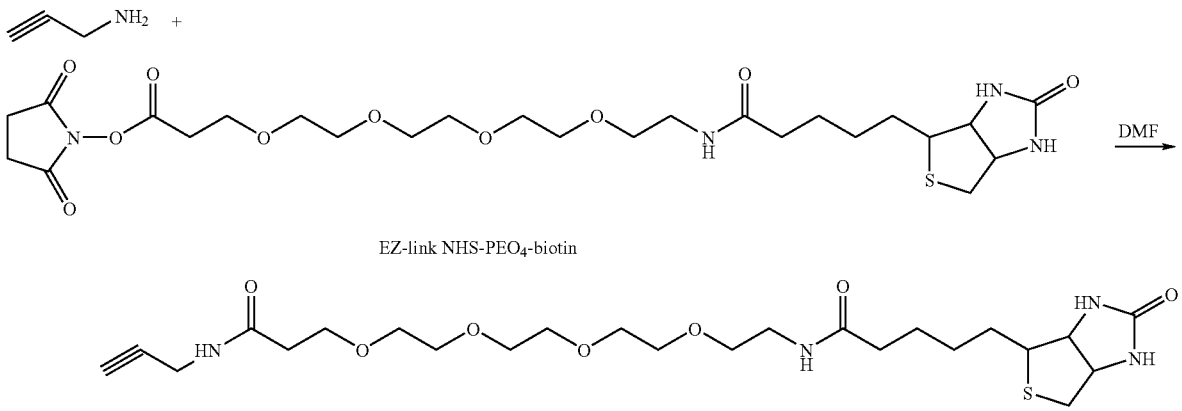

To a solution of EZ-link NHS-PEO$_4$-biotin (25 mg, 0.004 mmol, Pierce) in DMF (0.1 mL) was added propargylamine (0.1 mL). After stirring the solution for 90 min at RT, some starting material was still seen. Additional propargylamine (0.2 mL) was added and the solution was stirred for another 60 min. The solution was concentrated in vacuo. The crude material was purified via HPLC to afford 14.4 mg (64%) of the product as a yellow solid. TLC (CHCl$_3$:MeOH, 7:1) R$_f$=0.23; ESI m/z 529 (M$^+$, C$_{24}$H$_{40}$N$_4$O$_7$S requires 529).

Example 15

Synthesis of Compound 1

The synthesis of Compound 1 is shown in the following reaction scheme.

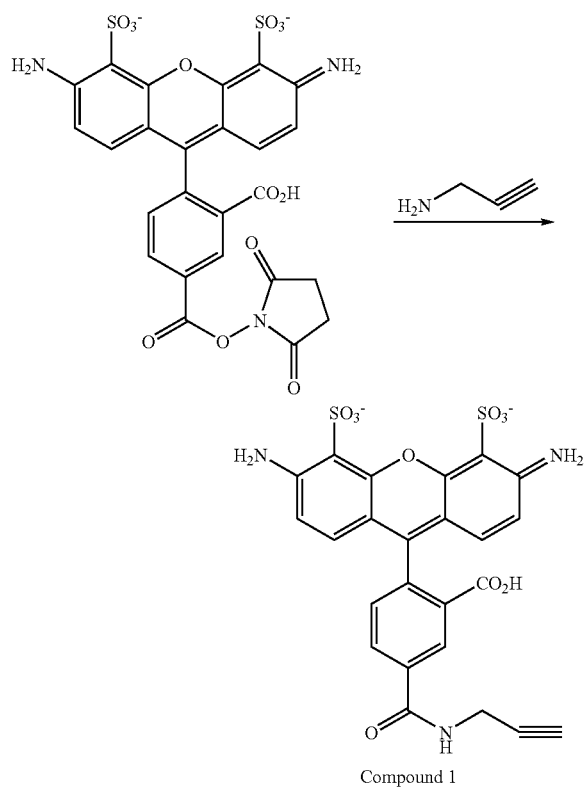

Compound 1

To a solution of Alexa Fluor® 488 carboxylic acid, succinimidyl ester, dilithium salt (mixed isomers, 50 mg, 0.079 mmol) in DMF (2.0 mL) was added propargylamine (54 μL, 0.79 mmol). The solution was stirred overnight at RT. The initial deep red solution turned pale yellow in color and became clear. The solution was concentrated in vacuo and purified via silica gel thin layer chromatography (prep plate, 20% H$_2$O, CH$_3$CN) to afford the product (20 mg, 44%) as an orange solid. TLC (3:1, CH$_3$CN:H$_2$O)R$_f$=0.70; ESI neg m/z 570 (M$^+$, C$_{24}$H$_{16}$N$_3$O$_{10}$S$^{2-}$ requires 570).

Example 16

Synthesis of Compound 2

The synthesis of Compound 2 is shown in the following reaction scheme.

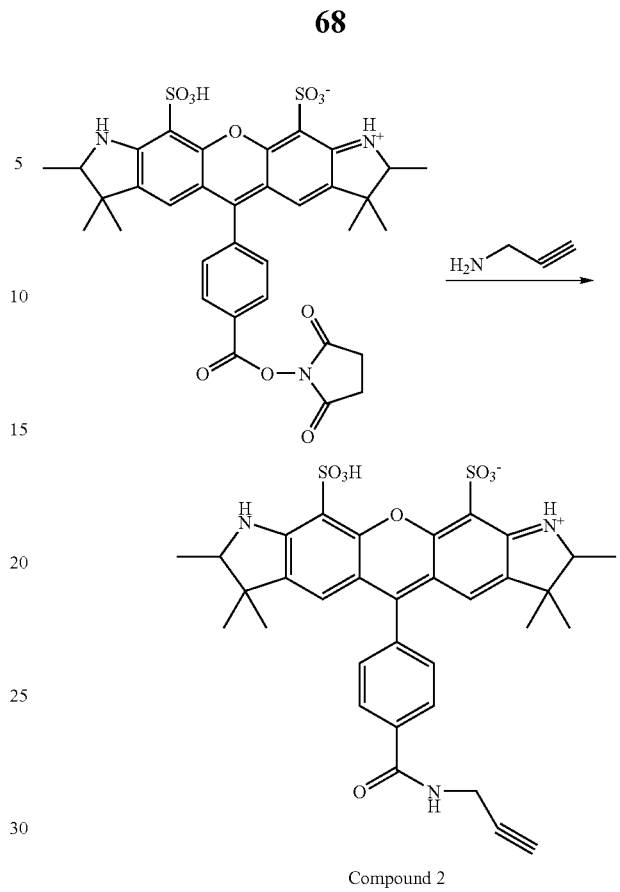

Compound 2

To a solution of Alexa Fluor® 532 carboxylic acid, succinimidyl ester (50 mg, 0.070 mmol) in DMF (2.2 mL) was added propargylamine (100 μL, 1.46 mmol). The solution was stirred overnight at RT. H$_2$O (1.0 mL) was added to the solution and the solution was stirred an additional hour. The solution was concentrated in vacuo and the crude material was purified via HPLC to afford the product (30 mg, 65%). TLC (8:2, CH$_3$CN:H$_2$O) R$_f$=0.58; ESI m/z 664 (M$^+$, C$_{33}$H$_{33}$N$_3$O$_8$S$_2$ requires 664).

Example 17

Synthesis of Compound 3

The synthesis of Compound 3 is shown in the following reaction scheme.

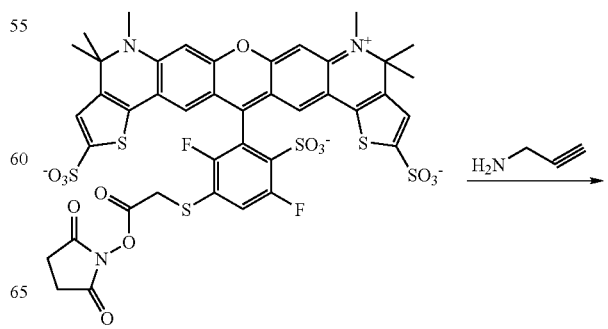

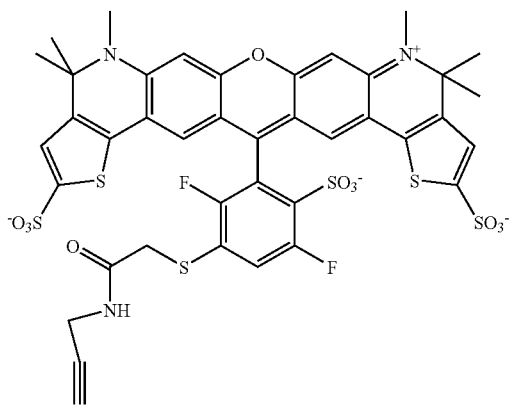

Compound 3

To a solution of Alexa Fluor® 633 carboxylic acid, succinimidyl ester, bis(triethylammonium salt) (50 mg, 0.041 mmol) in DMF (2.0 mL) was added propargylamine (28 μL, 0.40 mmol). The solution was stirred overnight at RT. H$_2$O (1.0 mL) was added to the solution and the solution was stirred an additional hour. The solution was concentrated in vacuo and the product (39 mg, 99%). TLC (8:2, CH$_3$CN: H$_2$O) R$_f$=0.66; ESI m/z 963 (M$^+$, C$_{40}$H$_{34}$F$_2$N$_3$O$_{11}$S$_6$ requires 963).

Example 18

Synthesis of Triarylphosphine-TAMRA Dye for Staudinger Ligation

The synthesis of triarylphosphine-TAMRA dye is shown in the reaction scheme below.

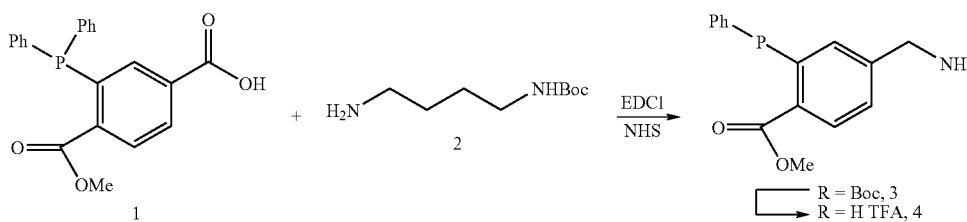

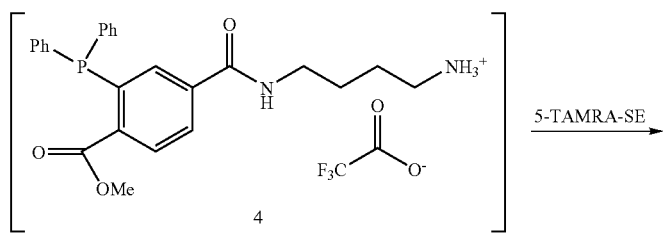

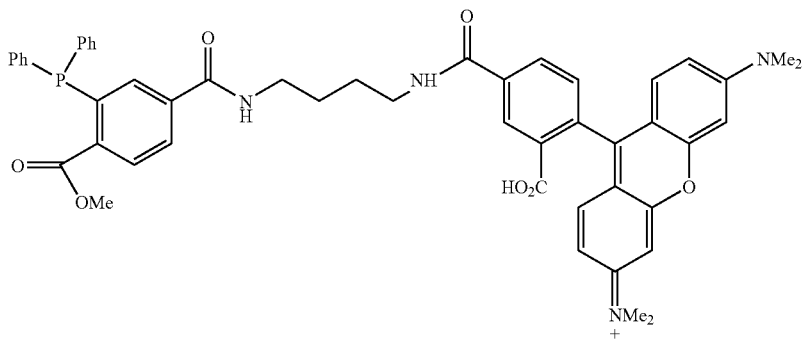

To a solution of acid 1 (ref: *Science* 2000, 287, 2007-2010) (80 mg, 0.26 mmol) in $CH_2Cl_2$ (5 mL) was added N-(3-dimethylaminopropyl)-N'-ethylcarbodiimide hydrochloride (EDCI, 75 mg, 0.39 mmol) and N-hydroxysuccinimide (NHS, 5 mg). The solution was stirred at RT. After 2.5 h, amine 2 (50 μL, 0.26 mmol) was added and the solution was stirred overnight. The solution was partitioned between $CHCl_3$ (15 mL) and $H_2O$ (5 mL). The organic layer was separated and the aqueous layer was reextracted with $CHCl_3$ (15 mL). The combined organic layers were rinsed once with $H_2O$ (5 mL), followed by saturated aqueous NaCl (5 mL).

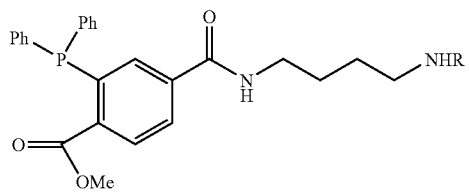

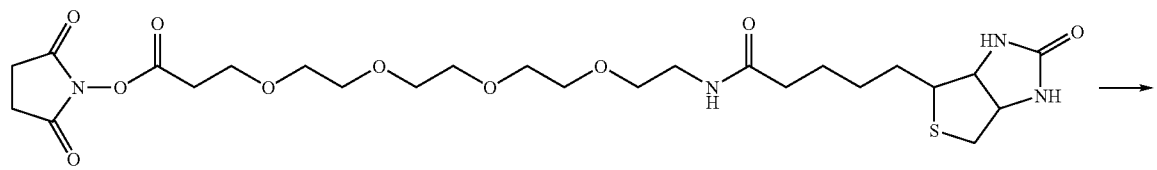

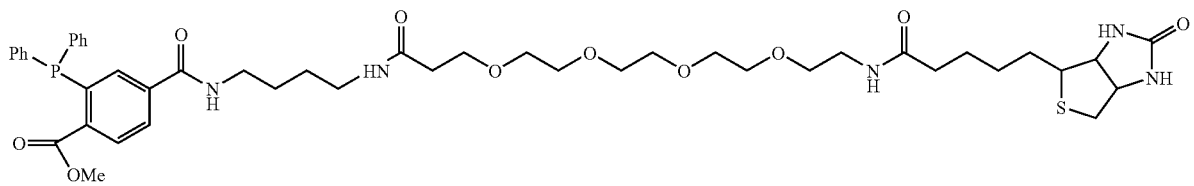

The organic layer was dried over $Na_2SO_4$, decanted and concentrated. The crude was purified via chromatography (silica, 2% MeOH, $CHCl_3$) to afford the product (99 mg, 71%) as a clear, yellow oil.

To a solution of 3 (10 mg, 0.018 mmol) in $CH_2Cl_2$ (1.0 mL) was added trifluoracetic acid (TFA, 0.5 mL) and the solution was stirred at RT. After 30 min, the solution was concentrated and reevaporated from toluene (2×2 mL). The residue (4, 0.018 mmol) was dissolved in DMF (0.2 mL) and N-ethyldiisopropylamine (DIEA, 12 μL, 0.72 mmol), and 5-carboxytetramethyl rhodamine, succinimidyl ester (5-TAMRA-SE, 9 mg, 0.022 mmol) were added. The solution was stirred at RT for 2.5 h, concentrated and purified via silica gel (prep plate, 20% $H_2O$ in $CH_3CN$) to afford the product (7.4 mg, 48%). TLC (20% $H_2O$ in $CH_3CN$) $R_f$=0.23; ESI m/z 529 ($M^+$, $C_{24}H_{40}N_4O_7S$ requires 529).

Example 19

Synthesis of Triarylphosphine-Biotin for Staudinger Ligation

The synthesis of triarylphosphine-biotin is shown in the following reaction scheme.

To a solution of 3 (5.3 mg, 0.010 mmol) in $CH_2Cl_2$ (1.2 mL) was added trifluoracetic acid (TFA, 0.5 mL) and the solution was stirred at RT. After 2 h, the solution was concentrated and reevaporated from toluene (2×2 mL). The residue (4, 0.010 mmol) was dissolved in DMF (0.1 mL) and N-ethyldiisopropylamine (DIEA, 3 μL, 0.02 mmol), and EZ-link NHS-$PEO_4$-biotin (7 mg, 0.012 mmol) were added. The solution was stirred at RT for 1 h, quenched with saturated $NH_4^+$ $Cl^-$ and partitioned between $CHCl_3$ (10 mL) and $H_2O$ (1 mL). The aqueous layer was extracted repeatedly with $CHCl_3$ (10 mL per extraction) until no ultraviolet spot was observed by TLC. The combined organic layers were concentrated and purified via silica gel (prep plate, 7:1 $CHCl_3$:MeOH) to afford the product (2.2 mg, 25%). TLC (7:1 $CHCl_3$:MeOH, developed 3 times) $R_f$=0.50; ESI m/z 909 ($M+H^+$, $C_{46}H_{63}N_5O_{10}PS$ requires 909).

Example 20

Synthesis of Cy™5.5Azide

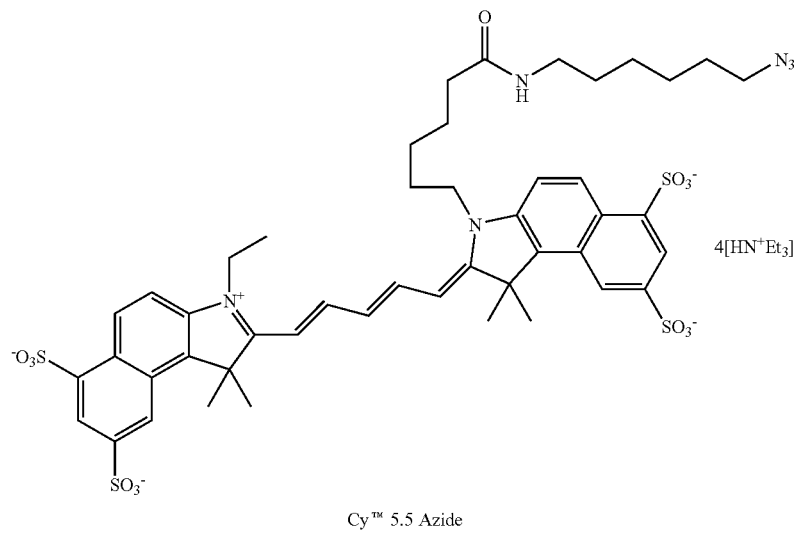

Cy™ 5.5 Azide

To a solution of 6-(amino)-hexanyl-1-azide trifluoroacetic acid salt (see Scheme 1 for synthesis, 0.034 mmol) in DMF (0.1 mL) and DIEA (6.0 μL, 0.034 mmol) was added Cy™5.5 succinimidyl ester (5 mg, 3.4 nmol). After stirring the solution at RT for 10 min, the reaction solution was concentrated in vacuo. The crude was purified via HPLC.

Example 21

Synthesis of Cy™3Azide

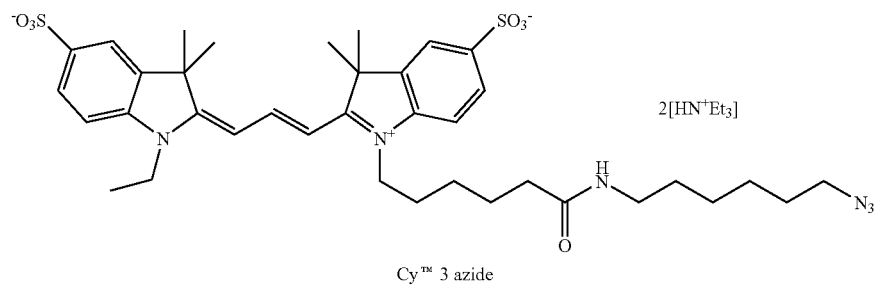

Cy™ 3 azide

To a solution of 6-(amino)-hexanyl-1-azide trifluoroacetic acid salt (see Scheme 1 for synthesis, 0.052 mmol) in DMF (0.1 mL) and DIEA (9.2 μL, 0.052 mmol) was added Cy™3 succinimidyl ester (5.0 mg, 5.2 nmol). After stirring the solution at RT for 10 min, the reaction solution was concentrated in vacuo. The crude was purified via HPLC.

Example 22

Synthesis of Cy™5.5Alkyne

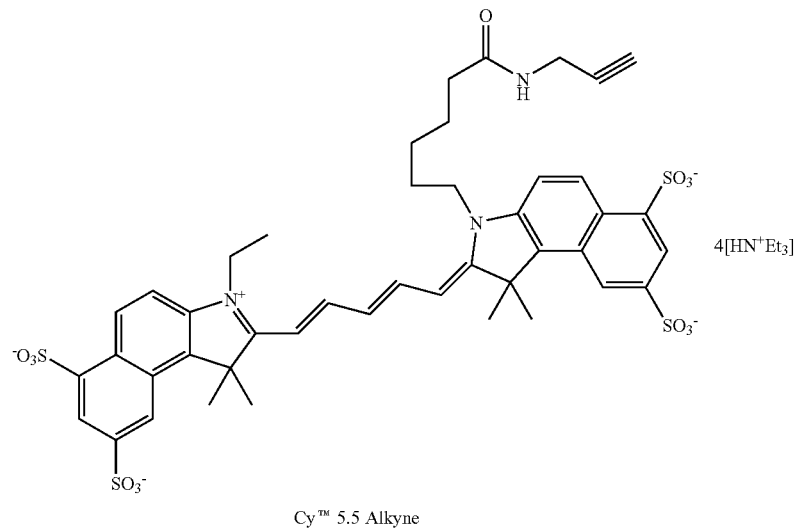

Cy™ 5.5 Alkyne

To a solution of Cy™5.5 succinimidyl ester (GE Amersham, 5.0 mg, 3.7 nmol) in DMF (0.1 mL) was added propargylamine (2.5 µL, 0.037 mmol) and H₂O (0.2 mL). The solution was stirred at RT for 30 min then concentrated in vacuo. The crude was purified via HPLC.

Example 23

Synthesis of Cy™3Alkyne

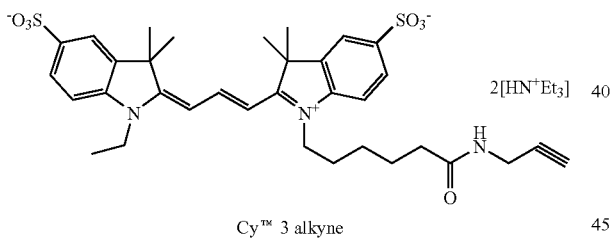

Cy™ 3 alkyne

To a solution of Cy™3 succinimidyl ester (GE Amersham, 5.0 mg, 5.7 nmol) in DMF (0.1 mL) was added propargylamine (3.9 µL, 0.057 mmol) and H₂O (0.2 mL). The solution was stirred at RT for 30 min then concentrated in vacuo. The crude was purified via HPLC.

Example 24

Succinimidyl ester azide synthesis

The synthesis of succinimidyl ester azide is shown in the following reaction scheme.

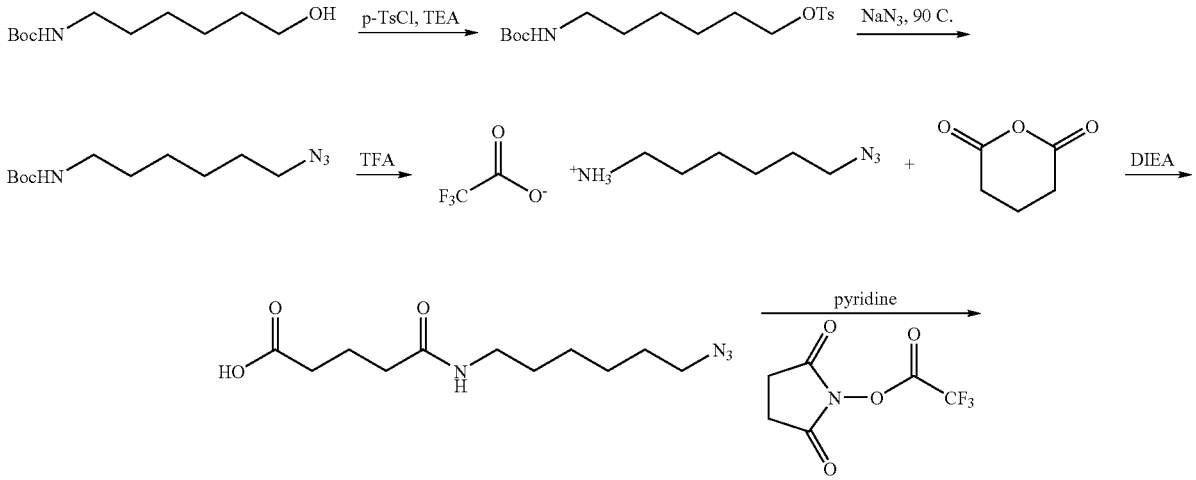

-continued

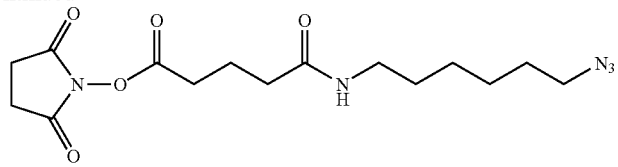

(N-6-Azido-hexanyl)glutaramide

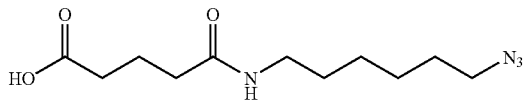

6-(Boc-Amino)-hexanyl-1-p-toluenesulfonate

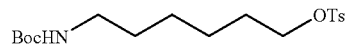

To a solution of 6-(Boc-amino)-1-hexanol (3.0 g, 13.8 mmol) in CHCl₃ (50 mL) was added TEA (3.8 mL, 27.6 mmol) and p-toluenesulfonyl chloride (3.9 g, 20.7 mmol). The solution was stirred at RT overnight, diluted with CHCl₃ (200 mL), washed with H₂O (4×50 mL), rinsed with brine (1×50 mL) and dried over Na₂SO₄. The solution was decanted, concentrated and purified via silica gel chromatography (6.0×41 cm, 20-70% EtOAc/hexanes) to afford the product as a white solid (3.5 g, 69%). TLC (35% EtOAC/hexanes) $R_f$=0.72, UV active.

6-(Boc-Amino)-hexanyl-1-azide

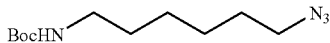

To a solution of 6-(Boc-amino)-hexanyl-1-p-toluenesulfonate (3.2 g, 8.63 mmol) in DMF (21 mL) was added sodium azide (1.12 g, 17.3 mmol). The solution was refluxed at 95° C. overnight. After cooling to RT, the solution was diluted with Et₂O (160 mL) and washed with H₂O (100 mL). The aqueous layer was extracted a second time with Et₂O (100 mL) and the combined organics were dried over Na₂SO₄. After decanting and concentrating, the crude material was purified via silica gel chromatography (6×26 cm, 25-30% EtOAc/hexanes) to afford the product as a clear, colorless oil (2.0 g, 97%). TLC, (35% EtOAC/hexanes) $R_f$=0.74, brown spot with ninhydrin stain.

6-(Amino)-hexanyl-1-azide trifluoroacetic acid salt

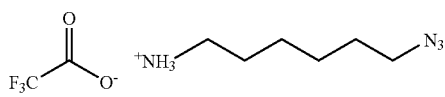

To a solution of 6-(Boc-amino)-hexanyl-1-azide (0.2 g, 0.83 mmol) in CH₂Cl₂ (1.0 mL) was added TFA (1.0 mL). The solution was stirred at RT for 2 h, evaporated to dryness and re-evaporated twice from toluene. The product, 6-amino-hexanyl-1-azide trifluoroacetic acid salt (0.83 mmol) was used directly without further purification 6-Amino-hexanyl-1-azide (0.83 mmol) was dissolved in THF (1.0 mL) and N,N-diisopropylethylamine (0.29 mL, 1.65 mmol) was added. The solution was stirred at RT for 10 min then glutaric anhydride (0.47 g, 4.13 mmol) was added. The pale yellow solution was stirred at RT overnight. The reaction solution was diluted with CHCl₃ (30 mL) and H₂O (10 mL), and acidified to a pH of 1 with 1% HCl; the organic layer was removed. The aqueous layer was extracted two more times with CHCl₃ (2×30 mL). The combined organic layers were rinsed with brine (2×10 mL) and dried over Na₂SO₄. The solution was decanted, and concentrated. The crude was purified via silica gel chromatography (10% MeOH/CHCl₃ containing 0.1% AcOH) to afford the product as a clear, colorless oil (0.16 g, 75%). The column was loaded with 10% MeOH/CHCl₃. TLC (10% MeOH/CHCl₃ with 0.1% AcOH) $R_f$=0.41, pink with p-anisaldehyde stain, no UV activity.

(N-6-Azido-hexanyl)glutaramide, succinimidyl ester

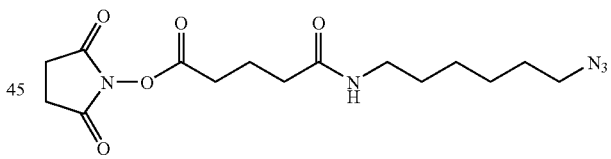

To a solution of the (N-6-azido-hexanyl)glutaramide (75 mg, 0.29 mmol) in THF (4.0 mL) was added pyridine (110 μL, 1.36 mmol) followed by succinimidyl trifluoroacetate (200 mg, 0.95 mmol). The clear, colorless solution was stirred at RT for 4 h. The reaction solution was diluted with CHCl₃ (20 mL) and rinsed sequentially with 1% AcOH (2×5 mL), H₂O (2×5 mL) and brine (1×5 mL). The crude solution was dried over Na₂SO₄, decanted, and concentrated to afford the product as a clear, colorless oil (0.10 g, 99%). TLC: (1:1, EtOAc/hexanes) $R_f$=0.64, orange with ninhydrin, UV active.

Example 25

Succinimidyl ester alkyne synthesis

The synthesis of succinimidyl ester alkyne is shown in the following reaction scheme.

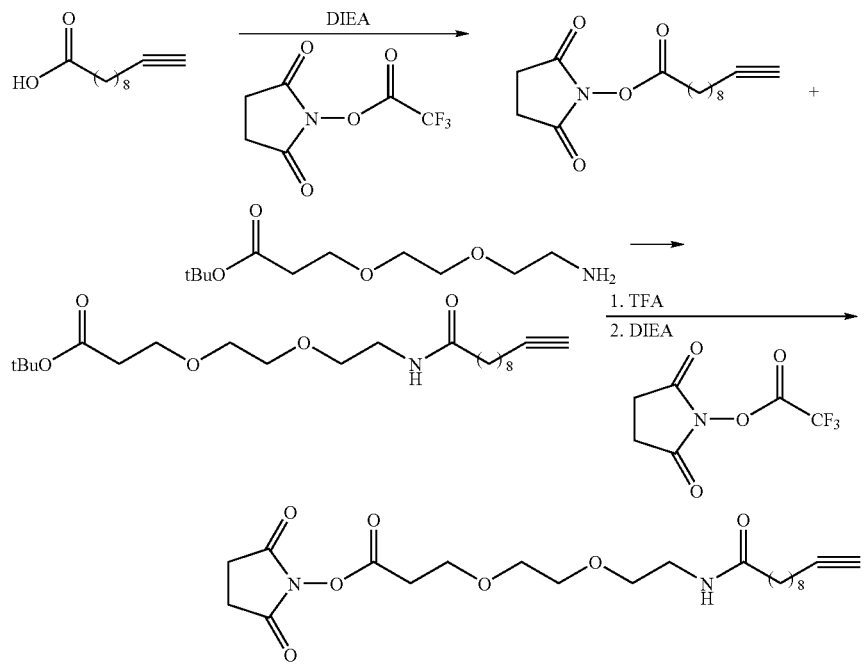

10-Undecynoic acid succinimidyl ester

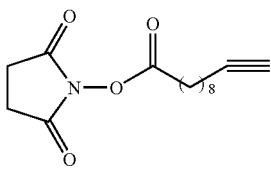

To a solution of 10-undecynoic acid (0.40 g, 2.2 mmol) in CH$_3$CN (10 mL) was added O—(N-succinimidyl)-N,N,N', N'-tetramethyluronium tetrafluoroborate (0.99 g, 3.29 mmol). After stirring for 2 min at RT, the reaction was quenched with 1% AcOH and diluted with CHCl$_3$ (150 mL). The organic solution was then extracted with 1% AcOH (10 mL), rinsed with H$_2$O (2×40 mL), then dried over Na$_2$SO$_4$. The solution was then decanted and concentrated. A quantitative yield was assumed and the material was taken on directly to the next step. TLC (10% MeOH/CHCl$_3$) R$_f$=0.90, UV active.

tert-Butyl alkyne

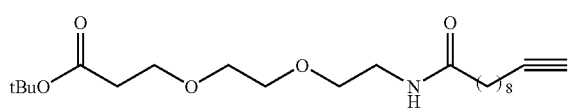

To a solution of 10-undecynoic acid succinimidyl ester (0.61 g, 2.19 mmol) in CH$_3$CN (8 mL) was added amino-dPEG™$_2$-tert-butyl ester (0.46 g, 1.97 mmol, Quanta BioDesign) in CH$_3$CN (2 mL) at RT. After 2 hrs, the solution was diluted with CHCl$_3$ (50 mL) and extracted with H$_2$O (5 mL). The aqueous layer was reextracted with CHCl$_3$ (2×50 mL). Combined organics were dried over Na$_2$SO$_4$, decanted and concentrated. The crude was purified via silica gel chromatography (2.5% MeOH/CHCl$_3$) to afford the product as a clear, pale yellow oil (0.48 g, 55%). TLC (9:1 CH$_3$CN:H$_2$O) R$_f$=0.81.

Succinimidyl ester alkyne

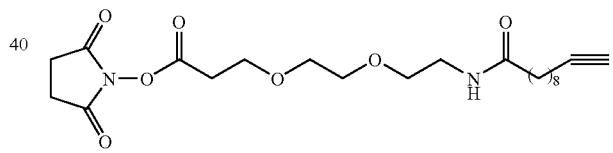

To a solution of tert-butyl alkyne (0.48 g, 1.2 mmol) in CH$_2$Cl$_2$ (2.0 mL) was added TFA (2.0 mL). The solution was stirred for 1 h, then concentrated and reevaporated from toluene (2×1 mL). The resulting brown residue was dissolved in CH$_3$CN (5.0 mL) and N,N-diisopropylethylamine (0.84 mL, 4.83 mmol) was added. The solution was stirred at RT for 2 min, and then O—(N-succinimidyl)-N,N,N',N'-tetramethyluronium tetrafluoroborate (0.47 g, 1.56 mmol) was added. After 15 min the reaction was quenched and acidified with 1% AcOH to a pH of 4-5. The solution was extracted with CHCl$_3$ (3×50 mL). The combined organics were reextracted with H$_2$O (1×10 mL), then dried over Na$_2$SO$_4$, decanted and concentrated to afford a tan solid (0.46 g, 87%). The crude material was pure enough for testing without further purification. TLC (8:2 CH$_3$CN/H$_2$O) R$_f$=0.79.

Example 26

Iodoacetamide azide synthesis

The synthesis of Iodoacetamide azide is shown in the following reaction scheme.

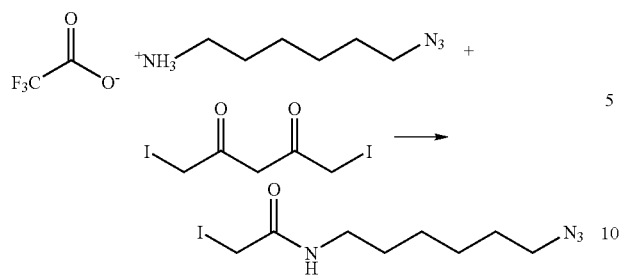
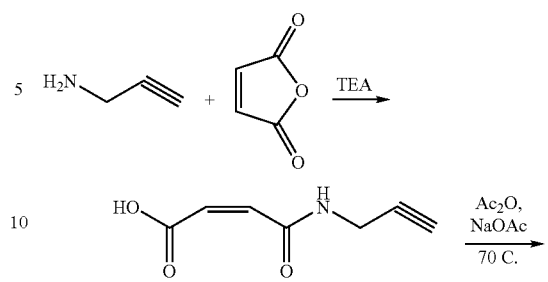

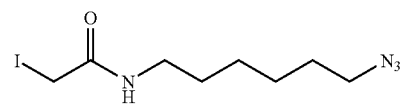

6-(iodoacetamide)-aminohexanyl-1-azide

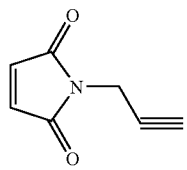

To a solution of 6-amino-hexanyl-1-azide trifluoroacetic acid salt (35 mg, 0.14 mmol) in DMF (0.1 mL) was added iodoacetic anhydride (0.10 g, 0.28 mmol) in the dark. After 2 hr, the reaction was stopped and the solution was partitioned between CHCl$_3$ (10 mL) and H$_2$O (10 mL). The organic layer was removed and the aqueous layer was reextracted with CHCl$_3$ (1×10 mL). The combined organics were rinsed with saturated NaCl (1×5 mL), dried over Na$_2$SO$_4$, decanted and concentrated. Purification via silica gel chromatography (2% MeOH/CHCl$_3$ containing 0.1% AcOH) provided the product (35 mg, 81%) as a yellow oil. TLC (10% MeOH/CHCl$_3$) R$_f$=0.75.

Example 27

Iodoacetamide alkyne synthesis

The synthesis of Iodoacetamide alkyne is shown in the following reaction scheme.

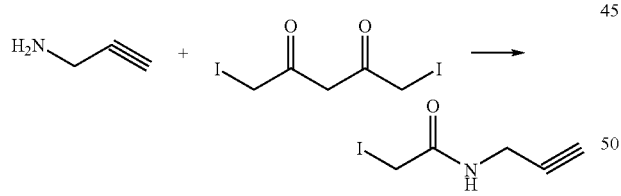

N-(iodoacetamide)-propargylamine. To a solution of propargylamine in DMF was added iodoacetic anhydride in the dark. After 2 hr, the reaction was stopped and the solution was partitioned between CHCl$_3$ and H$_2$O. The organic layer was removed and the aqueous layer was reextracted with CHCl$_3$. The combined organics were rinsed with saturated NaCl, dried over Na$_2$SO$_4$, decanted and concentrated.

Example 28

Maleimide alkyne synthesis

The synthesis of Maleimide alkyne is shown in the following reaction scheme.

Propargylamine maleimide. After the reaction of propargylamine and maleic anhydride in the presence of TEA, the intermediate acid was cyclized in the presence of acetic anhydride and sodium acetate at 70° C., to afford the desired propargylamine maleimide.

Example 29

Maleimide azide synthesis

The synthesis of Maleimide azide is shown in the following reaction scheme.

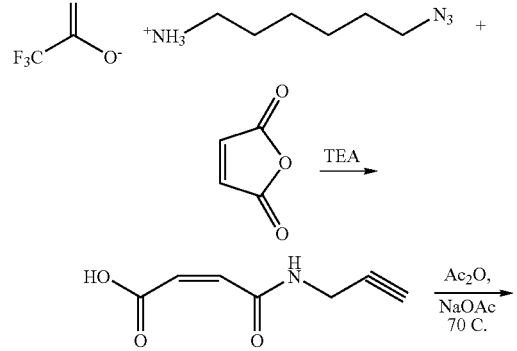

N-(6-Azido-aminohexyl)maleimide. After the reaction of 6-amino-hexanyl-1-azide trifluoroacetic acid salt and maleic anhydride in the presence of TEA, the intermediate acid was cyclized in the presence of acetic anhydride and sodium acetate at 70° C., to afford the desired N-(6-azido-aminohexyl)maleimide.

Example 30

Azido Dyes

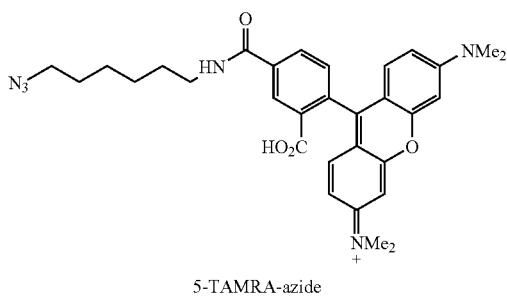

5-TAMRA-azide

5-TAMRA azide. To a solution of 6-(amino)-hexanyl-1-azide trifluoroacetic acid salt (see Scheme 1 for synthesis, 0.19 mmol) in DMF (0.5 mL) and DIEA (33 µL, 0.19 mmol) was added 5-carboxytetramethylrhodamine, succinimidyl ester (5-TAMRA-SE, 50 mg, 0.094 mmol). After stirring the solution at RT for 10 min, the reaction solution was concentrated in vacuo. The crude was purified via silica gel chromatography (prep plate, 9:1 $CH_3CN:H_2O$) to afford the product as a pink solid (45.6 mg, 87%). TLC ($CH_3CN:H_2O$, 8:2) $R_f$=0.61, pink fluorescent spot; ESI-pos m/z 555 $M^+$, $C_{31}H_{35}N_6O_4$ (requires 555).

It is envisioned that any reporter molecule comprising a succinimidyl ester can be azido modified using the methods described herein. Provided below are additional non-limiting examples.

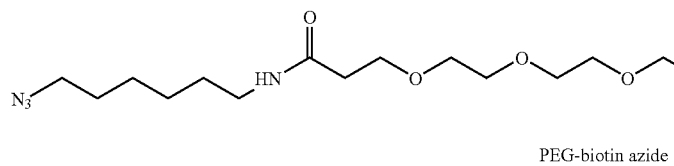

PEG-biotin azide

PEG-biotin azide. To a solution of 6-(amino)-hexanyl-1-azide trifluoroacetic acid salt (see Scheme 1 for synthesis, 0.17 mmol) in DMF (0.5 mL) and DIEA (60 µL, 0.34 mmol) was added NHS-$PEO_4$-biotin (Pierce, 50 mg, 0.08 mmol). After stirring the solution at RT overnight, the solution was concentrated in vacuo. The crude was purified via silica gel chromatography (7:1 $CHCl_3$:MeOH) to afford the product as a cloudy, white residue (12.3 mg, 12%). TLC (7:1, $CHCl_3$:MeOH, 8:2) $R_f$=0.54, faint UV active spot, stains pink with biotin dip; ESI-pos m/z 616 $M^+$, $C_{27}H_{49}N_7O_7S$ (requires 616).

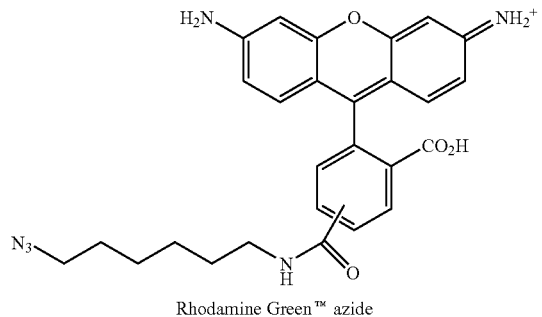

Rhodamine Green™ azide

Rhodamine Green™ azide (mix of 5- and 6-isomers). To a solution of 6-(amino)-hexanyl-1-azide trifluoroacetic acid salt (see Scheme 1 for synthesis, 0.20 mmol) in DMF (0.5 mL) and DIEA (50 µL, 0.28 mmol) was added Rhodamine Green™ carboxylic acid, succinimidyl ester, hydrochloride (mix of 5- and 6-isomers, 50 mg, 0.10 mmol). After stirring the solution at RT for 2 h the solution was concentrated in vacuo. HPLC (Phenomenex Prodigy ODS, internal diameter 21.2 mm, eluent 5-50% $CH_3CN$ (over 60 min) in 25 mM TEAA, pH=4.7, flow rate of 20 mL/min) gave 21.1 mg of product (43%) $t_R$=43-47 min; TLC ($CH_3CN:H_2O$:AcOH, 8:1:1) $R_f$=0.74, fluorescent yellow spot; ESI-pos m/z 499 (M+H, $C_{27}H_{27}N_6O_4$ requires 499).

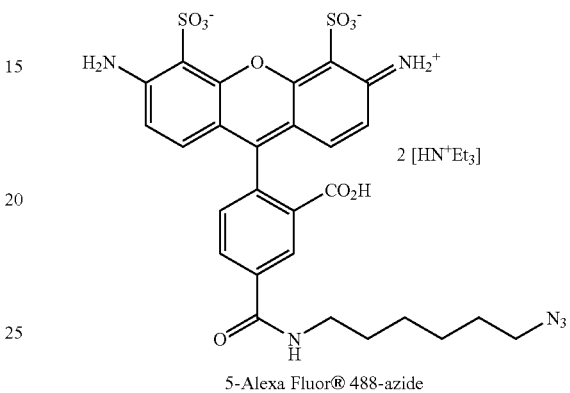

5-Alexa Fluor® 488-azide

Alexa Fluor® 488 azide (5 isomer). To a solution of 6-(amino)-hexanyl-1-azide trifluoroacetic acid salt (see Scheme 1 for synthesis, 0.44 mmol) in DMF (0.5 mL) and DIEA (011 mL, 0.88 mmol) was added Alexa Fluor® 4885-carboxylic acid, 2,3,5,6-tetrafluorophenyl ester, bis(triethylammonium salt) (200 mg, 0.22 mmol). After stirring the solution at RT for 1 h, the solution was concentrated in vacuo. HPLC (Phenomenex Prodigy ODS, internal diameter 21.2 mm, eluent 0-60% $CH_3CN$ (over 30 min) in 25 mM TEAA, pH=4.7, flow rate of 20 mL/min) gave 58.1 mg of product (30%) $t_R$=23-27 min; TLC ($CH_3CN:H_2O$, 8:2) $R_f$=0.58, fluorescent yellow spot; ESI-neg m/z 657 ($M^-$, $C_{27}H_{25}N_6O_{10}S_2^-$ requires 657).

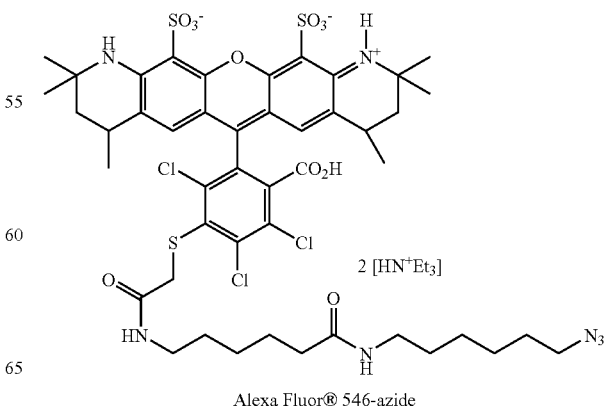

Alexa Fluor® 546-azide

Alexa Fluor® 546 azide. To a solution of 6-(amino)-hexanyl-1-azide trifluoroacetic acid salt (see Scheme 1 for synthesis, 0.093 mmol) in DMF (0.5 mL) and DIEA (32 µL, 0.19 mmol) was added Alexa Fluor® 546 carboxylic acid, succinimidyl ester, (50 mg, 0.05 mmol). After stirring the solution at RT for 2 h, the solution was concentrated in vacuo.

HPLC (Phenomenex Prodigy ODS, internal diameter 21.2 mm, eluent 10-60% $CH_3CN$ (over 60 min) in 25 mM TEAA, pH=4.7, flow rate of 20 mL/min) gave 27.2 mg of product (54%) $t_R$=48-52 min; TLC ($CH_3CN:H_2O$, 9:1) $R_f$=0.24, fluorescent pink spot; ESI-neg m/z 1084 (M⁻, $C_{46}H_{55}Cl_3N_7O_{11}S_3$ requires 1084).

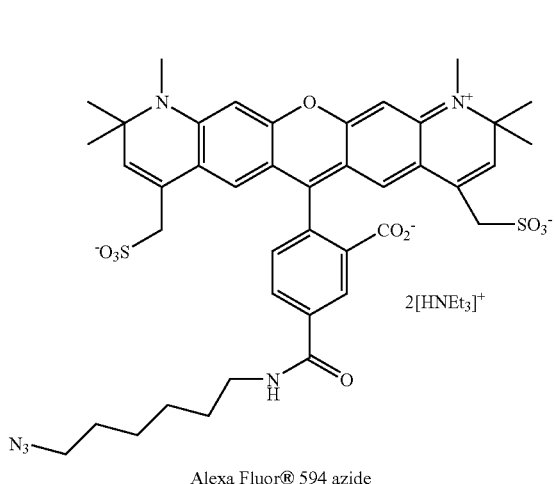

Alexa Fluor® 594 azide

Alexa Fluor® 594 azide (5 isomer). To a solution of 6-(amino)-hexanyl-1-azide trifluoroacetic acid salt (see Scheme 1 for synthesis, 0.12 mmol) in DMF (0.5 mL) and DIEA (42 µL, 0.24 mmol) was added Alexa Fluor® 594 carboxylic acid, succinimidyl ester *5-isomer* (50 mg, 0.06 mmol). After stirring the solution at RT for 2 h, the solution was concentrated in vacuo. HPLC (Phenomenex Prodigy ODS, internal diameter 21.2 mm, eluent 25-60% $CH_3CN$ (over 30 min) in 25 mM TEAA, pH=4.7, flow rate of 20 mL/min) gave 16.5 mg of product (32%) $t_R$=23-25 min; TLC ($CH_3CN:H_2O$, 9:1) $R_f$=0.36, fluorescent red spot; ESI-neg m/z 845 (M⁻, $C_{41}H_{45}N_6O_{10}S_2^-$ requires 845).

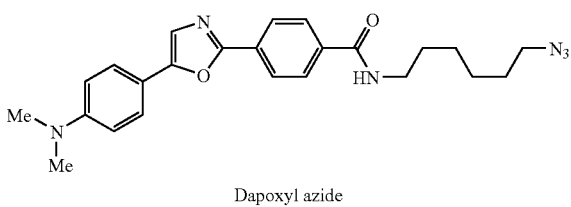

Dapoxyl azide

Dapoxyl azide. To a solution of 6-(amino)-hexanyl-1-azide trifluoroacetic acid salt (see Scheme 1 for synthesis, 0.25 mmol) in DMF (0.5 mL) and DIEA (43 µL, 0.25 mmol) was added Dapoxyl® carboxylic acid, succinimidyl ester (50 mg, 0.12 mmol). After stirring the solution at RT for 1 h, the solution was concentrated in vacuo. Purified by SPE (Supelco C18 DSC) to give 41.6 mg of product (78%); ESI-pos m/z 433 (M⁺, $C_{24}H_{28}N_6O_2$ requires 433).

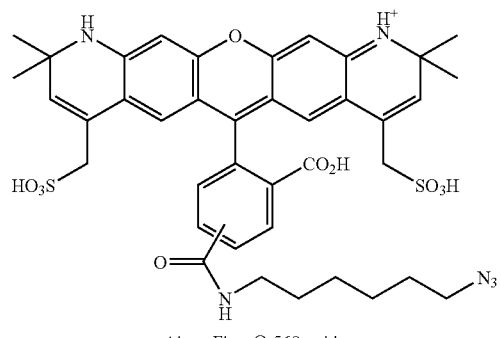

Alexa Fluor® 568-azide

Alexa Fluor® 568-azide. To a solution of 6-(amino)-hexanyl-1-azide (see Scheme 1 for synthesis, 0.04 mmol) in DMF (0.2 mL) and DIEA (7 µL, 0.04 mmol) was added Alexa Fluor® 568 carboxylic acid, succinimidyl ester (mix of isomers, 25 mg, 0.02 mmol). After stirring the solution at RT for 2.5 h, $H_2O$ (0.2 mL) was added and the solution was concentrated in vacuo. HPLC (Phenomenex Prodigy ODS, internal diameter 21.2 mm, eluent 20-35% $CH_3CN$ in 25 mM $NH_4Ac$, pH 4.7, flow rate of 15 mL/min) gave 15.3 mg of product (99%) $t_R$=24-30 min; TLC ($CH_3CN:H_2O$, 8:2) $R_f$=0.63, fluorescent pink spot; ESI-neg m/z 817 (M–2, $C_{39}H_{41}N_6O_{10}S_2^-$ requires 817).

Example 31

Alkyne Dyes

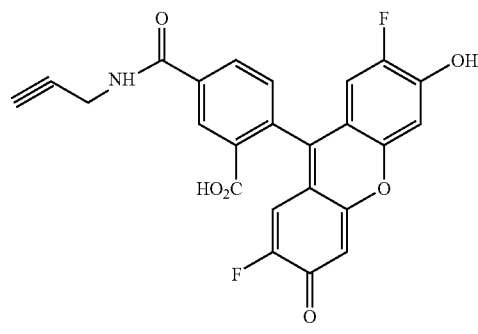

Oregon Green® 488–alkyne

Oregon Green® 488-alkyne. To a solution of Oregon Green® 488 carboxylic acid, succinimidyl ester (50 mg, 0.98 mmol) in DMF (0.5 mL) was added propargylamine (0.26 µL, 0.40 mmol) and $H_2O$ (0.1 mL). After stirring at RT for 15 min, the solution was concentrated. HPLC (Phenomenex Prodigy ODS, internal diameter 21.2 mm, eluent 15-30% CH3Cn in 25 mM TEAA pH 4.7, flow rate of 15 mL/min) gave 44.5 mg of product (99%) $t_R$=5-13 min; TLC ($CH_3CN:H_2O$, 8:2) $R_f$=0.60, fluorescent yellow spot; ESI-neg m/z 448 (M–H⁺, $C_{24}H_{12}F_2NO_6^-$ requires 448).

It is envisioned that any reporter molecule comprising a succinimidyl ester can be alkyne modified using the methods described herein. Provided below are additional non-limiting examples.

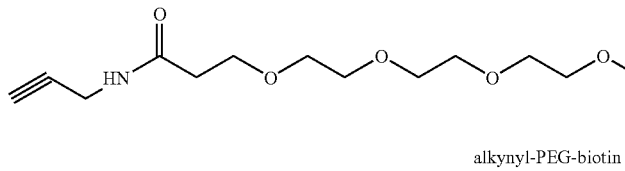

alkynyl-PEG-biotin

Alkynyl-PEG-biotin. To a solution of NHS-PEO$_4$-biotin (Pierce, 25 mg, 0.004 mmol) in DMF (0.1 mL) at RT was added propargylamine (0.3 mL, 4.5 mmol). After stirring for 3 h, the solution was concentrated in vacuo and re-evaporated twice from toluene. HPLC (Phenomenex Prodigy ODS, internal diameter 21.2 mm, eluent 35-50% MeOH in 25 mM NH$_4$Ac, pH 6.5, flow rate of 15 mL/min) gave 14.4 mg, (64%, a white solid) $t_R$=26-30 min; TLC (CHCl$_3$:MeOH, 7:1) $R_f$=0.20, UV active spot; ESI m/z 529 (M+H$^+$, C$_{24}$H$_{40}$N$_4$O$_7$S requires 529).

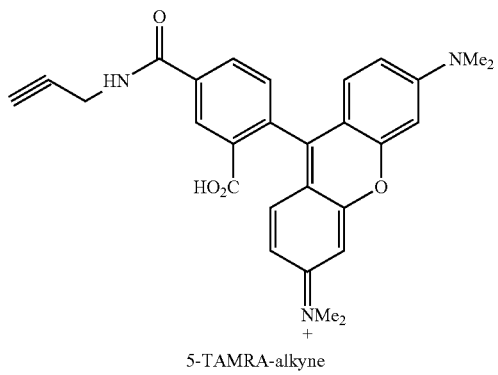

5-TAMRA-alkyne

5-TAMRA-alkyne. To a solution of 5-carboxytetramethyl rhodamine, succinimidyl ester (5-TAMRA-SE, 0.10 g, 0.19 mmol) in DMF (0.5 mL) was added propargylamine (25 µL, 0.38 mmol) and H$_2$O (0.5 mL). After stirring the solution for 30 min at RT, the solution was concentrated in vacuo. HPLC (Phenomenex Prodigy ODS, internal diameter 21.2 mm, eluent 25-40% CH$_3$CN in 25 mM TEAA, pH 4.7, flow rate of 15 mL/min) gave 68 mg of product (82%, a purple solid) $t_R$=23-33 min; TLC (CH$_3$CN:H$_2$O, 8:2) $R_f$=0.67, fluorescent orange spot; ESI m/z 469 (M+H$^+$, C$_{28}$H$_{26}$N$_3$O$_4$ requires 469).

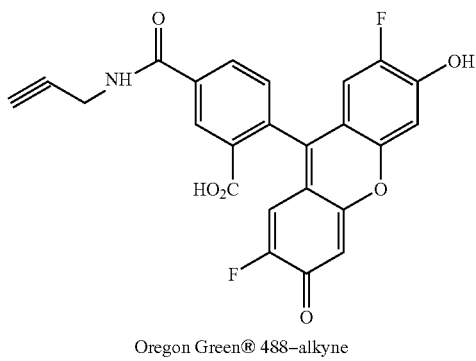

Oregon Green® 488–alkyne

Oregon Green® 488-alkyne. To a solution of Oregon Green® 488 carboxylic acid, succinimidyl ester (50 mg, 0.98 mmol) in DMF (0.5 mL) was added propargylamine (0.26 µL, 0.40 mmol) and H$_2$O (0.1 mL). After stirring at RT for 15 min, the solution was concentrated. HPLC (Phenomenex Prodigy ODS, internal diameter 21.2 mm, eluent 15-30% CH$_3$Cn in 25 mM TEAA pH 4.7, flow rate of 15 mL/min) gave 44.5 mg of product (99%) $t_R$=5-13 min; TLC (CH$_3$CN:H$_2$O, 8:2) $R_f$=0.60, fluorescent yellow spot; ESI-neg m/z 448 (M−H$^+$, C$_{24}$H$_{12}$F$_2$NO$_6^-$ requires 448).

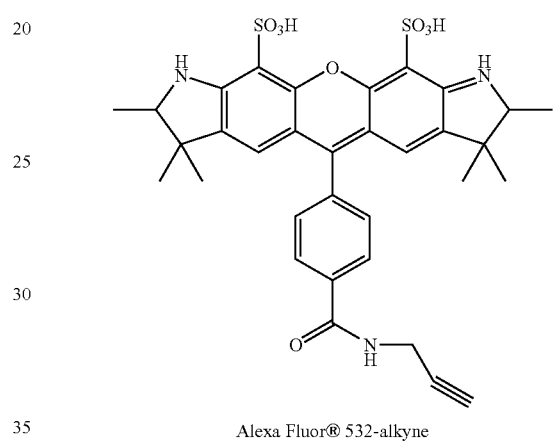

Alexa Fluor® 532-alkyne

Alexa Fluor® 532-alkyne. To a solution of Alexa Fluor® 532 carboxylic acid, succinimidyl ester (51 mg, 0.07 mmol) in DMF (4.0 mL) was added propargylamine (0.1 mL) and H$_2$O (1.0 mL). The solution was stirred at RT for 1 h then concentrated in vacuo to afford the crude product. HPLC (Phenomenex Prodigy ODS, internal diameter 21.2 mm, eluent 25-40% CH$_3$CN in 25 mM NH$_4$Ac, pH 4.7, flow rate of 15 mL/min) gave 30 mg of product (65%, a red solid) $t_R$=23-30 min; TLC (CH$_3$CN:H$_2$O, 1:1) $R_f$=0.58, fluorescent red spot; ESI m/z 664 (M$^+$, C$_{33}$H$_{34}$N$_3$O$_8$S$_2$ requires 664).

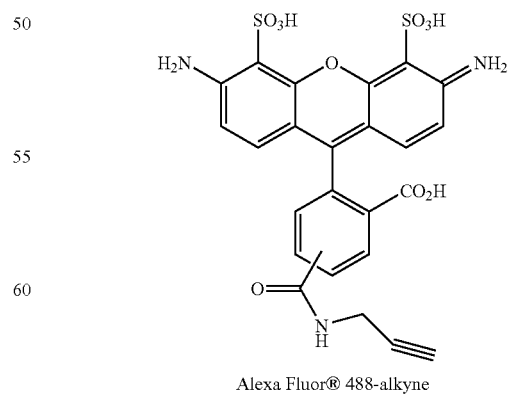

Alexa Fluor® 488-alkyne

Alexa Fluor® 488-alkyne. To a solution of Alexa Fluor® 488 carboxylic acid, succinimidyl ester, dilithium salt, mixed isomers, (51 mg, 0.08 mmol) in DMF (2.0 mL) was added propargylamine (54 µL, 0.80 mmol). The solution was stirred at RT for 4 h then concentrated in vacuo. The crude product was purified using column chromatography on silica gel (CH$_3$CN:H$_2$O, 8:2) to afford 20 mg (44%, an orange solid). TLC (CH$_3$CN:H$_2$O, 3:1) R$_f$=0.68; ESI-neg m/z 570 (M−2, C$_{24}$H$_{16}$N$_3$O$_{10}$S$_2{}^{2-}$ requires 570).

Example 32

Triarylphosphine Dye

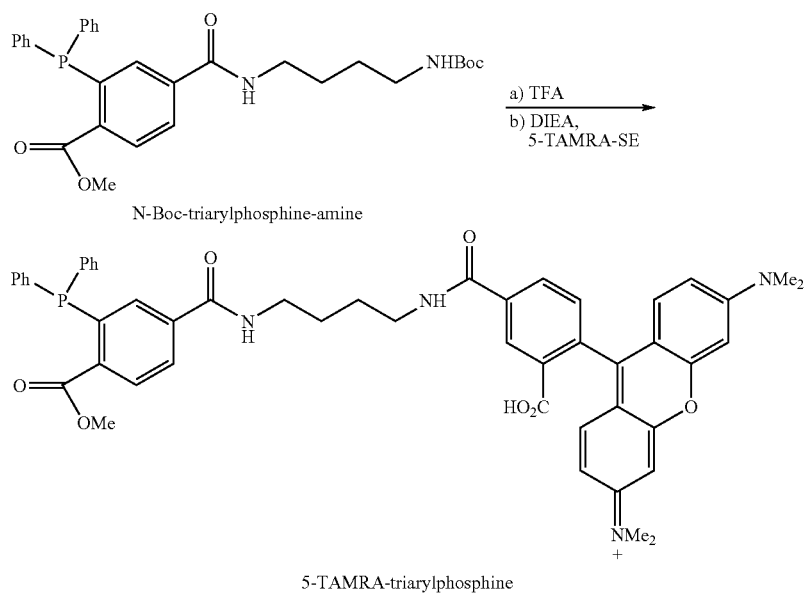

5-TAMRA-triarylphosphine. To a solution of N-Boc-triarylphosphine-amine (see Scheme 2 for synthesis, 10 mg, 0.018 mmol) in CH$_2$Cl$_2$ (1.0 mL) was added TFA (0.5 mL). The reaction solution was stirred at RT for 30 min, concentrated in vacuo, and re-evaporated twice from toluene. The crude amine (0.018 mmol, 99%) was used directly in the next reaction without further purification.

To a solution of triarylphosphine-amine (0.018 mmol) in DMF (0.2 mL) and DIEA (12 µL, 0.089 mmol) was added 5-carboxytetramethylrhodamine, succinimidyl ester (5-TAMRA-SE, 9 mg, 0.022 mmol). After stirring the solution at RT for 2.5 h, the solution was concentrated in vacuo. HPLC (Phenomenex Luna C18(2), internal diameter 10 mm, eluent 40-55% CH$_3$CN in 25 mM NH$_4$Ac, pH=7, flow rate of 5.0 mL/min) gave 4.1 mg of product (27%) t$_R$=32-34 min; TLC (MeOH:CHCl$_3$, 1:9) R$_f$=0.67, fluorescent pink spot; ESI m/z 848 (M+H$^+$, C$_{50}$H$_{48}$N$_4$O$_7$P requires 848).

Example 33

A solid silica glass surface such as a glass slide is derivatized with 3-azidopropyl(triethoxy)silane, using standard conditions for covalent attachment of alkyl(trialkoxy)silanes to glass. The residual labeling reagents are rinsed thoroughly, and the azide-derivatized glass is stored under subdued light. The azide functionalized glass surfaces are incubated in water or organic solvent such as methanol with excess acetylene-functionalized partners such as small molecules, dyes, peptides, proteins, enzymes, and nucleic acids over the course of 1-2 days in darkness in the presence of excess BCS and Cu(I), which is formed in situ from copper sulfate and sodium ascorbate. The derivatized glass surface is rinsed thoroughly with water, and stored cold either dry or suspended in solution so as to optimize the lifetime of the bound partner.

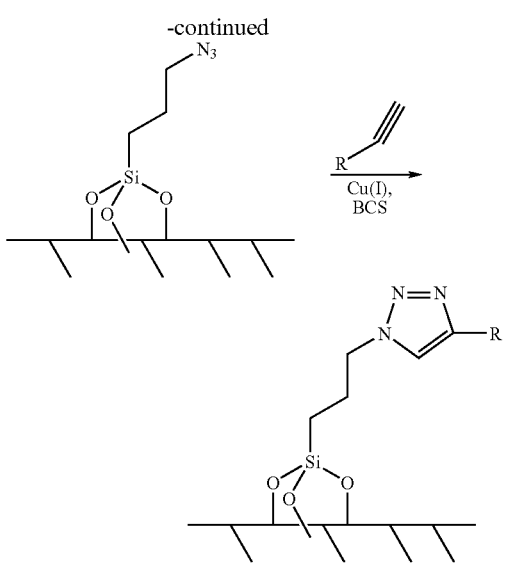

Example 34

A solid silica glass surface such as a glass slide is derivatized with 3-alkynylpropyl(triethoxy)silane, using standard conditions for covalent attachment of alkyl(trialkoxy)silanes to glass. The residual labeling reagents are rinsed thoroughly, and the alkyne-derivatized glass is stored cold. The alkyne-functionalized glass surfaces are incubated in water or organic solvent such as methanol with excess azido-functionalized partners such as small molecules, dyes, peptides, proteins, enzymes, and nucleic acids over the course of 1-2 days in darkness in the presence of excess BCS and Cu(I), which is formed in situ from copper sulfate and sodium ascorbate. The derivatized glass surface is rinsed thoroughly with water, and stored cold either dry or suspended in solution so as to optimize the lifetime of the bound partner.

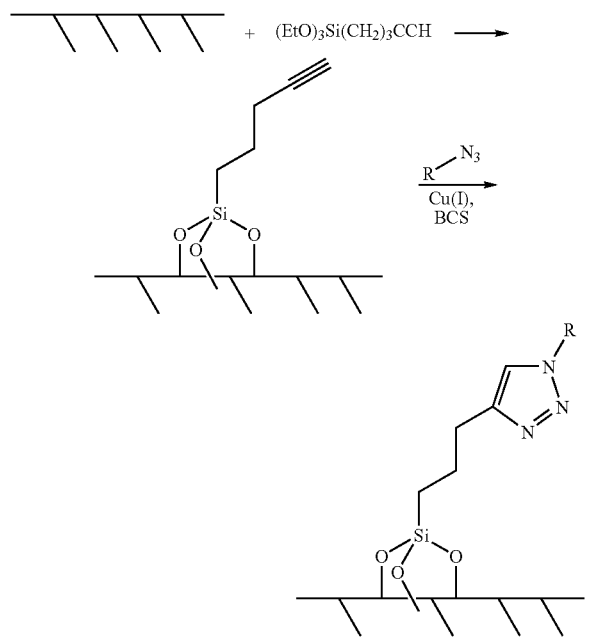

Example 35

Electrophoretic Mobility Shift Assays (EMSA)

This assay is used to determine the specificity and identification of protein binding sites on a given ds or ss DNA/RNA molecule. Currently the technique uses radiolabeled DNA which is laborious, tedious and requires high level of safety. With the advent of Click chemistry in DNA labeling one can perform the same technique with great ease and convenience.

A ss or ds nucleic acid oligo can be synthesized e.g., by IDT or Invitrogen or Sigma that has a 5' E-dUMP followed by the sequence of interest to the end user. The oligo can then be labeled with and azido Fluorphore and further used for binding to the protein of interest followed by PAGE and EMSA. Alternatively the putative sequence of DNA to which the protein binds can be designed to have a singly azido or alkyne nucleotide. If the protein binds to the sequence it would block access to the azido dye or tag resulting in no labeling. If the protein does not bind to the sequence then the DNA will get readily labeled in the click reaction giving a clear cut result.

Example 36

Click Labeling by PCR

The reaction was set up as follows:
A 2×SYBR Greener mastermix was used. It was prepared with the same components as the commercial mix (Taq polymerase, buffer, MgCl2, SYBR Greener dye) but without dNTPs and the passive reference dye ROX. The reaction mixes were prepared according to the following table:

|  |  | [final] |
|---|---|---|
| Unmodified dUTP |  |  |
| dH2O | 6.75 |  |
| 2X mix no ROX | 12.5 | 1X |
| dNTP unmodified mix 25 mM | 0.2 | 200 uM each |
| 10 uM B act 300 primers F + R | 0.5 | 200 nM each |
| 25 uM ROX | 0.05 | 50 nM |
|  | 20 |  |
| Add template | 5 |  |
| Click modified dUTP |  |  |
| dH2O | 2.95 |  |
| 2X mix no ROX | 12.5 | 1X |
| Modified dNTP mix 1.2 mM | 4 | 200 uM each |
| 10 uM B act 300 primers F + R | 0.5 | 200 nM each |
| 25 uM ROX | 0.05 | 50 nM |
|  | 20 |  |
| Add template | 5 |  |

Figure 16:
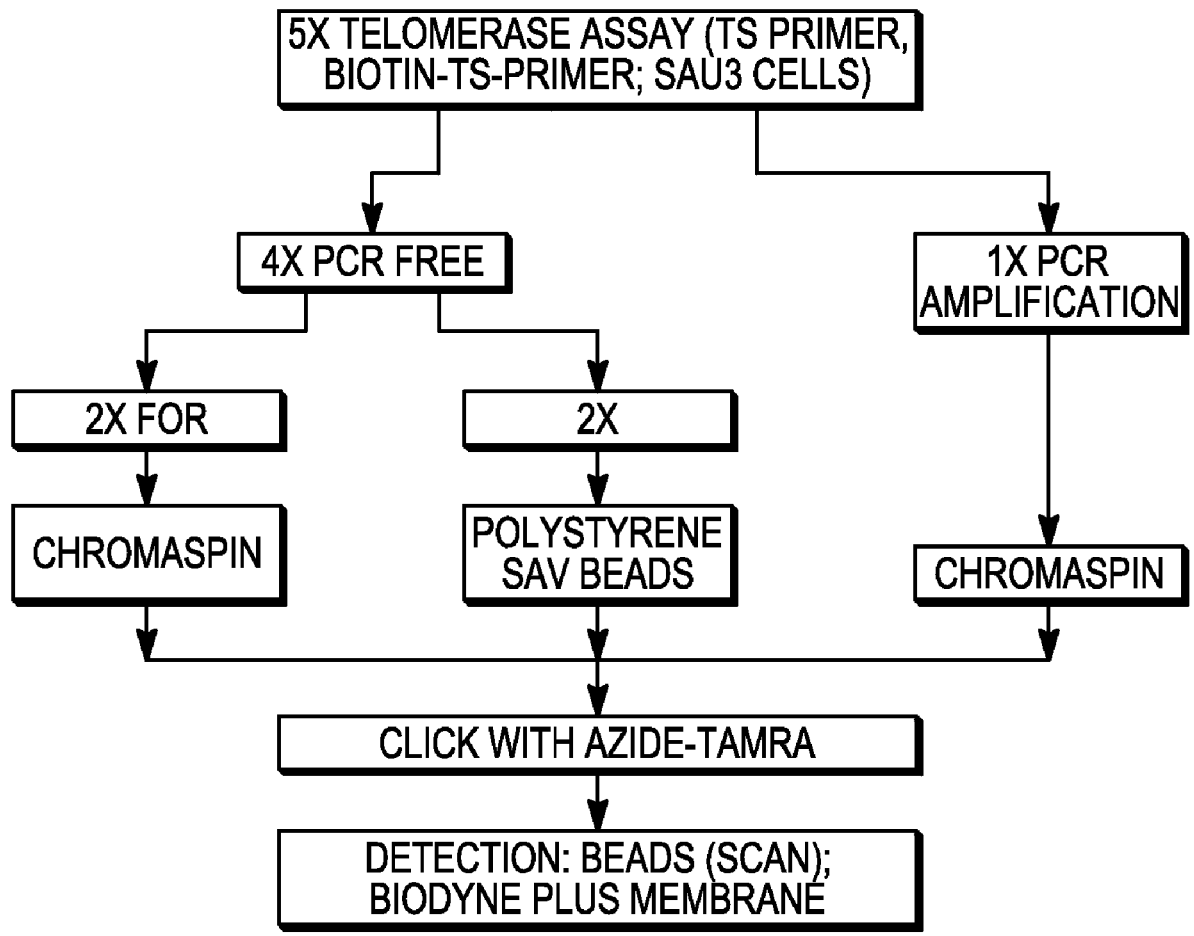

The template used was Invitrogen qPCR standards, containing 50,000,000 (5E7) copies of plasmid with the human B actin CDS, shown below. The samples were run as 3 replicates. The location of the primers is shown in FIG. 16, giving a predicted amplicon size of 293 bp.

The cycling conditions were:
Initial denaturation and activation of Taq:
95 C 10 minutes
Amplification:
1) 95 C 15 seconds
2) 60 C 30 seconds, fluorescence captured at the end of this step
Repeated for 45 cycles
Melting curve:
The amplicon was heated from 55 C to 95 C in 2 C/minute steps, with fluorescence captured at each step. SBR Green and ROX band pass filters were used to measure fluorescence, on a MX3000P machine (Stratagene).

Figure 12:
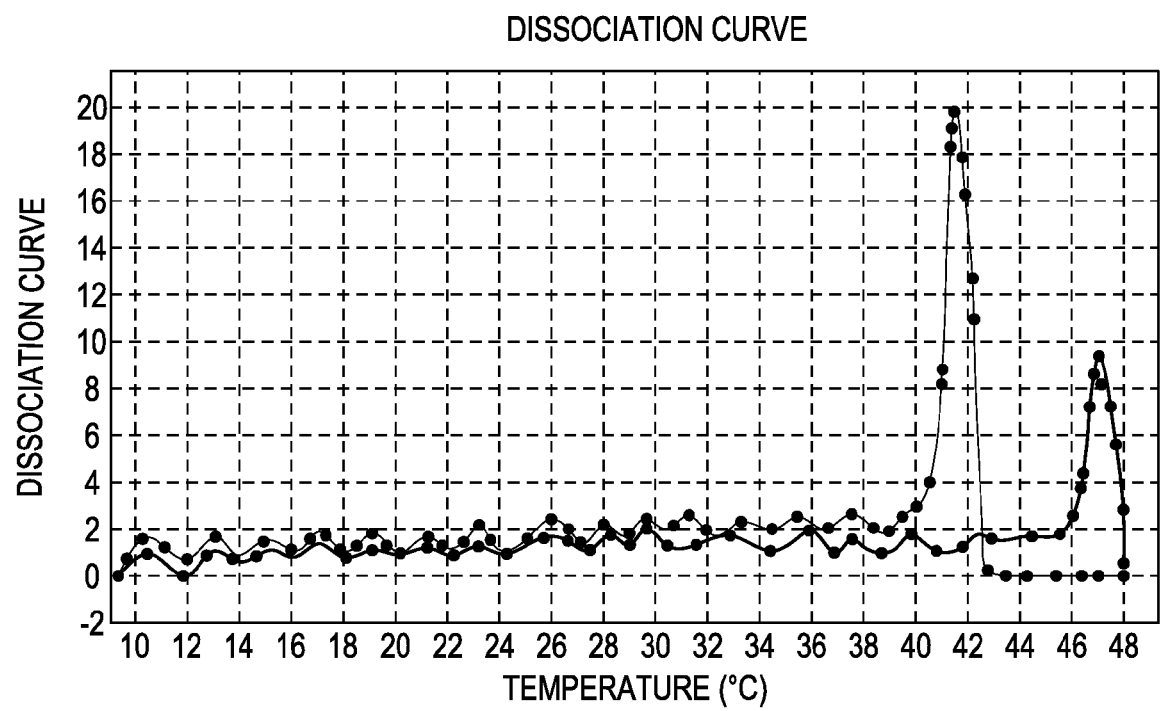

Results: The data are shown in FIG. 11 and FIG. 12. The linear amplification plot shown in FIG. 11 shows that the onset of exponential amplification or threshold cycle (CT) for the click modified dUTP mix is very similar to that shown for the unmodified dUTP mix. The average CT for click dUTP is 9.78 vs 10.97 for unmodified dUTP.

The data from the melting curve of FIG. 12 suggests a potential application for Click modified nucleotides as a way to increase the Tm of oligonucleotides. For example, if designing PCR primers in an A-T rich region, this modification could be used to raise the Tm of the primers so that shorter primers could be made that would show the same melting temperature as longer primers.

The higher Tm could be used for generating a cDNA library through random priming. Normally, random 6-8mers are used. These will naturally have a very low Tm. However the click modified random primers could potentially be used at a higher temperature for greater specificity. Researchers are using octamers to get longer and more specific reads during random priming but the click modified oligos could provide the enhanced specificity without the need for longer oligos. Thus, the advantage of using short oligos (more matches) can be combined with enhanced hybridization stability.

Example 37

Labeling of Real-Time PCR Products

Figure 13:
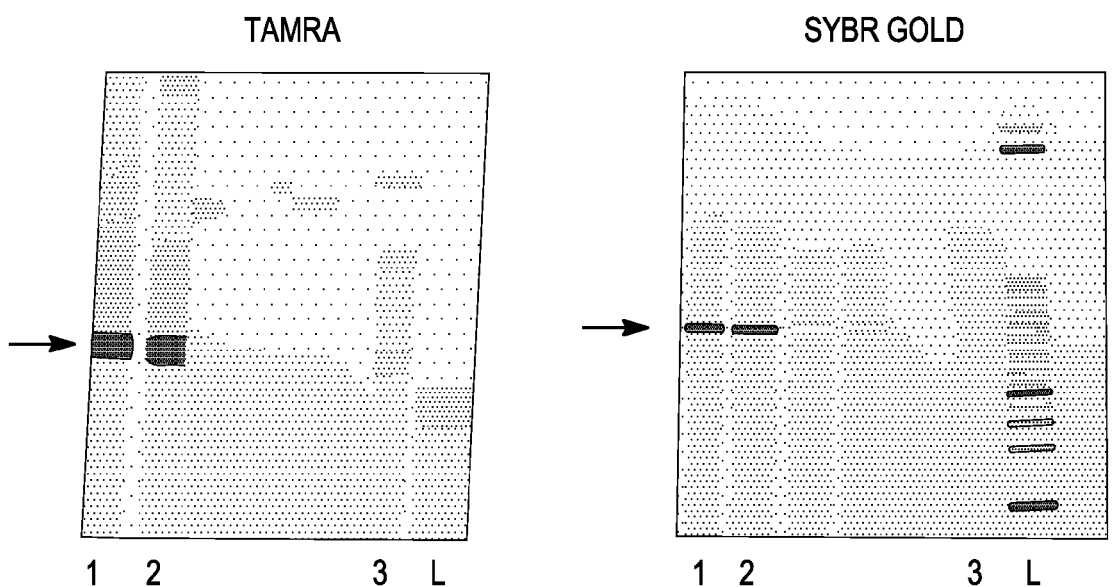

The product from the real time PCR experiment was either directly or indirectly labeled (PCR product cleaned up using Invitrogen PCR purification kit prior to Click) with azido-TAMRA in the presence of "Click" conditions. The labeling reaction was composed of a final concentration of 25% propylene glycol; 2 mM copper (II); 10 mM BCS, 10 mM Sodium Ascorbate and 50 µM azido-TAMRA. The reaction was performed for 60 minutes at room temperature. This was followed by precipitation of the DNA using 3M sodium acetate, glucagon as a carrier and 100% ethanol. The final DNA pellet was washed twice with 70% ethanol. The pellet was then dissolved in 50 ul of 10 mM TE buffer pH 8.0. The DNA solution was warmed up to enhance dissolution of the DNA pellet. 27 ul of the solution was mixed with 3 ul of 10× Blue Juice loading buffer (Invitrogen). 6 ul of the sample was loaded on to a 4-20% TBE—polyacrylamide gel. The gel was run at 10V for 10 minutes; 190V for 90 minutes. The gel was pulled out of the cassette and scanned for TAMRA (Ex: 530 nm Em: 580 nm), which is shown as the left image of FIG. 13. The same gel was then stained with SYBR GOLD for 30 minutes and then scanned as described above, as shown in the right image of FIG. 13. Lanes 1 and 2 are the PCR products that have been generated using ethynyl dUTP and other dNTPs. L is the 25 bp ladder DNA marker. The arrows point to the 300 bp labeled product. FIG. 13 also illustrates that there is no quenching of the signal.

Example 38

PCR Free Telomerase Assay

TRAPeze™ TELOMERASE assay Chemicon Kit S7700. The experiment is summarized in FIG. 22.

A 250 ul reaction mix (5×) for each of the three different reaction variables was composed as follows. 25 µl of 10× Trap buffer was mixed with 50 uM e-dNTPs (50 µM of ethynyl dUTP+50 µM of each of dATP, dGTP, and dCTP) and 344 nM of either the TS primer or biotinylated TS primer. 5 µl of Primer Mix (contains three separate primers—a K1 Fwd primer, RP Rev Primer and TSK 1 internal control primer from the (TRAPeze Telomerase Kit, Chemicon). The source of telomerase was 1000 positive control cells that are supplied with the Chemicon TRAPeze™ TELOMERASE assay kit. Sau3 cells were used as a negative control as they do not express any Telomerase enzyme. Each of the three reactions also contained 10 units of Taq DNA polymerase. 1×TRAP reaction buffer (20 mM Tris-HCl, pH 8.3, 1.5 MgCl2 63 mM KCl, 0.05% Tween 20, 1 mM EGTA)

The three different reactions were based on
(a) TS primer with +ve control cells (b) Biotinylated TS primer with +ve control cells (c) Biotinylated primer with Sau 3 cells.

After the three reaction were set up, ⅕th volume of each of the reaction was subjected to PCR aided Telomerase assay as has been discussed above. The other ⅘ volumes of each the three reactions were incubated at 30° C. for 30 minutes and then heated at 95° C. for 10 minutes. As shown in the flow chart above, one half of each of the three reactions was cleaned using size exclusion "Chromaspin" columns. The eluate was then subjected to click reaction using a final concentration of 25% propylene glycol; 2 mM copper (II); 10 mM BCS, 10 mM Sodium Ascorbate and 50 µM azido-TAMRA. The reaction was performed for 30 minutes at room temperature. This was followed by clean up on a size exclusion as described above. The TAMRA labeled dsDNA (PCR aided Telomerase products) or ss DNA (PCR free Telomerase products) were blotted on to a Biodyne plus nucleic acid binding membrane. The membrane was scanned for a TAMRA signal.

The other half of the three reactions were incubated with 25 µl of the streptavidin coated polystyrene beads (Spherotek) and incubated at 40 C for over night. The beads were washed five times with 50 mM Tris pH 8.0. Click chemistry was performed on the oligos attached to the beads using the exact same reaction composition and conditions as described above. After incubation, the labeled beads were washed 5 times with 50 mM Tris pH 8.0. The beads were semi dried in the speed vac and then scanned for TAMRA.

Figure 14:
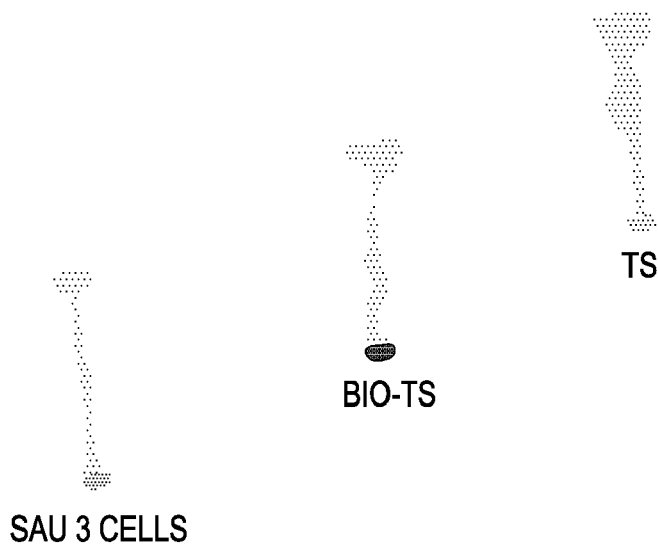

As seen in FIG. 14, the tube containing beads coated with biotinylated TS primer show a signal for TAMRA, while the tubes with either TS primer or negative control cells do not show the signal.

Figure 15:
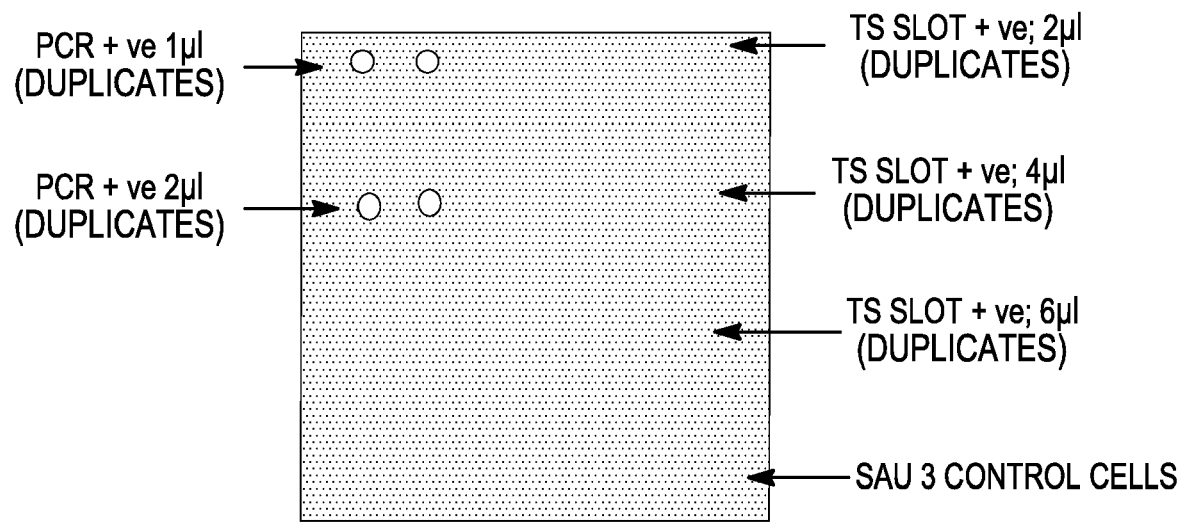

Additionally, as shown in FIG. 15, spots on the PCR aided +ve control and TS biotinylated primer show TAMRA signal on the Biodyne nucleic acid membrane. The signal intensity from the PCR positive control is far greater than PCR free Telomerase assay.

Example 39

Tagging Phosphoproteins Using Nucleotide Analogs

Phosphoproteins are labeled in vivo or in vitro using alkyne or azide-tagged nucleotides whereby the azide or alkyne moiety is placed on the gamma phosphate. For example one of the nucleotides shown below is added to a reaction mixture containing a protein kinase and a kinase target molecule. After tagging the molecule is reacted with the appropriate alkyne or azide detection or affinity reagent for quantitation, visualization, or enrichment. In one example reaction, modified nucleotide substrates may be added directly to cultured cells for metabolic incorporation of the tagged gamma-phosphate molecule into cellular macromolecules including proteins. The process may involve treatment of the cells with pharmacological agents to detect alterations in phosphorylation dynamics. Entry of the compounds into live cultured cells could be enhanced by modifying the nucleotides with functional groups that would afford permeability, or by concomitant addition of cell permeablizing agents. In another example reaction, the kinase reaction could be performed in vitro using cellular extracts as the source of kinases and substrates. The modified nucleotides is added to the reaction mixture and the reaction mixtures incubated with or without the addition of pharmacological agents of interest. The in vitro reaction optionally entails adding an exogenous kinase or substrate source to the cellular extract along with the nucleotide analogs. In another application, the method is used in vitro without cellular extracts, using purified kinases and kinase substrates. In all of the disclosed examples the reaction mix may contain a buffer optimized for the particular kinases of interest, a kinase source, a metal ion source, glycerol, nucleotide ATP analog, and ATP. The "click" detection reaction with an alkyne probe would be performed in the presence of copper (I), or copper(II) in the presence of a copper(II) reducing agent, a copper(I) chelating agent, and an appropriate buffer to maintaining optimal pH conditions.

ATP-alkyne:

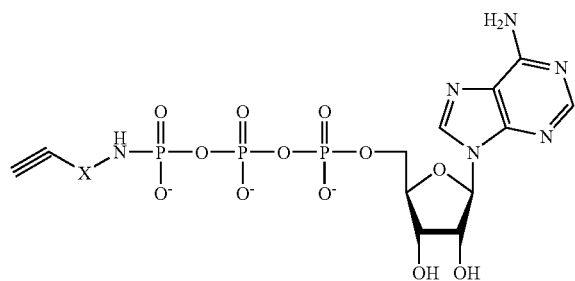

ATP-Azide:

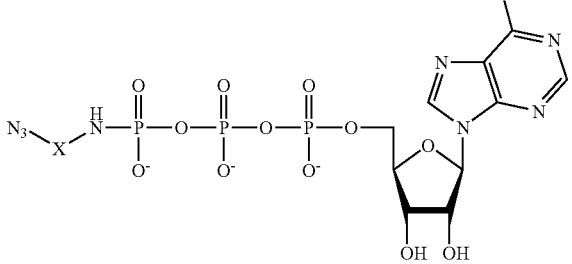

X = a linker

The reagents employed in the examples are commercially available or can be prepared using commercially available instrumentation, methods, or reagents known in the art. The foregoing examples illustrate various aspects of the invention and practice of the methods of the invention. The examples are not intended to provide an exhaustive description of the many different embodiments of the invention. Thus, although the forgoing invention has been described in some detail by way of illustration and example for purposes of clarity of understanding, those of ordinary skill in the art will realize readily that many changes and modifications can be made thereto without departing from the spirit or scope of the appended claims.

Each of the references cited herein are hereby incorporated by reference as if set forth fully herein.

We claim:

1. A method of forming a nucleic acid conjugate, wherein the method comprises:
   a) incorporating a terminal alkyne modified nucleotide into the nucleic acid polymer by contacting the terminal alkyne modified nucleotide with at least one other nucleotide in the presence of a DNA amplification enzyme to form a terminal alkyne modified nucleic acid polymer; and
   b) contacting the terminal alkyne modified nucleic acid polymer with a carrier molecule or solid support that comprises an azido moiety to form a nucleic acid polymer-carrier molecule, or nucleic acid polymer-solid support conjugate.

2. The method according to claim 1, wherein the carrier molecule is an amino acid, a peptide, a protein, a polysaccharide, a nucleotide, a nucleoside, an oligonucleotide, a nucleic acid, a hapten, a psoralen, a drug, a hormone, a lipid, a lipid assembly, a synthetic polymer, a polymeric microparticle, a biological cell or a virus.

3. The method according to claim 1, wherein the carrier molecule comprises an antibody or fragment thereof, an avidin or streptavidin, a biotin, a blood component protein, a dextran, an enzyme, an enzyme inhibitor, a hormone, an IgG binding protein, a fluorescent protein, a growth factor, a lectin, a lipopolysaccharide, a microorganism, a metal binding protein, a metal chelating moiety, a non-biological microparticle, a peptide toxin, a phosphotidylserine-binding protein, a structural protein, a small-molecule drug, or a tyramide.

4. The method according to claim 1, wherein the solid support is a microfluidic chip, a silicon chip, a microscope slide, a microplate well, silica gels, polymeric membranes, particles, derivatized plastic films, glass beads, cotton, plastic beads, alumina gels, polysaccharides, polyvinylchloride, polypropylene, polyethylene, nylon, latex bead, magnetic bead, paramagnetic bead, or superparamagnetic bead.

5. The method according to claim 1, wherein the solid support is Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose or starch.

6. The method of claim 3, wherein the non-biological microparticle is a nanoparticle.

7. The method of claim 4, wherein the particle is a nanoparticle.

8. The method according to claim 1, wherein the nucleic acid enzyme is a DNA polymerase.

9. The method according to claim 1, wherein the nucleic acid enzyme is a RNA polymerase.

* * * * *